United States Patent [19]

Kamp et al.

[11] Patent Number: 5,994,525
[45] Date of Patent: Nov. 30, 1999

[54] **NUCLEIC ACID ENCODING *ACTINOBACILLUS PLEUROPNEUMONIAE* CYTOLYTIC PROTEINS**

[76] Inventors: Elbarte Margriet Kamp, Wijngaard 27, 8212 CC Lelystad; Marinus Adrianus Smits, Mastmeen 18, 3844 Ke Harderwijk, both of Netherlands

[21] Appl. No.: 08/488,706

[22] Filed: Jun. 9, 1995

Related U.S. Application Data

[62] Division of application No. 08/138,609, Oct. 15, 1993, abandoned, which is a continuation of application No. 07/722,971, Jun. 28, 1991, abandoned.

[51] Int. Cl.$^6$ .............................. C07H 24/04; C12N 1/21; C12N 15/31; A61K 39/102
[52] U.S. Cl. ...................... 536/24.1; 536/22.1; 536/23.7; 435/252.3; 435/320.1; 435/69.1; 435/69.3; 435/71.1; 435/71.2; 424/256.1
[58] Field of Search ................................ 435/69.3, 252.3, 435/320.1, 69.1, 71.1, 71.2; 424/184.1, 185.1, 69.3; 536/22.1, 23.7, 24.1

[56] References Cited

FOREIGN PATENT DOCUMENTS

| 0354628 | 2/1990 | European Pat. Off. ..... A61K 39/102 |
| 9106653 | 5/1991 | WIPO ............................ C12N 15/31 |

OTHER PUBLICATIONS

Rycroft et al Journ of Gen Microl 137: 561–568 Mar. 1991.
Frey et al Vet Microbiol 28: 303–312, 1991.
Inzana et al Microb. Pathogen. 10: 281–296, 1991.
Fedonka–Cray et al I&I 58: 358–365 Feb., 1990.
Van den Bosch et al Proceedings, Inter Pig Vet Soc., 11th Cong Jul. 1990 Abstract only).
Kamp et al Journ of Clin Microb 27: 1187–1191, 1989.
Frey et al Journal of General Microbiology 139: 1723–1728, 1993.
Bertram, Can. J. Vet. Res., 54 553–S–56 (199).
Frey et al., J. Clin. Microbiol. 28:232–6 (1990).
Kamp et al., J. Clin. Microbiol., 27: 1187–1991 (1989).
Chang et al., DNA, 8: 635–647 (1989).
MacInnes et al., J. Bacteriol., 172:4587–92 (1990).
Strathdee et al., J. Bacteriol. 171:2 916–928 (1989).
Gygi et al., Mol.–Microbiology, 4(1): 123–128 (199).
Strathdee et al., Infect. Immun. 55:12, 3233–6 (1987).
Frey et al., FEMS Micrbiol. Lett, 55: 41–45 (1988).
Strathdee et al., J. of Bacteriol., 171:916–928 (1989).
Strathdee et al., J. of Bacteriol., 171:5955–5962 (1989).
Frey et al., Infect. and Immunon., 56:2570–5 (1988).
Devenish et al., Infect. and Immun., 57:3210–13 (1989).
Fedorka–Cray et al., Infect. and Immun., 58:358–365 (1990).
Devenish et al., Infect. and Immun., 58:3892–32 (1990).
Frey et al., Vet, Microbiol., 28:303–312 (1991).
Inzana et al., Microbia Pathogenesis, 10:281–296 (1991).
Frey et al., Vet. Microbiol., 28:61–73 (1991).
Rycroft et al., J. of Gen. Microbiol., 137:561–568 (1991).
Frey et al Veterinary Microbiology 28:303–312, 199.
Chang et al DNA 8:635–647, 1989.
Frey et al FEMS Microb. Lett. 8:41–46, 1988.
Gygi et al. Molec. Microbiology 4:123–128, 1990.
Houghten et al Vaccines 86, pp. 21–25.
Kamp et al Journ of Clin Microb 27:1184–1191, 1989.
Devenish et al, Infect & Immunity 58:3829–3832, 1990.
Inzana et al Microbiol Pathogen. 10:281–296, 1990.
Rycroft et al, Journ of Gen Microbiol 137:561–568, 1991.
Frey et al Vet Microbiol 28:303–312 1991.
Fedorka–Cray, Dissertation Abs 50:5501–13 1990 (Abstract–only).
Van den Bush et al (Proceedings International Pig Vet Soc 11th Congress Jul. 1990, Abst. Only.

*Primary Examiner*—Hazel F. Sidberry
*Attorney, Agent, or Firm*—Webb, Ziesenheim, Bruening, Logsdon, Orkin & Hanson, P.C.

[57] ABSTRACT

The invention provides a vaccine for the prevention and/or the treatment of infection by *Actinobacillus pleuropneumoniae*, the causative agent of porcine pleuropneumonia, which vaccine contains at least an immunogenic part of at least one cytolytic protein of *A. pleuropneumoniae* produced by recombinant DNA, and detoxified derivatives thereof. Three of such cytolytic proteins are identified and a vaccine containing these, or parts or derivatives thereof, ensures protection against all known serotypes of *A. pleuropneumoniae*. The cytolytic proteins are produced by inserting a nucleotide sequence encoding one or more of the proteins or parts thereof in a host cell, cultivating the host cell and recovering the proteins. another vaccine contains the genetic information for one or more of the cytolytic proteins, and a passive vaccine contains antibodies against these proteins. The invention further provides monoclonal antibodies and DNA probes for use in diagnostics.

6 Claims, 18 Drawing Sheets

```
AGATTAATGAGCGATATTGTTATAAAATCATAATGTAAACCTCATTTGTAATGAATTGGTAAATTATATAAA

TAATCAAAAAACTTACTTTTTTTTATTTTTATCGGTAAGTATTTACAATCAAGTCAGACAAACGGCAATATT

GTTATAAATCTGGGGGGATGAATGAGTAAAAAAATTAATGGATTTGAGGTTTTAGGAGAGGTGGCATGGTTA
    ClyI C           METSerLysLysIleAsnGlyPheGluValLeuGlyGluValAlaTrpLeu

TGGGCAAGTTCTCCTTTACATCGAAAGTGGCCGCTTTCTTTGTTAGCAATTAATGTGCTACCTGCGATTGAG
TrpAlaSerSerProLeuHisArgLysTrpProLeuSerLeuLeuAlaIleAsnValLeuProAlaIleGlu

AGTAATCAATATGTTTTGTTAAAGCGTGACGGTTTTCCTATTGCATTTTGTAGCTGGGCAAATTTGAATTTG
SerAsnGlnTyrValLeuLeuLysArgAspGlyPheProIleAlaPheCysSerTrpAlaAsnLeuAsnLeu

GAAAATGAAATTAAATACCTTGATGATGTTGCCTCGCTAGTTGCGGATGATTGGACTTCCGGCGATCGTCGA
GluAsnGluIleLysTyrLeuAspAspValAlaSerLeuValAlaAspAspTrpThrSerGlyAspArgArg

TGGTTTATAGATTGGATAGCACCGTTCGGAGACAGTGCCGCATTATACAAACATATGCGAGATAACTTCCCG
TrpPheIleAspTrpIleAlaProPheGlyAspSerAlaAlaLeuTyrLysHisMETArgAspAsnPhePro

AATGAGCTGTTTAGGGCTATTCGAGTTGATCCGGACTCTCGAGTAGGGAAAATTTCAGAATTTCATGGAGGA
AsnGluLeuPheArgAlaIleArgValAspProAspSerArgValGlyLysIleSerGluPheHisGlyGly

AAAATTGATAAGAAACTGGCAAGTAAAATTTTTTCAACAATATCACTTTGAATTAATGAGTGAGCTAAAAAAT
LysIleAspLysLysLeuAlaSerLysIlePheGlnGlnTyrHisPheGluLeuMETSerGluLeuLysAsn

AAACAAAATTTTAAATTTTCATTAGTAAATAGCTAAGGAGACAACATGGCTAACTCTCAGCTCGATAGAGTC
LysGlnAsnPheLysPheSerLeuValAsnSer    ClyI A METAlaAsnSerGlnLeuAspArgVal

AAAGGATTGATTGATTCACTTAATCAACATACAAAAAGTGCAGCTAAATCAGGTGCCGGCGCATTAAAAAAT
LysGlyLeuIleAspSerLeuAsnGlnHisThrLysSerAlaAlaLysSerGlyAlaGlyAlaLeuLysAsn

GGTTTGGGACAGGTGAAGCAAGCAGGGCAGAAATTAATTTTATATATTCCGAAAGATTATCAAGCTAGTACC
GlyLeuGlyGlnValLysGlnAlaGlyGlnLysLeuIleLeuTyrIleProLysAspTyrGlnAlaSerThr

GGCTCAAGTCTTAATGATTTAGTGAAAGCGGCGGAGGCTTTAGGGATCGAAGTACATCGCTCGGAAAAAAAC
GlySerSerLeuAsnAspLeuValLysAlaAlaGluAlaLeuGlyIleGluValHisArgSerGluLysAsn

GGTACCGCACTAGCGAAAGAATTATTCGGTACAACGGAAAAACTATTAGGTTTCTCGGAACGAGGCATCGCA
GlyThrAlaLeuAlaLysGluLeuPheGlyThrThrGluLysLeuLeuGlyPheSerGluArgGlyIleAla

TTATTTGCACCTCAGTTTGATAAGTTACTGAATAAGAACCAAAAATTAAGTAAATCGCTCGGCGGTTCATCG
LeuPheAlaProGlnPheAspLysLeuLeuAsnLysAsnGlnLysLeuSerLysSerLeuGlyGlySerSer

GAAGCATTAGGACAACGTTTAAATAAAAACGCAAACGGCACTTTCAGCCTTACAAAGTTTCTTAGGTACGGCT
GluAlaLeuGlyGlnArgLeuAsnLysThrGlnThrAlaLeuSerAlaLeuGlnSerPheLeuGlyThrAla

ATTGCGGGTATGGATCTTGATAGCCTGCTTCGTCGCCGTAGAAACGGTGAGGACGTCAGTGGTTCGGAATTA
IleAlaGlyMETAspLeuAspSerLeuLeuArgArgArgArgAsnGlyGluAspValSerGlySerGluLeu

GCTAAAGCAGGTGTGGATCTAGCCGCTCAGTTAGTGGATAACATTGCAAGTGCAACGGGTACGGTGGATGCG
AlaLysAlaGlyValAspLeuAlaAlaGlnLeuValAspAsnIleAlaSerAlaThrGlyThrValAspAla

TTTGCCGAACAATTAGGTAAATTGGGCAATGCCTTATCTAACACTCGCTTAAGCGGTTTAGCAAGTAAGTTA
PheAlaGluGlnLeuGlyLysLeuGlyAsnAlaLeuSerAsnThrArgLeuSerGlyLeuAlaSerLysLeu
```

FIG. 1A

```
AATAACCTTCCAGATTTAAGCCTTGCAGGACCTGGGTTTGATGCCGTATCAGGTATCTTATCTGTTGTTTCG
AsnAsnLeuProAspLeuSerLeuAlaGlyProGlyPheAspAlaValSerGlyIleLeuSerValValSer

GCTTCATTCATTTTAAGTAATAAAGATGCCGATGCAGGTACAAAAGCGGCGGCAGGTATTGAAATCTCAACT
AlaSerPheIleLeuSerAsnLysAspAlaAspAlaGlyThrLysAlaAlaAlaGlyIleGluIleSerThr

AAAATCTTAGGCAATATCGGTAAAGCGGTTTCTCAATATATTATTGCGCAACGTGTGGCGGCAGGCTTATCC
LysIleLeuGlyAsnIleGlyLysAlaValSerGlnTyrIleIleAlaGlnArgValAlaAlaGlyLeuSer

ACAACTGCGGCAACCGGTGGTTTAATCGGTTCGGTCGTAGCATTAGCGATTAGCCCGCTTTCGTTCTTAAAT
ThrThrAlaAlaThrGlyGlyLeuIleGlySerValValAlaLeuAlaIleSerProLeuSerPheLeuAsn

GTTGCGGATAAGTTTGAACGTGCGAAACAGCTTGAACAATATTCGGAGCGCTTTAAAAAGTTCGGTTATAAA
ValAlaAspLysPheGluArgAlaLysGlnLeuGluGlnTyrSerGluArgPheLysLysPheGlyTyrLys

GGTGATAGTTTATTAGCTTCATTCTACCGTGAAACCGGTGCGATTGAAGCGGCATTAACCACGATTAACAGT
GlyAspSerLeuLeuAlaSerPheTyrArgGluThrGlyAlaIleGluAlaAlaLeuThrThrIleAsnSer

GTGTTAAGTGCGGCTTCCGCAGGTGTTGGGGCTGCTGCAACCGGCTCATTAGTCGGTGCGCCGGTAGCAGCT
ValLeuSerAlaAlaSerAlaGlyValGlyAlaAlaAlaThrGlySerLeuValGlyAlaProValAlaAla

TTAGTTAGTGCAATCACCGGTATTATTTCAGGTATTTTAGATGCTTCTAAACAGGCAATCTTCGAACGAGTT
LeuValSerAlaIleThrGlyIleIleSerGlyIleLeuAspAlaSerLysGlnAlaIlePheGluArgVal

GCAACGAAATTAGCGAATAAGATTGACGAATGGGAGAAAAAACACGGTAAAAACTATTTTGAAAACGGTTAT
AlaThrLysLeuAlaAsnLysIleAspGluTrpGluLysLysHisGlyLysAsnTyrPheGluAsnGlyTyr

GACGCCCGCCATTCCGCATTCTTAGAAGATACCTTTGAATTGTTATCACAATACAATAAAGAGTATTCGGTA
AspAlaArgHisSerAlaPheLeuGluAspThrPheGluLeuLeuSerGlnTyrAsnLysGluTyrSerVal

GAGCGTGTCGTTGCTATTACGCAACAGCGTTGGGATGTCAATATCGGTGAACTTGCCGGCATTACTCGCAAA
GluArgValValAlaIleThrGlnGlnArgTrpAspValAsnIleGlyGluLeuAlaGlyIleThrArgLys

GGTTCTGATACGAAAAGCGGTAAAGCTTACGTTGATTTCTTTGAAGAAGGAAAACTTTTAGAGAAAGAACCG
GlySerAspThrLysSerGlyLysAlaTyrValAspPhePheGluGluGlyLysLeuLeuGluLysGluPro

GATCGTTTTGATAAAAAAGTGTTTGATCCGCTTGAAGGTAAAATCGACCTTTCTTCAATTAACAAAACCACT
AspArgPheAspLysLysValPheAspProLeuGluGlyLysIleAspLeuSerSerIleAsnLysThrThr

TTATTGAAATTTGTTACCCCGGTCTTTACCGCAGGTGAAGAGATTCGTGAGCGTAAGCAAACCGGTAAATAC
LeuLeuLysPheValThrProValPheThrAlaGlyGluGluIleArgGluArgLysGlnThrGlyLysTyr

GAATATATGACCGAATTATTCGTTAAAGGTAAAGAAAAATGGGTGGTAACCGGTGTGCAGTCACATAATGCG
GluTyrMETThrGluLeuPheValLysGlyLysGluLysTrpValValThrGlyValGlnSerHisAsnAla

ATTTATGACTATACGAATCTTATCCAATTAGCGATAGATAAAAAAGGTGAAAAACGTCAAGTGACCATTGAA
IleTyrAspTyrThrAsnLeuIleGlnLeuAlaIleAspLysLysGlyGluLysArgGlnValThrIleGlu

TCTCATTTGGGTGAGAAAAATGATCGTATATATCTTTCATCCGGTTCATCTATCGTATATGCGGGTAACGGA
SerHisLeuGlyGluLysAsnAspArgIleTyrLeuSerSerGlySerSerIleValTyrAlaGlyAsnGly

CATGATGTAGCATATTACGATAAAACCGATACAGGTTACTTAACATTTGACGGACAAAGTGCACAGAAAGCC
HisAspValAlaTyrTyrAspLysThrAspThrGlyTyrLeuThrPheAspGlyGlnSerAlaGlnLysAla

GGTGAATATATTGTCACTAAAGAACTTAAAGCTGATGTAAAAGTTTTAAAAGAAGTGGTTAAAACTCAGGAT
GlyGluTyrIleValThrLysGluLeuLysAlaAspValLysValLeuLysGluValValLysThrGlnAsp
```

FIG. 1B

```
ATTTCAGTTGGAAAACGCAGTGAAAAATTAGAATATCGTGATTATGAGTTAAGCCCATTCGAACTTGGGAAC
IleSerValGlyLysArgSerGluLysLeuGluTyrArgAspTyrGluLeuSerProPheGluLeuGlyAsn

GGTATCAGAGCTAAAGATGAATTACATTCTGTTGAAGAAATTATCGGTAGTAATCGTAAAGACAAATTCTTT
GlyIleArgAlaLysAspGluLeuHisSerValGluGluIleIleGlySerAsnArgLysAspLysPhePhe

GGTAGTCGCTTTACCGATATTTTCCATGGTGCGAAAGGCGATGATGAAATCTACGGTAATGACGGCCACGAT
GlySerArgPheThrAspIlePheHisGlyAlaLysGlyAspAspGluIleTyrGlyAsnAspGlyHisAsp

ATCTTATACGGAGACGACGGTAATGATGTAATCCATGGCGGTGACGGTAACGACCATCTTGTTGGTGGTAAC
IleLeuTyrGlyAspAspGlyAsnAspValIleHisGlyGlyAspGlyAsnAspHisLeuValGlyGlyAsn

GGAAACGACCGATTAATCGGCGGAAAAGGTAATAATTTCCTTAATGGCGGTGATGGTGACGATGAGTTGCAG
GlyAsnAspArgLeuIleGlyGlyLysGlyAsnAsnPheLeuAsnGlyGlyAspGlyAspAspGluLeuGln

GTCTTTGAGGGTCAATACAACGTATTATTAGGTGGTGCGGGTAATGACATTCTGTATGGCAGCGATGGTACT
ValPheGluGlyGlnTyrAsnValLeuLeuGlyGlyAlaGlyAsnAspIleLeuTyrGlySerAspGlyThr

AACTTATTTGACGGTGGTGTAGGCAATGACAAAATCTACGGTGGTTTAGGTAAGGATATTTATCGCTACAGT
AsnLeuPheAspGlyGlyValGlyAsnAspLysIleTyrGlyGlyLeuGlyLysAspIleTyrArgTyrSer

AAGGAGTACGGTCGTCATATCATTATTGAGAAAGGCGGTGATGATGATACGTTATTGTTATCGGATCTTAGT
LysGluTyrGlyArgHisIleIleIleGluLysGlyGlyAspAspAspThrLeuLeuLeuSerAspLeuSer

TTTAAAGATGTAGGATTTATCAGAATCGGTGATGATCTTCTTGTGAATAAAAGAATCGGAGGAACACTGTAT
PheLysAspValGlyPheIleArgIleGlyAspAspLeuLeuValAsnLysArgIleGlyGlyThrLeuTyr

TACCATGAAGATTACAATGGGAATGCGCTCACGATTAAAGATTGGTTCAAGGAAGGTAAAGAAGGACAAAAT
TyrHisGluAspTyrAsnGlyAsnAlaLeuThrIleLysAspTrpPheLysGluGlyLysGluGlyGlnAsn

AATAAAATTGAAAAAATCGTTGATAAAGATGGAGCTTATGTTTTAAGCCAATATCTGACTGAACTGACAGCT
AsnLysIleGluLysIleValAspLysAspGlyAlaTyrValLeuSerGlnTyrLeuThrGluLeuThrAla

CCTGGAAGAGGTATCAATTACTTTAATGGGTTAGAAGAAAAATTGTATTATGGAGAAGGATATAATGCACTT
ProGlyArgGlyIleAsnTyrPheAsnGlyLeuGluGluLysLeuTyrTyrGlyGluGlyTyrAsnAlaLeu

CCTCAACTCAGAAAAGATATTGAACAAATCATTTCATCTACGGGTGCATTTACCGGTGATCACGGAAAAGTA
ProGlnLeuArgLysAspIleGluGlnIleIleSerSerThrGlyAlaPheThrGlyAspHisGlyLysVal

TCTGTAGGCTCAGGCGGACCGTTAGTCTATAATAACTCAGCTAACAATGTAGCAATTCTTTGAGTTATTCTT
SerValGlySerGlyGlyProLeuValTyrAsnAsnSerAlaAsnAsnValAlaIleLeu---

TAGCACAAGCAGCTTAAGATAGTTATTTTTAGATGATAAATAGCAATCCTATATATATTAGGTGTGTAGGAT

TGCTATTTTATTTATGGAGGAGCAAATGGATTTTTTATCGGGAAGAAGACTACGGATTATACGCACTGACGAT
ClyI B                 METAspPheTyrArgGluGluAspTyrGlyLeuTyrAlaLeuThrIle

TTTAGCCCAGTACCATAATATTGCTGTAAATCCGGAAGAACTAAAACATAAATTCGACCTTGAAGGAAAAGG
  LeuAlaGlnTyrHisAsnIleAlaValAsnProGluGluLeuLysHisLysPheAspLeuGluGlyLysGly

CTTAGATCTAACCGCTTGGCTATTAGCCGCAAAATCATTAGAACTTAAAGCAAAACAAGTAAAAAAAGCGAT
  LeuAspLeuThrAlaTrpLeuLeuAlaAlaLysSerLeuGluLeuLysAlaLysGlnValLysLysAlaIle

TGATCGTTTGGCCGTTTATCGCACTACCGGCACTTGTATGGCGAGAAGACGGTAAACATTTTATTTTGACTAA
  AspArgLeuAlaPheIleAlaLeuProAlaLeuValTrpArgGluAspGlyLysHisPheIleLeuThrLys
```

FIG. 1C

```
AATTGATAATGAAGCAAAAAAATATTTAATTTTTGATTTGGAAACGCATAATCCTCGCATTTTGGAACAAGC
 IleAspAsnGluAlaLysLysTyrLeuIlePheAspLeuGluThrHisAsnProArgIleLeuGluGlnAla

GGAATTCGAGAGCTTATACCAAGGAAAACTGATTTTAGTTGCATCAAGAGCTTCCATCGTAGGTAAGCTGGC
 GluPheGluSerLeuTyrGlnGlyLysLeuIleLeuValAlaSerArgAlaSerIleValGlyLysLeuAla

AAAGTTTGACTTCACTTGGTTTATACCGGCGGTAATTAAGTATCGTAAGATTTTTATTGAAACGTTAATTGT
 LysPheAspPheThrTrpPheIleProAlaValIleLysTyrArgLysIlePheIleGluThrLeuIleVal

TTCAATTTTTTTGCAAATTTTCGCACTAATTACACCGCTTTTTTTCCAAGTCGTGATGGATAAAGTCTTGGT
 SerIlePheLeuGlnIlePheAlaLeuIleThrProLeuPhePheGlnValValMETAspLysValLeuVal

ACACCGAGGTTTTTCAACCTTAAATGTGATTACGGTGGCATTAGCGATCGTCGTGCTGTTTGAAATTGTGCT
 HisArgGlyPheSerThrLeuAsnValIleThrValAlaLeuAlaIleValValLeuPheGluIleValLeu

AAACGGTTTACGTACCTATATTTTTGCGCATAGTACCAGCCGTATTGATGTGGAGTTGGGAGCAAGATTATT
 AsnGlyLeuArgThrTyrIlePheAlaHisSerThrSerArgIleAspValGluLeuGlyAlaArgLeuPhe

CAGACATTTATTAGCACTCCCAATCTCTTATTTTGAAAATCGTCGAGTCGGCGATACGGTGGCTCGTGTACG
 ArgHisLeuLeuAlaLeuProIleSerTyrPheGluAsnArgArgValGlyAspThrValAlaArgValArg

AGAACTCGATCAAATTCGTAACTTCTTAACCGGGCAGGCACTTACTTCCGTGTTGGATTTAATGTTTTCCTT
 GluLeuAspGlnIleArgAsnPheLeuThrGlyGlnAlaLeuThrSerValLeuAspLeuMETPheSerPhe

TATCTTCTTTGCAGTGATGTGGTATTACAGCCCTAAACTTACTCTTGTGATTTTAGGCTCGTTACCGTTTTA
 IlePhePheAlaValMETTrpTyrTyrSerProLysLeuThrLeuValIleLeuGlySerLeuProPheTyr

TATGGGGTGGTCGATTTTTATCAGCCCTATTTTACGTCGCCGTTTAGATGAAAAATTCGCACGTGGTGCGGA
 METGlyTrpSerIlePheIleSerProIleLeuArgArgArgLeuAspGluLysPheAlaArgGlyAlaAsp

CAATCAGTCATTCTTAGTGGAATCGGTGACTGCAATCAATACGATTAAAGCGTTGGCGGTTACCCCTCAAAT
 AsnGlnSerPheLeuValGluSerValThrAlaIleAsnThrIleLysAlaLeuAlaValThrProGlnMET

GACTAATACCTGGGATAAGCAATTAGCCAGCTATGTATCGGCGGGATTCCGTGTAACCACATTAGCTACTAT
 ThrAsnThrTrpAspLysGlnLeuAlaSerTyrValSerAlaGlyPheArgValThrThrLeuAlaThrIle

CGGACAGCAAGGTGTACAATTTATTCAAAAAGTCGTGATGGTTATTACCTTATGGCTAGGCGCACATTTAGT
 GlyGlnGlnGlyValGlnPheIleGlnLysValValMETValIleThrLeuTrpLeuGlyAlaHisLeuVal

GATTTCAGGCGATTTAAGTATCGGACAATTAATCGCATTTAATATGTTATCCGGTCAAGTGATTGCACCGGT
 IleSerGlyAspLeuSerIleGlyGlnLeuIleAlaPheAsnMETLeuSerGlyGlnValIleAlaProVal

GATTCGTTTAGCGCAACTTTGGCAAGATTTCCAACAAGTGGGAATTTCGGTAACGCGTTTAGGTGATGTTTT
 IleArgLeuAlaGlnLeuTrpGlnAspPheGlnGlnValGlyIleSerValThrArgLeuGlyAspValLeu

AAACTCTCCGACCGAGAGCTATCAAGGAAAATTGGCGTTACCGGAAATTAAAGGCGATATTACCTTCCGTAA
 AsnSerProThrGluSerTyrGlnGlyLysLeuAlaLeuProGluIleLysGlyAspIleThrPheArgAsn

TATACGCTTCCGCTACAAACCGGATGCGCCGGTGATTTTAAATGATGTGAATTTATCGATTCAGCAAGGTGA
 IleArgPheArgTyrLysProAspAlaProValIleLeuAsnAspValAsnLeuSerIleGlnGlnGlyGlu

AGTGATCGGTATCGTAGGACGTTCAGGCTCAGGGAAGAGCACCTTAACGAAATTAATTCAACGTTTTTATAT
 ValIleGlyIleValGlyArgSerGlySerGlyLysSerThrLeuThrLysLeuIleGlnArgPheTyrIle

TCCGGAAAACGGTCAGGTATTAATAGATGGGCATGATTTAGCATTGGCGGATCCGAACTGGCTACGTCGTCA
 ProGluAsnGlyGlnValLeuIleAspGlyHisAspLeuAlaLeuAlaAspProAsnTrpLeuArgArgGln
FIG. 1D
```

```
AGTCGGGGTGGTATTACAAGATAACGTACTATTAAATCGTAGTATTCGAGATAATATTGCCTTAGCGGATCC
 ValGlyValValLeuGlnAspAsnValLeuLeuAsnArgSerIleArgAspAsnIleAlaLeuAlaAspPro

GGGTATGCCAATGGAAAAAATTGTCCATGCGGCAAAATTAGCCGGCGCACATGAATTTATTTCTGAATTGCG
 GlyMETProMETGluLysIleValHisAlaAlaLysLeuAlaGlyAlaHisGluPheIleSerGluLeuArg

TGAGGGATATAACACGATTGTTGGTGAGCAAGGTGCGGGGCTATCTGGCGGGCAACGCCAACGTATTGCGAT
 GluGlyTyrAsnThrIleValGlyGluGlnGlyAlaGlyLeuSerGlyGlyGlnArgGlnArgIleAlaIle

TGCACGCGCTTTGGTGAATAACCCGAAAATCTTAATTTTTGATGAAGCGACCAGCGCATTAGATTATGAATC
 AlaArgAlaLeuValAsnAsnProLysIleLeuIlePheAspGluAlaThrSerAlaLeuAspTyrGluSer

CGAGCATATCATCATGCGCAATATGCACCAGATTTGTAAAGGGAGAACGGTAATTATCATTGCACACCGTTT
 GluHisIleIleMETArgAsnMETHisGlnIleCysLysGlyArgThrValIleIleIleAlaHisArgLeu

ATCTACGGTAAAAAATGCCGACCGTATTATTGTGATGGAAAAAGGTCAGATTGTGGAACAAGGTAAGCATAA
 SerThrValLysAsnAlaAspArgIleIleValMETGluLysGlyGlnIleValGluGlnGlyLysHisLys

AGAGCTGCTTGCTGATCCAAACGGCTTATATCACTACTTACACCAATTACAATCGGAATAGGAGGACTTATG
 GluLeuLeuAlaAspProAsnGlyLeuTyrHisTyrLeuHisGlnLeuGlnSerGlu  ClyI D  MET

AAAACATGGCTAATGGGTTTATATGAGTTTTTCCAACGCTATAAAACGGTTTGGACGGAGATCTGGAAAATT
 LysThrTrpLeuMETGlyLeuTyrGluPhePheGlnArgTyrLysThrValTrpThrGluIleTrpLysIle

CGTCATCAATTGGATACGCCGGATCGAGAAAAGGATGAAAATGAATTTTTACCTGCACACTTAGAGCTGATT
 ArgHisGlnLeuAspThrProAspArgGluLysAspGluAsnGluPheLeuProAlaHisLeuGluLeuIle

GAAACACCGGTGTCAAAAAAACCGAGATTGATCGCTTATTTAATTATGCTGTTCCTATTTTTGGCATTAGTT
 GluThrProValSerLysLysProArgLeuIleAlaTyrLeuIleMETLeuPheLeuPheLeuAlaLeuVal

ATTTCAATTGTCAGTCACGTAGAAATTGTGGCGACCGCAACGGGTAAATTAGCGTTTAGCGACCGTAGCAAA
 IleSerIleValSerHisValGluIleValAlaThrAlaThrGlyLysLeuAlaPheSerAspArgSerLys

GAAATTAAGCCGATTGAAAACGCCTTGGTTAAAGAAATCTTTGTGCAAGACGGACAATTTGTTGAGAAAGAT
 GluIleLysProIleGluAsnAlaLeuValLysGluIlePheValGlnAspGlyGlnPheValGluLysAsp

CAGTTGCTGTTACACTTGACCGCATTGGGAGCCGATGCGGATCAACAAAAAACCAAAAGTTCGTTATCGCTG
 GlnLeuLeuLeuHisLeuThrAlaLeuGlyAlaAspAlaAspGlnGlnLysThrLysSerSerLeuSerLeu

ACTAAATTGGAACGTTATCGTTATGAAATTTTATTAGAGGCGGTTGCGGCGGATAGGTTGCCGCTCATTGAA
 ThrLysLeuGluArgTyrArgTyrGluIleLeuLeuGluAlaValAlaAlaAspArgLeuProLeuIleGlu

CTGACAAAGGATGAATTTAAACATGCTACGGAAGAAGATAAAACCAGAATTCGCTATTTGATCACCGAGCAA
 LeuThrLysAspGluPheLysHisAlaThrGluGluAspLysThrArgIleArgTyrLeuIleThrGluGln

TTTGAAGCTTGGCAAAAGCAAAAGTATCAAAAAGAATTAGCTTTGCAACGTAGAGAAGCAGAAAAACAAACG
 PheGluAlaTrpGlnLysGlnLysTyrGlnLysGluLeuAlaLeuGlnArgArgGluAlaGluLysGlnThr

GTTCTAGCTAATATTCGTAAATATGAGGGAATCAGTCGAGTTGAAAATGAAAGATTAAAAGATCTTAAAAAA
 ValLeuAlaAsnIleArgLysTyrGluGlyIleSerArgValGluAsnGluArgLeuLysAspLeuLysLys

TTATTTAATTCGAAATCGACTTCTAAACATGATGTCTTGACTCAAGAAAATCGTCATATCGAAGCGGTAAAT
 LeuPheAsnSerLysSerThrSerLysHisAspValLeuThrGlnGluAsnArgHisIleGluAlaValAsn

GAGTTGGCGGTGTATAAATCTCGGTTGAATGAAGTGGAAAGTGACTTACGTCAAGCCAAAGAGGAAATACAT
 GluLeuAlaValTyrLysSerArgLeuAsnGluValGluSerAspLeuArgGlnAlaLysGluGluIleHis
```

FIG. 1E

```
TTAATAACTCAGTTGTTTAGAGCCGATATTCTGGAGAAGTTGAAACAAAATGTTGAAGCGGAGAAACAGCTT
LeuIleThrGlnLeuPheArgAlaAspIleLeuGluLysLeuLysGlnAsnValGluAlaGluLysGlnLeu

TCGCTCGAATTAGAAAAAAATGAGCAGCGTCAAATTGCTTCGGTGATTCGTGCGCCGGTTTCCGGTACGGTT
SerLeuGluLeuGluLysAsnGluGlnArgGlnIleAlaSerValIleArgAlaProValSerGlyThrVal

CAGCAACTTAAAACCCATACGGTAGGCGGCGTCGTGACGACTGCCGAAACCTTGATGGTAATTGCTCCGGAA
GlnGlnLeuLysThrHisThrValGlyGlyValValThrThrAlaGluThrLeuMETValIleAlaProGlu

GATGATGTTTTAGAGGTAACGGCGTTAATTCAAAATAAGGATATCGGTTTTATCGAGGTCGGTCAGGATGCG
AspAspValLeuGluValThrAlaLeuIleGlnAsnLysAspIleGlyPheIleGluValGlyGlnAspAla

GTGATTAAAGTAGAAACTTTTCCTTATACTCGTTACGGCTATTTAATGGGTAAAGTAAAAAATATCACGCTG
ValIleLysValGluThrPheProTyrThrArgTyrGlyTyrLeuMETGlyLysValLysAsnIleThrLeu

GAAGCCATCGAACATCCGCAACTCGGTCTAGTTTTTAACTCGATTATTTCTATTGATAGAAAAACTTTATCC
GluAlaIleGluHisProGlnLeuGlyLeuValPheAsnSerIleIleSerIleAspArgLysThrLeuSer

GGCAAAGACGGCAAAGAAATTGAACTTGGATCAGGTATGAGTGTGACGGCGGAAATTAAAACTGGAGAACGT
GlyLysAspGlyLysGluIleGluLeuGlySerGlyMETSerValThrAlaGluIleLysThrGlyGluArg

AGCGTTATTAGTTATTTACTCAGTCCGTTGGAAGAATCCGTTTCGGAGAGTTTAAGAGAACGCTAAAGCAGA
SerValIleSerTyrLeuLeuSerProLeuGluGluSerValSerGluSerLeuArgGluArg---

TAAAACAAGCGGCCATATTTTCTTACTTTTTTGCAAAAAACGTATGAAATATGACCGCTTGTCGTTTGTAAA

AGACTATTTATTTACAATAATTTTAGCACCGTTAGAAAATACGATCTGACGAGCTTCAAATTGAGCGGAGAG

CTGTGCTTGCGGGTTTAGAAATACGGCTTGTGCTTCTTGCGGTAAGTCTGAAACCGGTACGCAAAGGCAAGT

TCCGCCGTGGTTTGGCGTTTTAAGTTATCTTTAAAGGTAACGGGCGCATCTTGCGTGAGGATAACTTTATCA

TTGTAAACATAGTTTACCGCCCATTGAACGATACGAATATTGCGTTTGGTTTTATTTTCAATACTGTATTTA

AAGCTAACCATCGGCTGCCCTTCTTTATTTTTAGCCAATTCATAACCGAAAAAACGTAACCCGATACTGTCA

TTAAATTGTTTAAGGCGTTTTTCTTTAGCCGAAAGAGGTGCATTTTTCGTTACTGATTTATGTTCAACCGTC

GGTTGAATTTTATTGCCTTCAGCTTGAGCATTAAACGCTAAAAAGAATGATGCTACCGCCGTGCTAAGTAAT

TTAATGTGTTTCATAATTCACCTCGTAATGAGAGCTAAAAGCCGACTTGATATATTACGCTATATATTGTCA

GATTTACGGCACAGTTGCAATGACCGCATAACCGTCCGATTCGGCAATAATCTCGACTTGGCTTTCCGCCGC

AATGAAAATCGCTTCGCCTTGTTGGAGATAAATGGACTCTTCACCGAGGTCGATATAGATACTGCCTTTCAT

CACCAATAAGATACTTGCACAGTCGGCCGTAAAGTTTTCTTCGTCAAATGCGTTGAATTGCATATGTTGCAA

TGCAAAATCTTTCGCTTCAGGCGTCGGATAAAGATGAATGAAACCGTCGTTTTCTTGATAAGGCGGAATAAC

TTCGGGGTAATCGGGCGA
```

FIG. 1F

```
CTTAACCATTACAGAACGTTGGTACAAAAAATTTTACAGGAAAATGATGGATAGTCCTTAACAAAAATTAAT

GTTTTATTTCCTATAAAACATCCGACCAGTATTATTTTTTGATTAAAAAAAGAACAAACAGATCATGACAAAC

GTTTGCCTTGTTTTCCTTCACAAAAATATTATGGTTTTTTATTTAGAATAAATTATCTATATTCATTTTTTA

GGGAATGGGAGGGATGATGCTAAAAAATGATTTTAACGTATTGGGACAAATTGCTTGGTTATGGGCAAATTC
ClyII C        METLeuLysAsnAspPheAsnValLeuGlyGlnIleAlaTrpLeuTrpAlaAsnSer

TCCAATGCACCGAAATTGGTCAGTTTCACTGTTAATGAAGAATGTTATTCCTGCAATTGAAAATGACCAATA
 ProMETHisArgAsnTrpSerValSerLeuLeuMETLysAsnValIleProAlaIleGluAsnAspGlnTyr

TTTGTTACTAGTTGATGATGGTTTTCCTATTGCATATTGCAGTTGGGCCAAATTAACTCTAGAGAGTGAGGC
 LeuLeuLeuValAspAspGlyPheProIleAlaTyrCysSerTrpAlaLysLeuThrLeuGluSerGluAla

TCGCTATGTAAAGGACACCAATTCATTAAAAAATAGATGATTGGAATGCAGGAGATCGTATATGGATCATTGA
 ArgTyrValLysAspThrAsnSerLeuLysIleAspAspTrpAsnAlaGlyAspArgIleTrpIleIleAsp

TTGGATTGCCCCATTCGGGGATTCATCTCTATTGTATAAACATATGAGACAACGTTTTCCATACGATATTGG
 TrpIleAlaProPheGlyAspSerSerLeuLeuTyrLysHisMETArgGlnArgPheProTyrAspIleGly

AAGGGCAATTAGAATCTATCCTAGCAAAAAAGATACTGGAAAAATCATATATTTAAAAGGAGGAAAAATAAC
 ArgAlaIleArgIleTyrProSerLysLysAspThrGlyLysIleIleTyrLeuLysGlyGlyLysIleThr

AAAAAAAGTAGCTGAAAAGACATTTCTTCAGTATGAGCAAGAGTTAATAACAGCTCTACAATAATATCTTTA
 LysLysValAlaGluLysThrPheLeuGlnTyrGluGlnGluLeuIleThrAlaLeuGln---

AATGATCAATTATATAAAGGAGACTCTTTTATGTCAAAAATCACTTTGTCATCATTAAAATCGTCCTTACAA
ClyII A                         METSerLysIleThrLeuSerSerLeuLysSerSerLeuGln

CAAGGATTGAAAAATGGGAAAAACAAGTTAAATCAAGCAGGTACAACACTGAAGAATGGTTTAACTCAAACT
GlnGlyLeuLysAsnGlyLysAsnLysLeuAsnGlnAlaGlyThrThrLeuLysAsnGlyLeuThrGlnThr

GGTCATTCTCTACAGAATGGGGCTAAAAAATTAATCTTATATATTCCTCAAGGCTATGATTCGGGTCAAGGA
GlyHisSerLeuGlnAsnGlyAlaLysLysLeuIleLeuTyrIleProGlnGlyTyrAspSerGlyGlnGly

AATGGAGTTCAAGATTTAGTTAAAGCTGCTAATGATTTAGGTATTGAAGTATGGCGAGAAGAACGCAGCAAT
AsnGlyValGlnAspLeuValLysAlaAlaAsnAspLeuGlyIleGluValTrpArgGluGluArgSerAsn

TTGGACATTGCAAAAACTAGCTTTGATACAACTCAGAAAATTCTAGGTTTTACTGATAGAGGAATTGTATTA
LeuAspIleAlaLysThrSerPheAspThrThrGlnLysIleLeuGlyPheThrAspArgGlyIleValLeu

TTTGCACCTCAGCTAGATAATTTATTAAAGAAGAATCCTAAAATTGGCAATACATTAGGAAGTGCTTCTAGC
PheAlaProGlnLeuAspAsnLeuLeuLysLysAsnProLysIleGlyAsnThrLeuGlySerAlaSerSer

ATCTCACAAAATATAGGTAAAGCCAATACTGTATTAGGTGGTATTCAATCTATTTTAGGATCTGTTTTATCT
IleSerGlnAsnIleGlyLysAlaAsnThrValLeuGlyGlyIleGlnSerIleLeuGlySerValLeuSer

GGAGTAAATCTGAATGAATTACTTCAAAATAAAGATCCTAATCAATTAGAACTTGCAAAAGCAGGGCTAGAA
GlyValAsnLeuAsnGluLeuLeuGlnAsnLysAspProAsnGlnLeuGluLeuAlaLysAlaGlyLeuGlu

CTGACTAATGAATTAGTTGGTAATATTGCTAGCTCGGTGCAAACTGTAGATGCATTTGCAGAACAAATATCT
LeuThrAsnGluLeuValGlyAsnIleAlaSerSerValGlnThrValAspAlaPheAlaGluGlnIleSer

AAACTAGGTTCACATTTACAGAATGTGAAAGGATTAGGAGGATTGAGTAATAAATTACAAAATCTACCAGAT
LysLeuGlySerHisLeuGlnAsnValLysGlyLeuGlyGlyLeuSerAsnLysLeuGlnAsnLeuProAsp
```

FIG. 2A

```
CTAGGAAAAGCAAGTTTAGGTTTGGACATTATCTCTGGTTTACTTTCTGGAGCATCTGCAGGTCTCATTTTA
LeuGlyLysAlaSerLeuGlyLeuAspIleIleSerGlyLeuLeuSerGlyAlaSerAlaGlyLeuIleLeu

GCAGATAAAGAGGCTTCAACAGAAAAGAAAGCTGCCGCAGGTGTAGAATTTGCTAACCAAATTATAGGTAAT
AlaAspLysGluAlaSerThrGluLysLysAlaAlaAlaGlyValGluPheAlaAsnGlnIleIleGlyAsn

GTAACAAAAGCGGTCTCATCTTACATTCTTGCCCAACGAGTCGCTTCAGGTTTGTCTTCAACTGGTCCTGTC
ValThrLysAlaValSerSerTyrIleLeuAlaGlnArgValAlaSerGlyLeuSerSerThrGlyProVal

GCTGCATTAATCGCATCTACAGTTGCACTAGCTGTTAGCCCTCTTTCATTCTTAAATGTAGCTGATAAGTTT
AlaAlaLeuIleAlaSerThrValAlaLeuAlaValSerProLeuSerPheLeuAsnValAlaAspLysPhe

AAACAAGCTGATTTAATCAAATCATATTCTGAACGCTTCCAAAAATTAGGATATGATGGAGATCGTTTATTA
LysGlnAlaAspLeuIleLysSerTyrSerGluArgPheGlnLysLeuGlyTyrAspGlyAspArgLeuLeu

GCTGATTTTCACCGTGAGACAGGAACTATTGATGCTTCTGTAACAACAATTAACACTGCTTTAGCAGCTATC
AlaAspPheHisArgGluThrGlyThrIleAspAlaSerValThrThrIleAsnThrAlaLeuAlaAlaIle

TCCGGTGGAGTTGGAGCTGCAAGCGCGGGTTCTCTAGTCGGAGCTCCAGTTGCGTTACTCGTTGCTGGTGTT
SerGlyGlyValGlyAlaAlaSerAlaGlySerLeuValGlyAlaProValAlaLeuLeuValAlaGlyVal

ACGGGACTTATTACAACTATTCTAGAATATTCTAAACAAGCCATGTTTGAACATGTTGCAAATAAGGTTCAT
ThrGlyLeuIleThrThrIleLeuGluTyrSerLysGlnAlaMETPheGluHisValAlaAsnLysValHis

GACAGAATAGTTGAATGGGAGAAAAAACATAATAAAAACTATTTTGAGCAAGGTTATGATTCTCGTCATTTA
AspArgIleValGluTrpGluLysLysHisAsnLysAsnTyrPheGluGlnGlyTyrAspSerArgHisLeu

GCTGATTTACAAGACAATATGAAGTTTCTTATCAATTTAAATAAAGAACTTCAGGCTGAACGCGTAGTAGCT
AlaAspLeuGlnAspAsnMETLysPheLeuIleAsnLeuAsnLysGluLeuGlnAlaGluArgValValAla

ATTACCCAACAAAGATGGGATAACCAAATTGGAGACCTAGCGGCAATTAGCCGTAGAACGGATAAAATTTCC
IleThrGlnGlnArgTrpAspAsnGlnIleGlyAspLeuAlaAlaIleSerArgArgThrAspLysIleSer

AGTGGAAAAGCTTATGTGGATGCTTTTGAGGAGGGGCAACACCAGTCCTACGATTCATCCGTACAGCTAGAT
SerGlyLysAlaTyrValAspAlaPheGluGluGlyGlnHisGlnSerTyrAspSerSerValGlnLeuAsp

AACAAAAACGGTATTATTAATATTAGTAATACAAATAGAAAGACACAAAGTGTTTTATTCAGAACTCCATTA
AsnLysAsnGlyIleIleAsnIleSerAsnThrAsnArgLysThrGlnSerValLeuPheArgThrProLeu

CTAACTCCAGGTGAAGAGAATCGGGAACGTATTCAGGAAGGTAAAAATTCTTATATTACAAAATTACATATA
LeuThrProGlyGluGluAsnArgGluArgIleGlnGluGlyLysAsnSerTyrIleThrLysLeuHisIle

CAAAGAGTTGACAGTTGGACTGTAACAGATGGTGATGCTAGCTCAAGCGTAGATTTCACTAATGTAGTACAA
GlnArgValAspSerTrpThrValThrAspGlyAspAlaSerSerSerValAspPheThrAsnValValGln

CGAATCGCTGTGAAATTTGATGATGCAGGTAACATTATAGAATCTAAAGATACTAAAATTATCGCAAATTTA
ArgIleAlaValLysPheAspAspAlaGlyAsnIleIleGluSerLysAspThrLysIleIleAlaAsnLeu

GGTGCTGGTAACGATAATGTATTTGTTGGGTCAAGTACTACCGTTATTGATGGCGGGGACGGACATGATCGA
GlyAlaGlyAsnAspAsnValPheValGlySerSerThrThrValIleAspGlyGlyAspGlyHisAspArg

GTTCACTACAGTAGAGGAGAATATGGCGCATTAGTTATTGATGCTACAGCCGAGACAGAAAAAGGCTCATAT
ValHisTyrSerArgGlyGluTyrGlyAlaLeuValIleAspAlaThrAlaGluThrGluLysGlySerTyr

TCAGTAAAACGCTATGTCGGAGACAGTAAAGCATTACATGAAACAATTGCCACCCACCAAACAAATGTTGGT
SerValLysArgTyrValGlyAspSerLysAlaLeuHisGluThrIleAlaThrHisGlnThrAsnValGly
```

FIG. 2B

```
AATCGTGAAGAAAAAATTGAATATCGTCGTGAAGATGATCGTTTTCATACTGGTTATACTGTGACGGACTCA
AsnArgGluGluLysIleGluTyrArgArgGluAspAspArgPheHisThrGlyTyrThrValThrAspSer

CTCAAATCAGTTGAAGAGATCATTGGTTCACAATTTAATGATATTTTCAAAGGAAGCCAATTTGATGATGTG
LeuLysSerValGluGluIleIleGlySerGlnPheAsnAspIlePheLysGlySerGlnPheAspAspVal

TTCCATGGTGGTAATGGTGTAGACACTATTGATGGTAACGATGGTGACGATCATTTATTTGGTGGCGCAGGC
PheHisGlyGlyAsnGlyValAspThrIleAspGlyAsnAspGlyAspAspHisLeuPheGlyGlyAlaGly

GATGATGTTATCGATGGAGGAAACGGTAACAATTTCCTTGTTGGAGGAACCGGTAATGATATTATCTCGGGA
AspAspValIleAspGlyGlyAsnGlyAsnAsnPheLeuValGlyGlyThrGlyAsnAspIleIleSerGly

GGTAAAGATAATGATATTTATGTCCATAAAACAGGCGATGGAAATGATTCTATTACAGACTCTGGCGGACAA
GlyLysAspAsnAspIleTyrValHisLysThrGlyAspGlyAsnAspSerIleThrAspSerGlyGlyGln

GATAAACTGGCATTTTCGGATGTAAATCTTAAAGACCTCACCTTTAAGAAAGTAGATTCTTCTCTCGAAATC
AspLysLeuAlaPheSerAspValAsnLeuLysAspLeuThrPheLysLysValAspSerSerLeuGluIle

ATTAATCAAAAAGGAGAAAAAGTTCGTATTGGGAATTGGTTCTTAGAAGATGATTTGGCTAGCACAGTTGCT
IleAsnGlnLysGlyGluLysValArgIleGlyAsnTrpPheLeuGluAspAspLeuAlaSerThrValAla

AACTATAAAGCTACGAATGACCGAAAAATTGAGGAAATTATTGGTAAAGGAGGAGAACGTATTACATCAGAA
AsnTyrLysAlaThrAsnAspArgLysIleGluGluIleIleGlyLysGlyGlyGluArgIleThrSerGlu

CAAGTTGATAAACTGATTAAGGAGGGTAACAATCAAATCTCTGCAGAAGCATTATCCAAAGTTGTGAATGAT
GlnValAspLysLeuIleLysGluGlyAsnAsnGlnIleSerAlaGluAlaLeuSerLysValValAsnAsp

TACAATACGAGTAAAGATAGACAGAACGTATCTAATAGCTTAGCAAAATTGATTTCTTCAGTCGGGAGCTTT
TyrAsnThrSerLysAspArgGlnAsnValSerAsnSerLeuAlaLysLeuIleSerSerValGlySerPhe

ACGTCTTCCTCAGACTTTAGGAATAATTTAGGAACATATGTTCCTTCATCAATAGATGTCTCGAATAATATT
ThrSerSerSerAspPheArgAsnAsnLeuGlyThrTyrValProSerSerIleAspValSerAsnAsnIle

CAATTAGCTAGAGCCGCTTAATATTCAAATCATAGCAATCCTATGGTGTAAATTATAGGATTGTTATTTTTT
GlnLeuAlaArgAlaAla---

TAAAGGAGAAGTTATGGAACCCAATAAAAATAAGGATCTTGGTTTAGCTGTAGAAAATCAAACCTAATCTGA

CAGTTCCCGTTTAAAATTACCGTGTCTGTCAGATTAATTTGAGCTTAAATTCTTTTCTGCCCAAATCCGTTT

TCCATCAAGTAATGTTGCCATCGGTGTTCTGCCACAGCACACTTTTCCTTGATGTGTTCGATGGTGATTATA

ATACATTCATCTAAATCAGCTTGTAATGTCGCTAAATCCGTATATATTTTCTTCCTAAATGCGACTTGGTAA

AATTCTTGTAAGATAGTCTTATGAAAACGTTCACAGATACCATTCGTCTGTGGATGCTTCACTTTCGTTTTA

GTATGCTCTATGTCATTTATCGCTAAATAAAGCTCATAATCGTGATTTTCCACTTTGCCACAATATTCACTG

CCACGGTCGGTGAGAATACGCAACATCGGTAATCCTTGGGCTTCAAAGAACGGCAGTACTTTATGATTGAGC

ATATCTGCAGCGGCAATTGCGGTTTTCATTGTGTAGAGCTTTGCAAAAGCAACCTTACTATAAGTATCAACA

AATGTTTGCTGATAAATGCGTCCAACACCTTTTAAATTACCTACATAAAAGGTATCTTGTGAACCTAAATAG

CCCGGATGAGCGGTTTCAATTTCTCCACTCGATATATCATCCTCTTTCTTACGTTCTAGGGCTTGGACTTGA
```

FIG. 2C

CTTTCATTTAGAATAATGCCTTTCTCAGCCACTTCTTTCTCTAGTGCATTTAAACGCTGTTTAAAGTTAGTA

AGATTATGACGTAGCCAAATGGAACGAACACCACCGGCTGAAACAAACACACCTTGCTTGCGAAGTTCGTTA

CTCACTCGAACTTGTCCGTAAGCTGGAAAATCTAGAGCAAATTTTACAACAGCTTGCTCAATGTGCTCGTCT

ACTCGATTTTTGATATTCGGTACCCGACGAGTTTGCTTAAGTAATGCTTCAACACCGCCTTGCGCTACGGCT

FIG. 2D

GTAGATATTCTTTTAATATCAAACAACTATTGTTATTTGTCTGAGTGTAGATATGTAGCATTGTGTATTTCT

TTATTTACAACTCTAATCTTAATCTAAAAAGATTTCTATATTTTCTTTGTAAGAAATTTTGTTAAAATCCGA

CTAACTATATAATTAACGGTTCTTAAAGTGGATAAATAATAAAATTATGAGTTATAAAAATGTTAAAAATTT

AACAGATGATTTTACAACTTTAGGGCATATCGCTTGGTTGTGGGCTAATTCTCCGTTACATAAGGAGTGGTC

TATCTCTTTGTTTACTTAAGAATATTTTGCCAGCCATTCAACATGATCAATATATTTTACTTATGCGAGATG

AGTTCCCTGTAGCGTTTTGTAGTTGGGCAAATTTAACGTTAACTAATGAAGTGAAGTATGTACGTGATGTGA

CGTCATTGACTTTTGAAGATTGGAATTCAGGAGAACGAAAATGGTTGATCGACTGGATTGCGCCATTTGGGG

ATAACAATACGCTTTATAGATATATGCGTAAAAAATTTCCTAATGAAGTATTCCGGGCCATTCGAGTATATC

CTGGTTCTACAGAAGCGAAAATCATTCATGTTCAAGGAGGACAAATTAATAAATTTACAGCTAAAAAATTAA

TACAACAATATCAGGAAGAACTTATTCAAGTTCTTAACAATCACAAAAAAATTGTAAGAGGATAAAATATGA
<u>ClyIII A</u>                                                                    METSer

GTACTTGGTCAAGCATGTTAGCCGACTTAAAAAAACGGGCTGAAGAAGCCAAAAGACAAGCCAAAAAAGGCT
  ThrTrpSerSerMETLeuAlaAspLeuLysLysArgAlaGluGluAlaLysArgGlnAlaLysLysGlyTyr

ACGATGTAACTAAAAATGGTTTGCAATATGGGGTGAGTCAAGCAAAATTACAAGCATTAGCAGCTGGTAAAG
  AspValThrLysAsnGlyLeuGlnTyrGlyValSerGlnAlaLysLeuGlnAlaLeuAlaAlaGlyLysAla

CCGTTCAAAAGTACGGTAATAAATTAGTTTTAGTTATTCCAAAAGAGTATGACGGAAGTGTTGGTAACGGTT
  ValGlnLysTyrGlyAsnLysLeuValLeuValIleProLysGluTyrAspGlySerValGlyAsnGlyPhe

TCTTTGATTTAGTAAAAGCAGCTGAGGAATTAGGCATTCAAGTTAAATATGTTAACCGTAATGAATTGGAAG
  PheAspLeuValLysAlaAlaGluGluLeuGlyIleGlnValLysTyrValAsnArgAsnGluLeuGluVal

TTGCCCATAAAAGTTTAGGTACCGCAGACCAATTCTTGGGTTTAACAGAACGTGGACTTACTTTATTTGCAC
  AlaHisLysSerLeuGlyThrAlaAspGlnPheLeuGlyLeuThrGluArgGlyLeuThrLeuPheAlaPro

CGCAACTAGATCAGTTCTTACAAAAACATTCAAAAATTTCTAACGTAGTGGGCAGTTCTACTGGTGATGCAG
  GlnLeuAspGlnPheLeuGlnLysHisSerLysIleSerAsnValValGlySerSerThrGlyAspAlaVal

TAAGTAAACTTGCTAAGAGTCAAACTATTATTTCAGGAATTCAATCTGTATTAGGTACTGTATTAGCAGGTA
  SerLysLeuAlaLysSerGlnThrIleIleSerGlyIleGlnSerValLeuGlyThrValLeuAlaGlyIle

TTAATCTTAATGAAGCTATTATTAGTGGCGGTTCAGAGCTCGAATTAGCTGAAGCTGGTGTTTCTTTAGCCT
  AsnLeuAsnGluAlaIleIleSerGlyGlySerGluLeuGluLeuAlaGluAlaGlyValSerLeuAlaSer

CTGAGCTGCTTAGTAATATTGCTAAAGGTACAACAACAATAGATGCTTTCACTACACAAATCCAGAACTTTG
  GluLeuLeuSerAsnIleAlaLysGlyThrThrThrIleAspAlaPheThrThrGlnIleGlnAsnPheGly

GGAAATTAGTGGAAAATGCTAAAGGGTTAGGTGGTGTTGGCCGCCAATTACAGAATATTTCAGGTTCTGCAT
  LysLeuValGluAsnAlaLysGlyLeuGlyGlyValGlyArgGlnLeuGlnAsnIleSerGlySerAlaLeu

TAAGCAAAACTGGATTAGGTTTGGATATTATCTCAAGCTTACTTTCAGGAGTAACTGCAAGTTTTGCTTTAG
  SerLysThrGlyLeuGlyLeuAspIleIleSerSerLeuLeuSerGlyValThrAlaSerPheAlaLeuAla

CGAATAAGAATGCTTCAACAAGCACTAAAGTTGCTGCTGGCTTTGAACTCTCAAATCAAGTAATTGGTGGTA
  AsnLysAsnAlaSerThrSerThrLysValAlaAlaGlyPheGluLeuSerAsnGlnValIleGlyGlyIle

FIG. 3A

```
TTACGAAAGCAGTATCAAGCTATATTCTTGCACAGCGTTTAGCTGCTGGTTTATCTTCGACAGGTCCTGCTG
  ThrLysAlaValSerSerTyrIleLeuAlaGlnArgLeuAlaAlaGlyLeuSerSerThrGlyProAlaAla

CAGCACTAATTGCGTCTAGTATTTCTTTAGCAATCAGTCCATTGGCGTTTTTACGTGTAGCTGATAATTTTA
  AlaLeuIleAlaSerSerIleSerLeuAlaIleSerProLeuAlaPheLeuArgValAlaAspAsnPheAsn

ATCGTTCTAAAGAAATTGGCGAATTTGCTGAACGTTTCAAAAAATTGGGCTATGACGGCGATAAACTACTTT
  ArgSerLysGluIleGlyGluPheAlaGluArgPheLysLysLeuGlyTyrAspGlyAspLysLeuLeuSer

CAGAGTTTTATCACGAAGCTGGTACTATTGATGCCTCAATTACTACAATTAGTACAGCACTTTCTGCTATCG
  GluPheTyrHisGluAlaGlyThrIleAspAlaSerIleThrThrIleSerThrAlaLeuSerAlaIleAla

CAGCTGGAACGGCCGCCGCGAGTGCAGGTGCATTAGTTGGCGCACCAATTACTTTGTTGGTTACTGGTATCA
  AlaGlyThrAlaAlaAlaSerAlaGlyAlaLeuValGlyAlaProIleThrLeuLeuValThrGlyIleThr

CAGGATTAATTTCTGGTATTTTAGAGTTCTCTAAACAACCAATGTTAGATCATGTTGCATCGAAAATTGGTA
  GlyLeuIleSerGlyIleLeuGluPheSerLysGlnProMETLeuAspHisValAlaSerLysIleGlyAsn

ACAAAATTGACGAATGGGAGAAAAAATACGGTAAAAATTACTTCGAGAATGGCTATGATGCTCGTCATAAAG
  LysIleAspGluTrpGluLysLysTyrGlyLysAsnTyrPheGluAsnGlyTyrAspAlaArgHisLysAla

CTTTCTTAGAAGATTCATTCTCATTATTGTCTAGTTTTAATAAACAATATGAAACTGAAAGAGCTGTTTTAA
  PheLeuGluAspSerPheSerLeuLeuSerSerPheAsnLysGlnTyrGluThrGluArgAlaValLeuIle

TTACACAACAACGTTGGGATGAATATATTGGCGAACTTGCGGGTATTACTGGCAAAGGTGACAAACTCTCTA
  ThrGlnGlnArgTrpAspGluTyrIleGlyGluLeuAlaGlyIleThrGlyLysGlyAspLysLeuSerSer

GTGGTAAGGCGTATGTAGATTACTTTCAAGAAGGTAAATTATTAGAGAAAAAACCTGATGACTTTAGCAAAG
  GlyLysAlaTyrValAspTyrPheGlnGluGlyLysLeuLeuGluLysLysProAspAspPheSerLysVal

TAGTTTTCGATCCAACTAAGGGCGAAATTGATATTTCAAATAGCCAAACGTCAACGTTGTTAAAATTTGTTA
  ValPheAspProThrLysGlyGluIleAspIleSerAsnSerGlnThrSerThrLeuLeuLysPheValThr

CGCCATTATTAACACCAGGTACAGAGTCACGTGAAAGAACTCAAACAGGTAAATATGAATATATCACGAAGT
  ProLeuLeuThrProGlyThrGluSerArgGluArgThrGlnThrGlyLysTyrGluTyrIleThrLysLeu

TAGTTGTAAAAGGTAAAGATAAATGGGTTGTTAATGGCGTTAAAGATAAAGGTGCCGTTTATGATTATACTA
  ValValLysGlyLysAspLysTrpValValAsnGlyValLysAspLysGlyAlaValTyrAspTyrThrAsn

ATTTAATTCAACATGCTCATATTAGTTCATCAGTAGCACGTGGTGAAGAATACCGTGAAGTTCGTTTGGTAT
  LeuIleGlnHisAlaHisIleSerSerSerValAlaArgGlyGluGluTyrArgGluValArgLeuValSer

CTCATCTAGGCAATGGTAATGACAAAGTGTTCTTAGTCGCGGGTTCCGCAGAAATTCACGCTGGTGAAGGTC
  HisLeuGlyAsnGlyAsnAspLysValPheLeuValAlaGlySerAlaGluIleHisAlaGlyGluGlyHis

ATGATGTGGTTTATTATGATAAAACCGATACAGGTCTTTTAGTAATTGATGGAACCAAAGCGACTGAACAAG
  AspValValTyrTyrAspLysThrAspThrGlyLeuLeuValIleAspGlyThrLysAlaThrGluGlnGly

GGCGTTATTCTGTTACGCGCGAATTGAGTGGTGCTACAAAAATCCTGAGAGAAGTAATAAAAAATCAAAAAT
  ArgTyrSerValThrArgGluLeuSerGlyAlaThrLysIleLeuArgGluValIleLysAsnGlnLysSer

CTGCTGTTGGTAAACGTGAAGAAACCTTGGAATATCGTGATTATGAATTAACGCAATCAGGTAATAGTAACC
  AlaValGlyLysArgGluGluThrLeuGluTyrArgAspTyrGluLeuThrGlnSerGlyAsnSerAsnLeu

TAAAAGCACATGATGAATTACATTCAGTAGAAGAAATTATTGGAAGTAATCAGAGAGACGAATTTAAAGGTA
  LysAlaHisAspGluLeuHisSerValGluGluIleIleGlySerAsnGlnArgAspGluPheLysGlySer
```

FIG. 3B

```
GTAAATTCAGAGATATTTTCCATGGTGCCGATGGTGATGATCTATTAAATGGTAATGATGGGGATGATATTC
 LysPheArgAspIlePheHisGlyAlaAspGlyAspAspLeuLeuAsnGlyAsnAspGlyAspAspIleLeu

TATACGGTGATAAAGGTAACGATGAGTTAAGAGGTGATAATGGTAACGACCAACTTTATGGTGGTGAAGGTA
 TyrGlyAspLysGlyAsnAspGluLeuArgGlyAspAsnGlyAsnAspGlnLeuTyrGlyGlyGluGlyAsn

ATGACAAACTATTAGGAGGTAATGGCAATAATTACCTCAGTGGTGGTGATGGCAATGATGAGCTTCAAGTCT
 AspLysLeuLeuGlyGlyAsnGlyAsnAsnTyrLeuSerGlyGlyAspGlyAsnAspGluLeuGlnValLeu

TAGGCAAATGGTTTTTAATGTGCTTCGTGGCGGTAAAGGCGATGATAAACTTTATGGTAGCTCAGGTTCTGA
 GlyLysTrpPheLeuMETCysPheValAlaValLysAlaMETIleAsnPheMETValAlaGlnValLeuIle

TTTACCTTGATGGTGGAGAAGGTAATGATTATCTAGAAGGAGGCGATGGTAGCGATTTTTATGTTTACTGTT
 TyrLeuAspGlyGlyGluGlyAsnAspTyrLeuGluGlyGlyAspGlySerAspPheTyrValTyrCysSer

CCACTTCAGGTAATCATACTATTTATGATCAAGGTAAATCTAGTGATTTAGATAAACTATATTTGTCTGATT
 ThrSerGlyAsnHisThrIleTyrAspGlnGlyLysSerSerAspLeuAspLysLeuTyrLeuSerAspPhe

TTTCCTTCGATCGTCTTCTTGTTGAGAAAGTTGATGATAACCTTGTACTTAGAAGTAATGAAAGTAGTCATA
 SerPheAspArgLeuLeuValGluLysValAspAspAsnLeuValLeuArgSerAsnGluSerSerHisAsn

ATAATGGAGTACTCACAATCAAAGACTGGTTTAAAGAAGGGAATAAATATAACCATAAAATTGAACAAATTG
 AsnGlyValLeuThrIleLysAspTrpPheLysGluGlyAsnLysTyrAsnHisLysIleGluGlnIleVal

TTGATAAAAATGGTAGAAAATTGACAGCAGAGAATTTAGGAACTTATTTCAAAAATGCTCCAAAAGCTGACA
 AspLysAsnGlyArgLysLeuThrAlaGluAsnLeuGlyThrTyrPheLysAsnAlaProLysAlaAspAsn

ATTTGCTTAATTATGCAACTAAAGAAGATCAGAATGAAAGCAATTTATCTTCACTTAAAACTGAATTAAGTA
 LeuLeuAsnTyrAlaThrLysGluAspGlnAsnGluSerAsnLeuSerSerLeuLysThrGluLeuSerLys

AAATTATTACTAATGCAGGTAATTTTGGTGTGGCAAAACAAGGTAATACTGGAATCAATACAGCTGCCTTGA
 IleIleThrAsnAlaGlyAsnPheGlyValAlaLysGlnGlyAsnThrGlyIleAsnThrAlaAlaLeuAsn

ACAATGAAGTGAATAAAATCATTTCTTCTGCTAATACCTTTGCTACTTCACAATTGGGTGGCTCAGGGATGG
 AsnGluValAsnLysIleIleSerSerAlaAsnThrPheAlaThrSerGlnLeuGlyGlySerGlyMETGly

GAACATTACCATCAACGAATGTAAATTCAATGATGCTAGGTAACCTAGCTAGAGCAGCTTAATCATCTGCAT
 ThrLeuProSerThrAsnValAsnSerMETMETLeuGlyAsnLeuAlaArgAlaAla---

AATCAATAGCAATCCTATGGCTATTCTAGGATTGCTATTTTATTTATGGAGTCACAAATGCCTTTTAACGAA

AAAATAGATTACGGATTACATGCATTGGTAATTCTCGCGCAATATCACAATGTTGCCGTAAACCCTGAAGAG

GTAAAACATAAATTTGATCTTGATGGCAAAGGATTGGATCTTGTTGCTTGGTTATTAGCAGCAAAATCATTA

GAATTAAAAGCCAAACGAGTAAAAAAGAGTATTGAGCGTTTACCATTTATTCATCTTCCTGCTTTAATCTGG

CGAGATGATGGTCAA
```

NUCLEIC ACID ENCODING *ACTINOBACILLUS PLEUROPNEUMONIAE* CYTOLYTIC PROTEINS

This application is a Divisional application under 37 C.F.R.I.62 of prior application Ser. No. 08/138,609, filed Oct. 15, 1993, which is a continuation of Ser. No. 07/722,971 filed Jun. 28, 1991, both now abandoned.

FIELD OF THE INVENTION

The present invention is in the veterinary field. More specifically, the invention relates to the prophylaxis and therapy of pleuropneumonia in pigs.

BACKGROUND OF THE INVENTION

Pleuropneumonia is a major respiratory disease in pigs and causes severe economic losses in pig farming in many countries including the United States and Canada. The disease is caused by the bacterium *Actinobacillus pleuropneumoniae* (previously also referred to as *Haemophilus pleuropneumoniae*) and is considered to be one of the most important disorders of the bronchial tubes in pigs. Frequently, the disease is fatal. *Actinobacillus pleuropneumoniae* is known to exist in twelve infective serotypes.

Since pleuropneumonia can be induced by inoculating pigs with sterile culture supernatants of *A. pleuropneumoniae,* extracellular toxic proteins are assumed to be involved in the development of the pneumonic lesions. There is growing evidence that qualitative or quantitative differences in toxic activities exist between the twelve serotypes of *A. pleuropneumoniae.* Hemolytic and cytotoxic activities have been reviewed by T. A. Bertram, *Can. J. Vet. Res.* 54: 553–556 (1990). Two different hemolytic activities were reported by Frey and Nicolet, *J. Clin. Microbiol.* 28: 232–236 (1990), whereas four antigenically different activities were distinguished by Kamp and Van Leengoed, *J. Clin. Microbiol.* 27: 1187–1191 (1989). Whether such activities are functions of one or more molecules is not known.

Vaccines proposed thus far for preventing infections by *Actinobacillus pleuropneumoniae* are mostly based on whole live cells, attenuated cells, lysates, culture supernatants, or extracts of *A. pleuropneumoniae.* WO-A-80,02113 (or Canadian Patent 1,189,790) teaches a vaccine for controlling pleuropneumonia in pigs, containing *A. pleuropneumoniae* cells, cell fragments etc. and, as an adjuvant, material derived from *Bordetella pertussis.* EP-A-420,743 proposes a vaccine containing inactivated toxin of serotype 1 and optionally an inactivated toxin of another serotype of *A. pleuropneumoniae;* it provides protection against serotype 1 and partial protection against other serotypes. EP-A-354,628 discloses a universal vaccine against *A. pleuropneumoniae,* which contains extracellular proteins from two different serotypes, and is effective against all *A. pleuropneumoniae* serotypes. Although these known vaccines provide protection against some or even all of the field strains of *A. pleuropneumoniae,* the active compounds are not known. As a result, control, verification, and standardisation of vaccines is difficult, since the ratio between active components cannot be optimized and inactive and sometimes adverse components are always present in the vaccines.

SUMMARY OF THE INVENTION

The present invention, in one aspect, provides a vaccine for the prevention and/or the treatment of infection by *Actinobacillus pleuropneumoniae* containing at least an immunogenic part of at least one polypeptide selected from the group consisting of cytolytic proteins of *A. pleuropneumoniae* produced by recombinant DNA technology, and detoxified derivatives thereof.

It has been found according to the invention that *Actinobacillus pleuropneumoniae* produces three hemolytic and/or cytotoxic proteins (toxins), hereinafter referred to as cytolytic proteins: Cytolysins I, II and III (ClyI, ClyII and ClyIII). Where the term "Cytolysin" (Cly) is used in the present specification, this shall thus be understood to comprise any extracellular protein produced by any strain of *A. pleuropneumoniae* and producing any adverse effect (be it hemolytic, cytotoxic or other or both) on cells or tissues of an infected animal; where appropriate it shall be understood also to comprise immunogenically active parts of these proteins or derivatives thereof having diminished adverse effects. Protection against infections by any of the known serotypes of *A. pleuropneumoniae* is conferred to an animal by administering an effective amount of all three cytolysins, and partial or complete protection against specific serotypes is conferred by administering one or two of the cytolysins, depending on the serotype or serotypes in question.

Thus, the vaccine of the invention contains at least one of the three cytolysins I, II and III, preferably two, and more preferably three. The cytolysins may be present in the vaccine as the naturally occurring proteins, or they may be present as derivatives containing at least an immunogenic part of the proteins, or as a detoxified equivalent. Detoxification shall be understood to mean that the toxic activity of the proteins has been removed to a sufficient degree or for a sufficient number of the protein molecules to provide a vaccine which does not produce an unacceptable toxic reaction in the producing host and/or in the vaccinated animal, whereas it provides a sufficient immune response. Detoxification can be brought about by chemical, physical or enzymatic treatment of the proteins or by substitution, insertion or deletion of one or more nucleotides in the cytolysin genes resulting in the substitution, insertion or deletion of one or more amino acids in the protein. Detoxification can also be achieved by expression of the toxin gene in the absence of the activator gene.

It was found that the cytolysins are encoded by operons wherein the structural toxin gene is flanked at the 5' end by a gene encoding a peptide required to activate the toxin, hereinafter referred to as the activator protein. The cytolysins may be present in the vaccine in the activated or non-activated form.

The cytolysins or their derivatives present in the vaccine are preferably obtained by expression of recombinant DNA encoding the proteins mentioned above. The detoxified cytolysins constitute a further embodiment of the present invention.

In another aspect of the invention a process for producing a cytolytic protein of *Actinobacillus pleuropneumoniae* or an immunogenic and/or detoxified derivative thereof is provided, which process comprises the steps of:

a) selecting at least one nucleotide sequence coding for at least an immunogenic part of said cytolytic protein (toxin) optionally including an activator protein, or a derivative thereof;
b) inserting the nucleotide sequence(s) selected in step a) in a vector or an expression vector;
c) transforming a host cell, preferably a host cell that is capable of secreting said cytolytic protein, with the vector obtained in step b);

d) cultivating the host cell of step c) to express the nucleotide sequence(s) of step a);

e) recovering and optionally purifying the protein from the culture;

f) optionally modifying the protein to produce a detoxified protein.

In yet another aspect, the invention is concerned with a process of producing a vaccine wherein at least one, and preferably two, and more preferably three, of the cytolysins or immunogenic parts thereof, thus produced, are combined with an immunologically acceptable carrier and optionally a suitable adjuvant.

The host cell referred to in the process of producing the cytolysins or their derivatives may be a microorganism, preferably a non-pathogenic microorganism capable of expressing at least one nucleotide sequence encoding the cytolysins by having a strong promoter inducing high expression levels or by allowing the introduction of an exogenous promoter system to induce such high expression levels. A suitable host cell is *Escherichia coli.*

In a further aspect, the invention provides a nucleotide sequence encoding at least an immunogenic part of a polypeptide selected from cytolytic proteins of *Actinobacillus pleuropneumoniae* optionally including activator proteins and transport proteins, the latter ones being proteins that assist in the secretion of the cytolytic proteins to the periplasma or the medium. The invention also relates to a system that expresses and secretes said nucleotide sequence and to a vector containing at least one of said nucleotide sequences each one preferably operatively linked to a promoter and optionally an enhancer.

In yet another aspect the invention relates to a host cell containing at least one nucleotide sequence encoding the cytolytic proteins or their derivatives, and capable of expressing them, the nucleotide sequence(s) either being contained as such or as said vector and being either present in the host cell in the genome of the host or as a plasmid. Preferably, the host cell contains nucleotide sequences encoding at least two of the cytolysins, and more preferably it contains the sequences encoding all three cytolysins. The host cell is preferably derived from *E. coli.*

The invention also provides a vaccine for prophylaxis and therapy of infections by *A. pleuropneumoniae* containing a microorganism carrying one or more nucleotide sequences encoding at least an immunogenic part of at least one cytolytic proteins of *A. pleuropneumoniae* or a detoxified derivative thereof. The microorganism may be an attenuated microorganism such as an attenuated virus or a bacterium. Administration of the vaccine results in multiplication of the microorganism and thus in production of the immunogen.

The invention further relates to diagnostic means for detecting infection by *A. pleuropneumoniae.* Specifically, the invention is concerned with an antibody, preferably a monoclonal antibody, raised against one of the native cytolysins and useful as a component of a diagnostic kit for detecting infection by *A. pleuropneumoniae;* antibodies raised against modified cytolysins are useful for determining protection by these modified cotylysins. Antibodies raised against native or modified cytolysins can also be used for passive immunisation of infected animals.

In another aspect, the invention provides a DNA-probe comprising at least a part of a nucleotide sequence encoding a cytolysin of *Actinobacillus pleuropneumoniae* which may be used in a diagnostic method and a diagnostic kit for detecting infection by *A. pleuropneumoniae.* Another method of diagnosing an *A. pleuropneumoniae* infection is to determine the presence of *A. pleuropneumoniae* cytolysins in a subject whereby protein pattern is indicative of the infective serotype or group of serotypes.

BRIEF DESCRIPTION OF THE DRAWINGS

In the appended drawings, which form a part of the present disclosure,

FIGS. 1/A–1/F shows the nucleotide sequence of the cytolysin I gene and its activator gene of *Actinobacillus pleuropneumoniae* serotype 9 (reference strain CVI 13261) and the corresponding sequence of amino acid residues (SEQ ID NO:1:);

FIGS. 2/A–2/D shows the nucleotide sequence of the cytolysin II gene and its activator and transport genes of *Actinobacillus pleuropneumoniae* strain serotype 9 (reference strain CVI 13261), and the corresponding sequence of amino acid residues (SEQ ID NO:2:);

FIGS. 3/A–3/C shows the preliminary nucleotide sequence of the cytolysin III gene of *Actinobacillus pleuropneumoniae* serotype 8 (reference strain CVI 405), and the corresponding sequence of amino acid residues (SEQ ID NO:3:);

Figure 4:
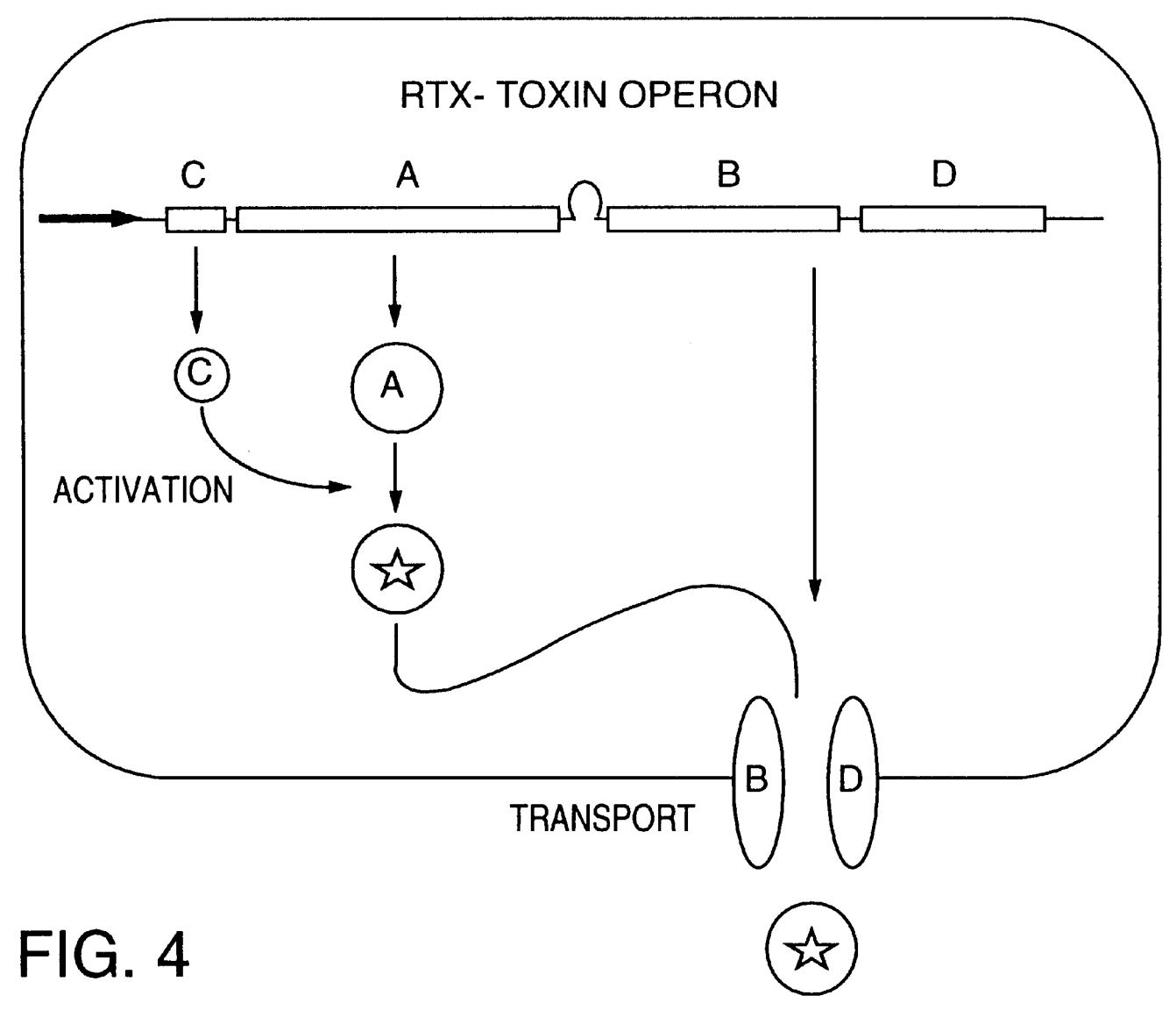

FIG. 4 schematically shows a RTX-toxin operon comprising the toxin gene (A), the activator gene (C), and the transporter genes (B, D) as well as the operation of the gene products thereof;

DETAILED DESCRIPTION OF THE INVENTION

Figure 5:
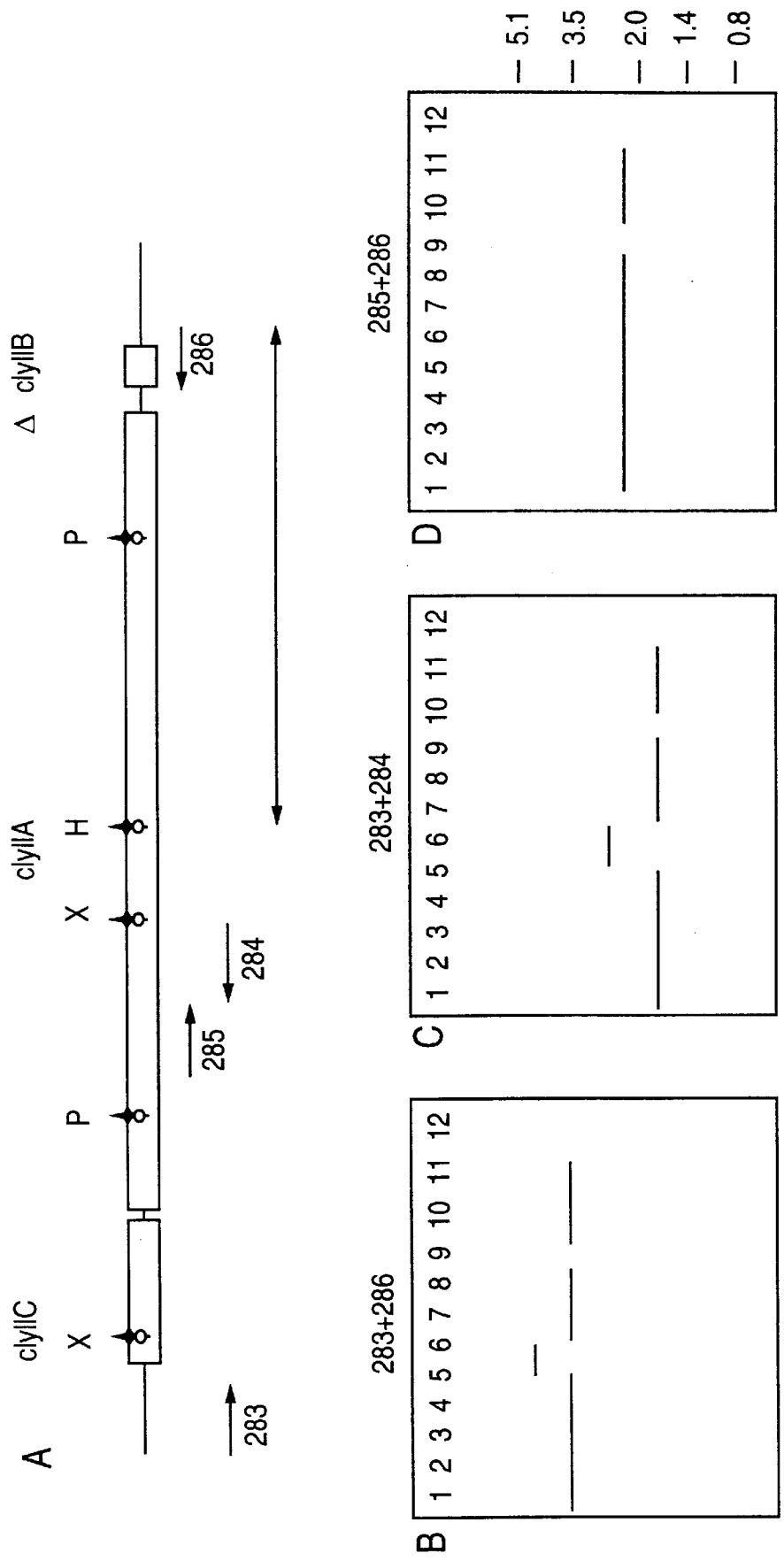
FIGS. 5a–d shows the clyIICA determinant of *A. pleuropneumoniae* serotype 9 and PCR amplification products.

According to the invention it has been found that pathogenesis of *Actinobacillus pleuropneumoniae* infections can be attributed to three extracellular proteins. These proteins have approximate molecular weights of 105,000, 103,000, and 120,000 respectively. The 105,000 and 103,000 dalton proteins are immunologically related to each other. These proteins were found to be excellent tools for providing protection of animals, in particular pigs, against *A. pleuropneumoniae* infections of any serotype. Although factors that were thought to be responsible for the pathogenicity of *A. pleuropneumoniae* were referred to in the prior art as hemolysins and cytotoxins, it has been found now that both cytotoxic and hemolytic activities can result from a single molecule, and hence these proteins are denoted herein as cytolysins (Cly's): the 105 kDa protein as ClyI, the 103 kDa protein as ClyII, and the 120 kDa protein as ClyIII. The nucleotide sequence of the clyI and clyII genes and the preliminary sequence of clyIII is given in FIGS. 1, 2 and 3, respectively.

In FIG. 1 the amino acid sequences of the ClyI C protein (activator), ClyI A protein (cytolytic protein ClyI), ClyI B protein (transport protein), and ClyI D protein (transport protein) are indicated below the nucleotide sequence.

In FIG. 2 the amino acid sequences of the ClyII C protein (activator) and ClyII A protein (cytolytic protein ClyII), are indicated below the nucleotide sequence.

In FIG. 3 the amino acid sequence of the ClyIII A protein (cytolytic protein ClyII) is indicated below the nucleotide sequence.

For the cloning and characterization of the genetic determinants for these proteins three different screening techniques were used: hybridization with an lkt DNA probe, selection for hemolytic activity, and reacion with monoclonal antibodies. On the basis of the reaction pattern with a set of MAbs it was concluded that ClyII is responsible for what has been described by others as HlyII activity (Frey, J., and J. Nicolet (1990) *J. Clin. Microb.* 28: 232–236). ClyI is identical to HlyI. Since we found no differences between the ClyII amino acid sequence of serotype 9 and that of an RTX toxin identified in serotype 5, the latter also must be responsible for HlyII activity and not for HlyI as has been suggested by others (Chang, Y. et al. (1989) *DNA*, 8: 635–647; MacInnes, J. I. et al. (1990) *J. Bacteriol.* 172: 4587–4592). For ClyII we now have shown, for the first time, that both a (weak) hemolytic activity as well as a (moderate) cytotoxic activity are clearly confined in a single protein.

ClyI, ClyII and ClyIII are members of the RTX cytotoxin family. This finding is not only based on immunological data but also on the similarities between primary sequences, hydropathy profiles and the secretion of active toxin by the hlyBD genes of *E. coli*. The sequenced areas of the ClyI, ClyII and ClyIII encoding operons possess all the general characteristics of other RTX toxin operons (cf. Strathdee, C. A., and R. Y. C. Lo. (1989) *J. Bacteriol.* 171: 916–928).

With respect to the genetic organization of the ClyII operon we found a striking difference with other RTX operons. The ClyII operon does not contain secretion genes contiguous to the toxin gene. Sequence alignment studies suggested that in an ancestral clyII operon a recombination event occured at position 3490 thereby disrupting the ancestral clyIIB gene. Intact secretion genes are, however, present elsewhere in the genomes of *A. pleuropneumoniae* serotypes. These secretion genes, however, belong to intact (serotypes 1, 5, 9, 10, 11) or disrupted (serotypes 2, 4, 7, 8, 12) ClyI operons. This is based on sequence data and on the observation that a 7.4 kb NsiI/HindIII DNA fragment covering the clyB gene and approximately 4.5 kb of upstream sequences of serotype 9 encodes a 105 kDa protein indistinguishable from ClyI. This means that the ancestral clyI-IBD genes have been lost from the serotype 9 genome. In addition these data indicate that secretion of both ClyI and ClyII is dependent on only a single set of secretion genes. Since these secretion genes belong to the ClyI operon, these genes are referred to herein as clyIBD. Three extra nucleotides are present in front of clyIBD in a region which forms a rho-independent transcription termination signal in other RTX determinants (cf. Strathdee, C. A., and R. Y. C. Lo. (1989) *J. Bacteriol.* 171: 5955–5962). Furthermore the row of seven T residues which is present in these signals has been changed in clyI to the sequence TTATTT. These nucleotide changes might affect the efficiency of transcription termination or the regulation of this process leading to another level of clyBD expression.

The finding that the primary amino acid sequence of the serotype 9 ClyII is completely identical to the serotype 5 hemolysin and also the finding that (almost) completely identical clyIICA genes are present in serotypes 1, 2, 3, 4, 7, 8, 11 and 12, suggests an important role for ClyII in pathogenesis. The observation that ClyII is produced in all serotypes except serotype 10 and that ClyII is the only extracellular cytolysin of serotypes 6, 7, and 12, supports this view.

The ClyII determinant of the reference strains of all twelve *A. pleuropneumoniae* serotypes were studied and it was demonstrated, by southern hybridization, that clyIICA sequences are present in all serotypes, except 10. This is in agreement with the observation that serotype 10 is the only serotype not secreting ClyII. PCR amplification of the clyICA sequences of the serotypes carrying these genes resulted in equally sized products for all serotypes, except 6. The clyIICA genes of the serotypes 1, 2, 3, 4, 5, 7, 8, 9, 11 and 12, giving equally sized PCR fragments, were compared by extensive RFLP studies. For these studies we used four different restriction enzymes, which together have 57 recognition sites in the clyIICA sequence of serotype 9 and are therefore very suitable for a detailed comparative study. These studies showed very similar restriction patterns of clyIICA for the ten serotypes examined. These results give strong evidence that the clyIICA genes of the serotypes 1, 2, 3, 4, 5, 7, 8, 9, 11 and 12 have a very similar primary structure. Only three differences among the clyIICA genes of the 10 serotypes were found in these RFLP studies, and this low number is illustrative for the high degree of similarity between the clyII genes. Compared to the serotype 9 sequence additional sites were found for Sau3AI in serotype 5 at position −94, and for RsaI in serotype 7 close to position 2818 or 3143. Furthermore a small deletion between position 510 and 690 was found in serotype 8 by HinfII digestion. Sequence comparison of the serotype 5 and 9 clyIICA sequences showed this additional Sau3AI site in serotype 5. From this comparison it was also expected that in serotype 5 an additional HpaII site at position 209, a three basepair deletion at position 51 and a single base-pair deletion at position 44 would be present. No evidence was found either for the additional HpaII site, when analysing the clyIICA fragments of serotype 5 and 9, after digestion with this enzyme, or for the deletions when analyzing the sizes of the restriction fragments generated by AluI, HinfII, RsaI or Sau3AI. The absence of these sequence differences shows that the serotype 5 and 9 clyIICA sequences are even more similar to each other than expected from the published DNA sequences.

Intact transporter genes, clyIIBD, contiguous with the clyIICA genes were not found among the twelve serotypes. Hybridization of the proposed clyIBD sequences of serotype 9 to genomic DNA of the twelve serotypes showed hybridization to all serotypes, excluding 3 and 6. This indicates that all serotypes, but 3 and 6, do contain the clyIBD transporter genes. The translation products of these genes may act in trans and account for the transmembrane transport of ClyII. The transporter proteins for ClyII of serotypes 3 and 6 however remain to be identified. To our knowledge the proposed complementation of the RTX transporter genes of two RTX operons is the first evidence that these transporter genes are exchangeable in a naturally occurring organism.

The fact that most serotypes secrete ClyII, and that serotype 7 and 12 secrete ClyII as the only cytolysin illustrates the role of this toxin in porcine pleuropneumonia. Immunization with ClyII will induce antibodies directed against ClyII of all serotypes. Furthermore, the very similar clyIICA genes may be the targets of choice for diagnosis of *A. pleuropneumoniae* infection, since their sequences are present and highly similar in all serotypes, except serotype 10. There is good evidence that field strains of most, if not all, serotypes produce the same cytolytic activities as the reference strains.

Table A shows the extracellular protein pattern and their hemolytic and cytotoxic activity for the various serotypes of *Actinobacillus pleuropneumoniae*. Table B shows the same protein and activity pattern wherein the immunologically related serotypes are grouped together.

TABLE A

| Serotype | 1 | 2 | 3 | 4 | 5 | 6 | 7 | 8 | 9 | 10 | 11 | 12 |
|---|---|---|---|---|---|---|---|---|---|---|---|---|
| 120 kDa = ClyIII |  | ■ | ■ | ■ |  | ■ |  | ■ |  |  |  |  |
| 105 kDa = ClyI | ■ |  |  |  | ■ |  |  |  | ■ | ■ | ■ |  |
| 103 kDa = ClyII | ■ | ■ | ■ | ■ | ■ | ■ | ■ | ■ | ■ |  | ■ | ■ |
| Hemolytic | S | W | W | W | S | N | W | W | S | S | S | W |
| Cytotoxic | S | S | S | S | S | N | M | S | S | S | S | M |

S = strong activity; M = moderate activity; W = weak activity; N = none ■ = protein band is present

TABLE B

| Serotype | 1 | 5 | 9 | 11 | 2 | 3 | 4 | 8 | 7 | 12 | 10 |
|---|---|---|---|---|---|---|---|---|---|---|---|
| 120 kDa = ClyIII |  |  |  |  | ■ | ■ | ■ | ■ |  |  |  |
| 105 kDa = ClyI | ■ | ■ | ■ | ■ |  |  |  |  |  |  | ■ |
| 103 kDa = ClyII | ■ | ■ | ■ | ■ | ■ | ■ | ■ | ■ | ■ | ■ |  |
| Hemolytic | S | S | S | S | W | W | W | W | W | W | S |
| Cytotoxic | S | S | S | S | S | S | S | S | M | M | S |

S = strong activity; M = moderate activity; W = weak activity; N = none ■ = protein band is present A vaccine containing ClyII or an immunogenic part thereof or a detoxified derivative thereof will provide protection against infections by *Actinobacillus pleuropneumoniae* serotypes 7 and 12, whereas it might provide partial protection against other serotypes except 10. Similarly, a vaccine containing ClyI or an effective part or derivative thereof will provide protection against serotype 10 and partial protection against serotypes 1, 5, 9 and 11, whereas a vaccine containing ClyIII or an effective part or derivative thereof will provide partial protection against serotypes 2, 3, 4, 6 and 8. Further a vaccine containing ClyII and ClyI or effective parts or derivatives thereof will provide protection against infection by serotypes 1, 5, 7, 9, 10, 11 and 12, and partial protection against the other serotypes; a vaccine containing ClyII and ClyIII or effective parts or derivatives thereof will provide protection against infection by serotypes 2, 3, 4, 6, 7, 8 and 12, and partial protection against the other serotypes except 10; a vaccine containing ClyI and ClyIII or effective parts or derivatives thereof provide protection against infection by serotypes 10, and partial protection against the other serotypes except 7 and 12. A preferred form of the vaccine contains ClyI, ClyII and ClyIII or immogenic parts or detoxified derivatives thereof, and is effective against all known and probably also against any still unknown serotype of *A. pleuropneumoniae*.

The vaccine of the invention contains the polypeptide or polypeptide derivatives in immunogenically effective amounts, for example between 0.1 and 1000 µg, more particularly between 1 and 100 µg of protein per dosage unit. An important advantage of the invention is that both the absolute and the relative amounts of the immunogens can be adjusted according to the intended use. In contrast, all prior art vaccines contain immunogenic factors in fixed ratios, since they were produced by live *A. pleuropneumoniae* cells, and separation of the factors was not contemplated and hardly possible. The optimum levels and ratios depend on the nature of the infection against which protect is required, the characteristics of the animals to be protected and other factors known to the skilled person. The vaccine may be administered in a conventional way, such as intravenously, intramuscularly, subcutaneously, intraperitoneally, intranasally or orally.

In addition to the cytolysin or part or derivative thereof, the vaccine may comprise an immunologically acceptable carrier, such as aqueous diluents, suspending aids, buffers; furthermore, excipients and adjuvants known in the art may be present. Suitable adjuvants include aluminum hydroxide, Freund's adjuvant (complete or incomplete), bacteria such as *Bordetella pertussis* or *E. coli* or bacterium derived matter, immune stimulating complex (iscom), oil, saponin, oligopeptides or other adjuvants known to those skilled in the art. The protein may also be coupled to an acceptable carrier molecule, particularly a natural or synthetic polymer such as polypeptides, polysaccharides, polystyrene, etc. The vaccine may also contain other immunogens related to other diseases in a prophylactically or therapeutically effective amount, to obtain a multivalent vaccine.

The cytolysin or part or derivative thereof may also be fused to another polypeptide; such other polypeptide may be a carrier polypeptide or, advantageously, a second and possibly a third cytolysin or part or derivative thereof. In a preferred embodiment, the vaccine contains a fused polypeptide comprising immunogenic parts of two or three cytolysins. Such a fused polypeptide may be prepared by coupling of the relevant polypeptides, or by fusing the nucleotide sequences encoding said polypeptides followed by suitable expression of the fused nucleotide sequence.

In the process of producing a cytolytic protein of *A. pleuropneumoniae* or a part or a derivative thereof, suitable for use in the vaccine as described above, in step a) a nucleotide sequence encoding a cytolysin is selected and optionally modified by insertion, substitution or deletion of nucleotides to obtain a sequence encoding an immunogenically active and/or a detoxified protein. The selection of the nucleotide sequence may be performed by screening the gene library of *A. pleuropneumoniae* using established methods, as illustrated in the examples to the present specification. The nucleotide sequence may then be cloned and isolated; alternatively, the nucleotide sequence may be synthesized. The sequence preferably comprises the sequence encoding an activator protein for the cytolysin, which may be the activator of the cytolysin itself; in the latter case for example, the nucleotide sequence may comprise the clyIICA gene.

The nucleotide sequence is then inserted in a suitable vector in step b). Such a vector may or may not comprise a promoter and optionally an enhancer. The promoter can be selcted to obtain the desired level of expression. Modification of the nucleotide sequence may be performed in the vector, instead of before insertion as explained above. Suitable vectors are art-known.

Step c) can be carried out using standard techniques (see for example: Maniatis, T. et al, (1982) Molecular Cloning, A Laboratory Manual, Cold Spring Harbor Laboratory). The host cell in which the vector containing the nucleotide sequence is transferred preferably also produces transport proteins allowing the cytolysin or part or derivative thereof to pass the host cell membrane and even be screted into the medium, and thus to be easily harvested. The transport proteins may be derived from *A. pleuropneumoniae* or from the host cell or from another organism. The host cell is advantageously *E. coli*.

The nucleotide sequence to be used for producing the cytolysin can be derived from the sequence shown in FIGS. 1, 2 and 3, relating to the clyI (SEQ ID NO: 1:), clyII (SEQ ID NO:2:), and clyIII (SEQ ID NO:3:) genes respectively. The nucleotide sequence can comprise the entire gene, or part thereof encoding at least an epitope of the protein. The nucleotide sequence can be modified by deletions, substitutions or insertions, in particular those which result in a sequence encoding a detoxified derivative of the cytolysin, or those which result in a sequence which, although modified, still encodes the amino acid sequence of the cytolysin or derivative thereof.

Another advantageous type of vaccine provided by the present invention is a vaccine which does not contain the immunogenic protein or proteins as described above, but which contains a recombinant expression system such as a microorganism, carrying a nucleotide sequence encoding said immunogenic protein, for example integrated in its genome or present as an expression vector. Immunization is then induced by administration of the vaccine containing this expression system and subsequent replication and expression in the vaccinated animal. Examples of microorganisms that car be used for this purpose include bacteria such as Salmonella or E. coli, bacteriophages, and viruses, such as vaccinia virus, adenovirus, baculovirus, SV40 retrovirus, hepatitis B virus and pseudorabies virus; other examples are cells which have been transformed with one of these viruses or with other vectors and cells wherein these viruses replicate. These recombinant expression systems constitute an aspect of the present invention.

Monoclonal antibodies to the cytolysins or immunogenic parts or derivatives thereof may be produced in a known manner, e.g. by immunizing a suitable animal with the cytolysin or an appropriate epitope thereof, fusing the resulting cells producing the antibody to the cytolysin with myeloma cells, selecting and cloning the resulting hybridoma cells to produce the antibody. The antibodies to cytolysin I, II and III or to parts of these proteins can be used in a diagnostic method for assaying an infection with *A. pleuropneumoniae.* The antibodies may be employed in an agglutination assay wherein the antibody may be coupled to a solid particle. The antibodies may be labeled by an enzyme, a luminescent substance, a radioactive isotope, a complexing agent, or by other known means; they may be used in a sandwich assay with a second antibody, one of the two being labeled. The antibodies may be a part of a diagnostic kit, which further contains conventional components for carrying out an immunoassay.

The antibodies are also useful as a means of passive immunization of an animal against *A. pleuropneumoniae* wherein the antibody inhibits the activity of cytolysins that are introduced by infection. A vaccine to be used for this purpose comprises antibodies to one or more, preferably three different, cytolysins, optionally together with suitable carriers and adjuvants.

The nucleotide sequences illustrated in FIGS. 1, 2 and 3 or in particular suitable parts thereof are also useful as diagnostic tools. Such DNA probes can be used for determining the presence of *A. pleuropneumoniae* in biological samples of animals. The DNA probes of the invention are used according to known techniques for sampling, hybridization, possible amplification and detection. The DNA probes can be part of a diagnostic kit, which may further contain usual components, such as filters, labeling substances, diluents, amplification or detection aids, etc.

EXAMPLE 1

Gene Cloning and Identification of Cytolysins I, and II

Materials and Methods:

Bacterial strains, plasmids and cloning vectors.

The reference strain CVI 13261 of *A. pleuropneumoniae* serotype 9 was used as DNA source. The gene library was made in bacteriophage lambda Gem11 (Promega) and propagated in *E. coli* LE 392 (Sambrook, J., E. F. Fritsch, and T. Maniatis. (1989). Molecular cloning. A laboratory manual. Second edition. Cold Spring Harbor Laboratory Press. Cold Spring Harbor. N.Y.). Specific DNA fragments were (sub)cloned in pKUN plasmid vectors (Konings, R. N. H., et al. (1987) *Methods Enzymol.* 153: 12–34) and transformed into *E. coli* JM101 (Sambrook, supra). Plasmid pLKT 52, containing the RTX determinant of *P. haemolytica,* was prepared by Dr. R. Lo (Strathdee, C. A., and R. Y. C. Lo. (1989) *J. Bacteriol.* 171: 916–928). Plasmid pLG575, a pACYC184 based plasmid containing the hlyB and hlyD secretion genes of *E. coli* was prepared by Dr. C. Hughes (Gygi, D., C. Hughes, et al (1990) *Mol. Microbiol.* 4: 123–128).

Construction and screening of the DNA library.

High molecular weight DNA was isolated by SDS/proteinase K lysis, phenol and phenol/chloroform extractions, and precipitation with ethanol (Sambrook, supra). With this DNA a library was constructed in lambda Gem11 according to the methods recommended by the supplier of the vector arms (Promega). Plaque lifts from this library were hybridized with appropriate restriction fragments which were labelled in advance with [$^{32}$P]dATP (Amersham) using the nick translation kit of Boehringer, Mannheim. Plaques that hybridized were visualized by exposure to X-ray film (Eastman Kodak). The library was also screened for the presence of hemolytic plaques. For that purpose plaques, grown at 37° C. on a Luria broth agarplate, were overlaid with 0.8% agarose containing 5% sheep erythrocytes, 10% Serum Plus (Hazelton) and 0.5 times Eagle's minimal essential medium (Flow laboratories, Irvin, England) in phosphate buffered saline. The plates were incubated at 37° C. for 6 to 12 hr. Selected plaques were purified to homogenicity by at least two cycles of plating and screening.

DNA manipulation and sequence analysis.

DNAs were digested to completion with restriction enzymes according to the specifications of the enzyme supplier (Pharmacia LKB, Sweden). The resulting fragments were separated by electrophoresis on 0.8% agarose gels. Desired fragments were electrophoretically eluted from gel slices and further purified by extractions with phenol and chloroform and precipitation with ethanol. Fragments were (sub)cloned in pKUN plasmid vectors (Konings, supra) by standard molecular biological techniques (Sambrook, supra). Progressive unidirectional deletions were made with the Erase-a-base system from Promega. Nucleotide sequences were determined by the dideoxy chain termination method (Sanger, F. et al (1977) *Proc. Natl. Acad. Sci. USA.* 74: 5463–5467). The sequences were analyzed using the PCGENE (Intel ligenetics Corp., Mountain View, Calif.) and Wisconsin GCG (University of Wisconsin) analysis software packages.

Gene Screen Plus nylon membranes (Du Pont NEN) were used for Southern blot analysis. The blots were hybridized with DNA probes, labelled as described above, according to the instructions of the membrane supplier. Before exposure the blots were washed a final time with 0.1× SSC, 0.1% SDS for 30 min at 65° C. for homologous probes and with 1× SSC, 0.1% SDS for 30 min at 50° C. for heterologous probes. All other DNA manipulations were done with standard molecular biological techniques (Sambrook, supra).

Immunoblotting, monoclonal antibodies (MAbs) and toxin bioassays.

Proteins present in recombinant plaques, cells or supernatants of stationary growth cultures were electrophoresed through reducing and denaturing 6% polyacrylamide gels (Laemmli, U. K. (1970) *Nature* (London) 227: 680–685). The separated proteins were stained with silver or blotted onto nitrocellulose with a semidry blotting apparatus (Bio-rad Laboratories Inc.). The blots were incubated according to the method of Towbin (Towbin, H., et al (1979) *Proc. Natl. Acad. Sci. USA.* 76: 4350–4354) with convalescent swine serum derived from an *A. pleuropneumoniae* serotype 9 infected pig or with MAbs specific for ClyI and/or ClyII. MAb CVI-ApCly 9.1 and 9.2 recognize ClyI, MAb CVI-ApCly 9.3 ClyII, and MAb CVI-ApCly 9.4 reacts with ClyI and ClyII (see example 3). Bound antibodies were detected with an anti mouse or anti swine immunoglobulin G-alkaline phosphatase conjugate (Zymed Laboratories Inc.) and color development with the substrates nitroblue tetrazolium (Merck) and 5-bromo-4-chloro-3-indolyl phosphate (Boehringer Mannheim).

Recombinant toxin, isolated from logarithmic growing cultures, was tested for hemolytic and cytotoxic activity as described earlier (Kamp, E. M., and L. A. M. G. van Leengoed (1989) *J. Clin. Microbiol.* 27: 1187–1191). Hemolytic and cytotoxic titers were expressed as the reciprocal of the highest dilution showing at least 50% lysis of the target cells.

RESULTS

Gene cloning.

To determine whether *A. pleuropneumoniae* serotype 9 encoded for toxins related to the RTX cytotoxin family, a 3.7 kilobasepairs (kb) PvuI/SalI DNA fragment derived from the leukotoxin (lkt) determinant of *P. haemolytica* (Stathdee, C. A. and R. Y. C. Lo. (1987) *Infect. Immun.* 55: 3233–3236) and containing lktA, the 3'-end of lktC and the 5'-end of lktB (lktCAB) was hybridized to genomic DNA. Three specific DNA fragments were found to be homologous to the probe. The lktCAB probe was then used to screen a library of the *A. pleuropneumoniae* serotype 9 DNA which was prepared in the vector lambda Gem11. Forty recombinants reacted as strongly positive. To determine whether recombinants with cytolytic activity but without any detectable homology to lkt DNA existed, the library was also screened for the presence of recombinants capable of hemolysis of sheep red blood cells. Three recombinant plaques showed clear hemolytic activity. These hemolytic clones hybridized however with the lktCAB probe, indicating that they shared identical sequences with the clones that were found to be positive with the lkt probe. The hemolytic clones expressed a 103 kDa protein that was absent in non-hemolytic clones. This 103 kDa protein reacted with MAbs specific for ClyII and not with MAbs specific for ClyI (see below). These data indicated that we had cloned the ClyII gene.

To localize the ClyII gene in the 9–21 kb long inserts of the selected recombinants, we digested the DNA of 23 positive clones, including the hemolytic ones, with the restriction enzyme HindIII. The resulting fragments were electrophoresed, blotted onto nylon membranes and hybridized with the lktCAB probe. All recombinants contained a 2.4 kb fragment homologous to the probe. Several recombinants also contained a 4.4 kb fragment that hybridized. Others contained a hybridizing fragment of variable length in addition to the 2.4 kb fragment. Apparently only a part of the 4.4 kb HindIII fragment is present in the latter clones and has been ligated to one of the vector arms. These data provided a location for the ClyII gene (clyIIA).

Although the lktCAB probe used for screening contained approximately 300 bp of the lktB secretion gene, it appeared that none of the 9–21 kb inserts of the selected clones contained intact B and/or D genes. To investigate whether such sequences were present elsewhere in the genome, a 1.2 and a 0.7 kb EcoRV DNA fragment, covering both the 3' end of the lktB gene and the 5' end of the lktD gene of *P. haemolytica* (lktBD, 24), were hybridized with genomic DNA. A 4.3 kb HindIII fragment hybridized. This fragment was absent from the three hemolytic clones and all the clones that were selected with the lktCAB probe. From these data we concluded that the genome of *A. pleuropneumoniae* does contain sequences related to the RTX B and D secretion genes but that these sequences are not contiguous to the ClyII toxin gene.

In order to clone the RTX B and D related DNA, HindIII digested and size fractionated genomic DNA of strain CVI 13261 was ligated into a HindIII digested pKUN plasmid. After transformation into *E. coli* and colony hybridization with lktBD we were able to isolate a clone that contained the 4.3 kb HindIII fragment. Using this fragment we also isolated a 7.0 kb BglII/EcoRV fragment that overlapped the 4.3 kb HindIII fragment at the 5'-end, and a 4.2 kb BamHI fragment that overlapped the 4.3 kb HindIII fragment at the 3'-end. Restriction analysis and Southern hybridization provided a location for the postulated secretion genes clyBD.

Nucleotide sequence analysis.

The clyIICA locus and the clyBD locus were subjected to nucleotide sequence analysis. The established sequences and the derived amino acid sequences of the major open reading frames are shown in FIG. 2. Both loci contained two major open reading frames; these were named clyIIC, clyIIA, clyB and clyD (see also FIG. 1 and FIG. 2). The maps of restriction sites deduced from the sequences correlated well with the maps of restriction sites as determined from the cloned DNA and the genomic DNA (data not shown). Thus no detectable rearrangements had occurred during the cloning procedure. The sequences were numbered starting at −231 (clyIICA locus) and −592 (clyBD locus) to correspond to the orientation and location of the major open reading frames. In clyIICA the open reading frame from 1 to 477 (clyIIC) codes for a polypeptide of 159 amino acids (18.5 kDa) and the frame from 519 to 3386 (clyIIA) for a polypeptide of 956 amino acids (102.5 kDa). The latter protein is the ClyII toxin and, as other RTX toxins, contains glycine rich repeats near the carboxy terminus. In clyBD the frame from 1 to 2133 (clyB) codes for a polypeptide of 711 amino acids (80.2 kDa) and the frame from 2142 to 3575 (clyD) for a polypeptide of 478 amino acids (54.9 kDa).

These protein sequences were very similar to the protein sequences of the RTX determinants of *E. coli, P. haemolytica* and *A. pleuropneumoniae* serotype 5. Their mutual hydropathy profiles (Kyte, J. and R. Doolittle (1982) *J. Mol. Biol.* 157: 105–132) were also quite similar. The ClyIIC and ClyIIA proteins were more homologous to the LktC and LktA proteins of *P. haemolytica* than to the HlyC and HlyA proteins of *E. coli* (Stathdee, C. A. and R. Y. C. Lo (1987) *Infect. Immun.* 55: 3233–3236). In addition the ClyIIA toxin was identical to the 105 kDa toxin identified by Chang et al. in serotype 5 (Chang, Y. et al (1989) *DNA* 8: 635–647). The ClyIIC protein differed however from its counterpart in serotype 5 at three positions; at amino acid position 5 (extra residue), between residues 41 and 47 (frameshift due to an insertion and deletion of nucleotide residues at positions 125 and 138) and around amino acid position 65 (nucleotide sequence of TGGGCC in serotype 9 and TCCCGG in serotype 5).

The sequence of clyIICA was highly homologous to that of other RTX sequences up to position 3490. This position corresponded to amino acid residue 12/13 of known RTX B secretion proteins. Instead of RTX B protein related sequences we found an open reading frame in the opposite DNA strand downstream this position. This finding confirmed that in serotype 9 no RTX-B related sequences were contiguous with the toxin gene. Probably a recombination occured at position 3490 (amino acid position 12/13 of the truncated RTX-B homlogue) in the clyII operon.

Identification and secretion of ClyII.

A 2.7 kb DNA fragment extending from the 5' end of the insert of one of the selected recombinants up to the KpnI site downstream clyIIA was ligated into pUC18 DNA. *E. coli* cells that contained this plasmid produced a 103 kDa protein. This protein reacted with a convalescent swine serum, with MAbs specific for ClyII, and not with MAbs specific for ClyI. To provide additional evidence that clyIIA encodes for the 103 kDa ClyII, we electrophoresed the proteins present in clyIICA containing *E. coli* cells and the proteins present in culture supernatants of serotype 9 alongside a mixture of both preparations. The data clearly indicated that the clyIIA encoded protein comigrates with ClyII.

To assess whether the ClyII toxin also shared functional relatedness with the enterobacterial RTX cytolysins, *E. coli* cells carrying the clyIICA genes were cotransformed with a compatible plasmid coding for the *E. coli* hlyBD secretion proteins. The intra- and extracellular proteins of these cells and also of cells that contained either one of these plasmids were assayed for the presence of ClyII. ClyII was only secreted from the cells when the secretion genes were present in trans. These data therefore demonstrated hlyBD mediated export of ClyII across *E. coli* membranes and a functional relationship between ClyII and the RTX toxin family.

To study the biological activity of ClyII, culture supernatants and cell lysates of the same set of cells were tested for hemolytic and cytotoxic activity. The cytolytic activities in these supernatants and cell extracts perfectly matched with the presence of the ClyII protein among these preparations. These data also indicated that ClyII had two activities: a moderate cytotoxic activity and a weak hemolytic activity. These activities are schematically represented in Tables A and B.

Identification of ClyI.

Figure 8:
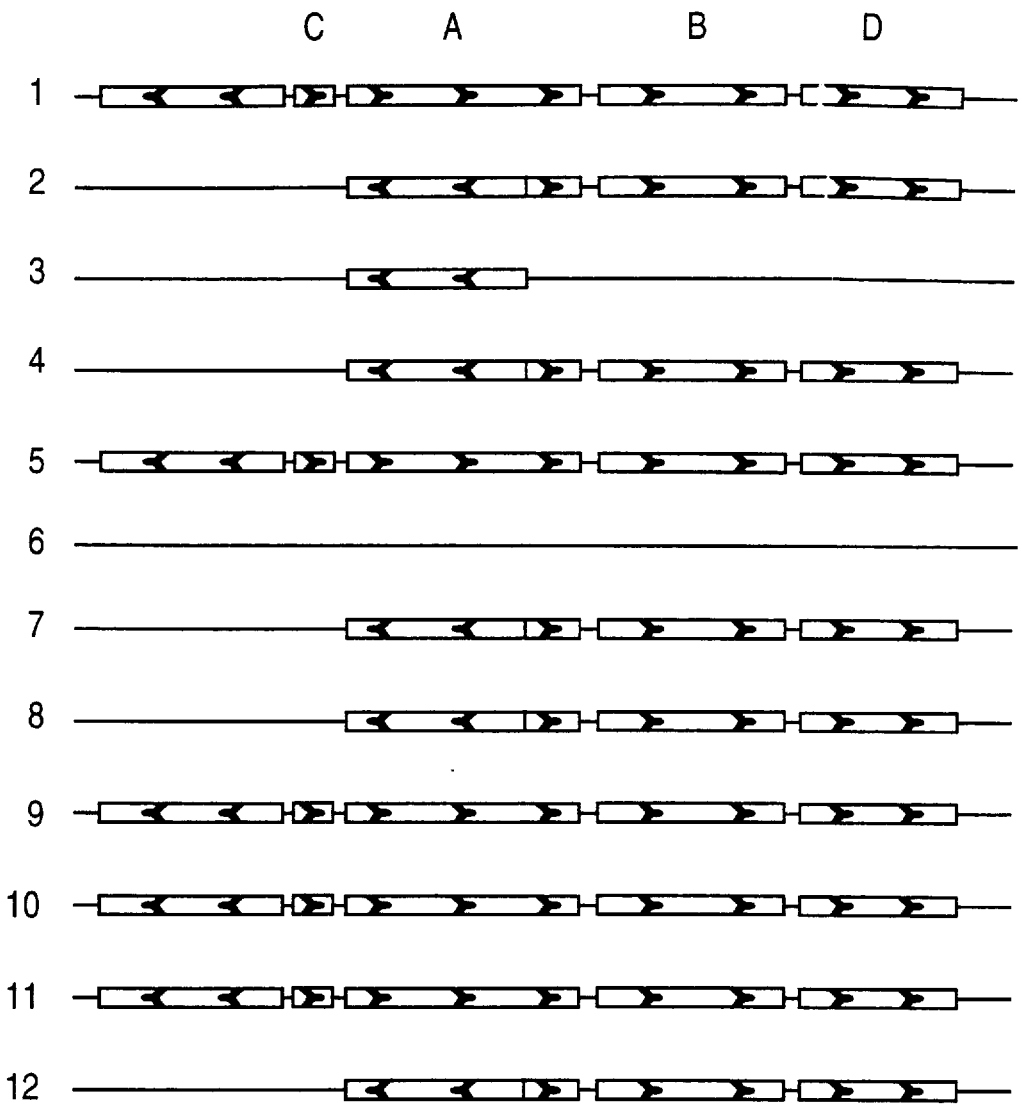
FIG. 8 shows the ClyI determinant organization of the *A. pleuropneumoniae* serotypes 1–12.

A 7.4 kb NsiI/HindIII DNA fragment containing the clyB gene and approximately 4.5 kbp of upstream sequences (FIG. 1) was ligated into pUC18 DNA. The proteins produced by cells that contained this plasmid were electrophoresed in parallel with culture supernatant of *A. pleuropneumoniae* serotype 9 and of ClyII secreting *E. coli* cells. After blotting we screened for the presence of ClyII, ClyI and ClyII+ClyI. The data demonstrated that the 7.4 kb NsiI/HindIII fragment encodes a 105 kDa protein which is indistinguishable from ClyI and which is clearly different from ClyII. This ClyI protein could also be secreted from *E. coli* cells when they contained the hlyBD secretion genes in trans. From these data we concluded that the clyBD genes form part of an RTX operon that codes for ClyI. Since the secretion genes belong to the ClyI operon, these genes are now referred to as clyIBD. The upstream sequence of clyIBD containing the clyICA genes was sequenced as described before. The sequence is shown FIG. 1. The genomic organization of the ClyI determinant was determined for the 12 serotypes of *Actinobacillus pleuropneumoniae* and is depicted in FIG. 8.

Cloning of the gene encoding ClyIII

Genomic DNA of *Actinobacillus pleuropneumoniae* serotype 8 was partially digested with the restriction enzyme Sau3A to fragments with an average size of about 1000 basepairs. These fragments were partially filled in using Klenow DNA polymerase and dGTP and dATP. The plasmid expression vector pUEX2 (Bressan, G. M. and K. K. Stanley (1987) *Nucl. Acid Res.* 15: 10056) was digested with the restriction enzyme SalI and partially filled in using Klenow DNA polymerase and DCTP and dTTP. The modified fragments were ligated into the linearized vector and *E. coli* strain LE392 was transformed with this ligation mixture. Approximately 90,000 independent recombinants were grown at 37° C. and after two hours of induction of the synthesis of β-galactosidase fusion proteins at 42° C., the proteins present in the recombinants were bound to nitrocellulose membranes. The membranes were screened with MAb 2.2 (see example 3), and immunoreactive clones were visualized using rabbit anti mouse serum conjugated with alkaline phosphatase. Three immunoreactive clones were found, 3.4, 5.4, and 7.4. Clones 3.4 and 7.4 contained a 400 base-pair fragment of *A. pleuropneumoniae* serotype 8, clone 5.4. contained a 1000 bp fragment. Since these fragments cross-hybridized, they contained similar DNA sequences. Sequence analysis of one of these fragments demonstrated that it did not contain the complete clyIII gene. To obtain the complete clyIII gene, genomic DNA of *A. pleuropneumoniae* serotype 8 was digested to completion with the restriction enzyme HindIII. The resulting fragments were separated on a 0.75% agarose gel and after transfer to nitrocellulose they were hybridized with the DNA fragment present in clone 7.4 which had been labeled with $^{32}$P. A 3200 bp fragment hybridized. This fragment was eluted from the gel and cloned into HindIII restricted plasmid pGEM7Z(+) (Promega) by standard molecular biological techniques. One of the resulting clones, clone 5.2, was shown to harbor the 3200 bp fragment. The nucleotide sequence of this fragment was determined and analysis of the seuence revealed an open reading frame of a distal part of a gene coding for a protein homologous to the *E. coli* α-hemolysin, and the proximal part of a gene coding for a protein homologous to Hly B of *E. coli*. It was concluded that the 3200 bp fragment of clone 5.2 comprises sequences of an RTX-toxin operon and hence that ClyIII is a member of the RTX-toxin family. Thus clone 5.2 contained the distal part of an RTX A-gene (toxin gene) and the proximal part of an RTX B-gene (coding for a transport proten). The full length sequence of the putative clyIII gene was obtained by the cloning and sequencing of a 4200 bp NsiI/XbaI fragment (clone 6.1) that hybridized with a 1200 bp HindIII/XbaI fragment of clone 5.2 and overlapped with the 5'-end of the fragment in clone 5.2. The nucleotide sequence showed the open reading frame of a gene coding for the proximal part of a RTX A protein and a complete RTX C protein.

For expression purposes we constructed a plasmid that contained an XbaI/XhoI fragment made by combining the 4200 bp NsiI/XbaI insert of clone 6.1 with a 1300 bp XbaI/XhoI fragment of clone 5.2. *E. coli* cells that contained this plasmid produced a protein with a molecular weight of about 120,000 dalton that reacted with the ClyIII specific MAb 2.2. This demonstrated that we had cloned the gene encoding ClyIII.

Cotransformation of these cells with plasmid pLG575, carrying the Hly B and D transport proteins of the *E. coli* hemolysin determinant, resulted in the secretion of the 120,000 dalton protein. The secreted protein had a strong cytotoxic activity for porcine lung macrophages. It did not show any hemolytic activity to sheep erythrocytes.

In conclusion, the 120,000 dalton protein is demonstrated to be the ClyIII protein since it has the same size, the same immunological properties, and the same biological activity as the ClyIII protein of *A. pleuropneumoniae*. Furthermore from hybridization studies we know that sequences homologous to the ClyIII coding gene are only present in the serotypes 2, 3, 4, and 8, the only serotypes that produce ClyIII.

The nucleotide sequence of the ClyIII gene was determined essentially as described above. The sequence is shown in FIG. 3.

EXAMPLE 2

Heterogeneity in the Cytolysin II Genetic Determinant of *Actinobacillus pleuropneumoniae* Serotypes Materials and methods Bacterial strains, genomic DNA, plasmids and oligonucleotides.

The reference strains for the twelve serotypes of *A. pleuropneumoniae* were used as source of genomic DNA. The reference strains for the serotypes 1 to 12 were respectively s4047, 1536, 1421, M62, K17, Femo, WF83, 405, 13261, D13039, 56153 and 8329. High molecular weight DNA was isolated by proteinase K/SDS lysis, phenol/chloroform extractions and precipitation with ethanol (Maniatis, T. et al (1982) Molecular Cloning, A Laboratory Manual, Cold Spring Harbor Laboratory). DNA fragments were cloned with the plasmid pGEM7Zf(+) (Promega Corporation, Madison, Wis.) in *E. coli* strain JM101, using standard molecular biology techniques (Maniatis, supra). Sequences of oligonucleotides used for the PCR are given. Their position in serotype 9 clyIICA is indicated between brackets. Position 1 is the first base of the clyIIC reading frame (see Example 1).

Oligo 283: CCATTACAGAACGTTGGTAC (−232 to −208) of SEQ. ID. NO. 2.

Oligo 284: ATTAAT<u>GCGGCCGC</u>AGGACCAG (1414 to 1435) of SEQ. ID. NO. 2.

Oligo 285: ACAAAA<u>GCGGCCGC</u>ATCTTACA (1356 fo 1377) of SEQ. ID. NO. 2.

Oligo 286: CTACAGCTAAACCAAAGATCCT (3473 to 3493) of SEQ. ID. NO. 2.

Oligo 158: CGTAGGTGTTGCCCC (2033 to 2052) of SEQ. ID. NO. 2.

Oligo 322: ATTCAAT<u>AAGCTT</u>GAGCCGC (3366 to 3385) of SEQ. ID. NO. 2.

Underlined sequences are recognition sites for the restriction enzymes HindIII in oligonucleotide 322 and NotI in 284 and 285. These sites were introduced for cloning purposes (NotI was not used in this study) by the modification of one (322), two (285) or three (284) bases of the original serotype 9 clyIICA sequence.

Southern blots and dot-blots.

Southern blots of restriction fragments of genomic DNA, separated on 0.8% agarose gel and dot-blots of high molecular weight genomic DNA were made with Genescreen plus membranes (NEN Research Products, Boston, Mass.). For the Southern blots 1 $\mu$g of DNA per lane was used, and for the dotblots 50 ng per dot. The blots were hybridized overnight in a Hybaid hybridization oven at 65° C. DNA with $\alpha^{32}$P dCTP (Amersham, UK) labeled DNA prepared by random prime labeling (Random Primed DNA labeling kit, Boehringer Mannheim, Mannheim, FRG). The blots were washed with a final stringency of 0.2 SSC (1× SSC is 0.15 M sodium chloride, 0.015 M sodium citrate) and 1% Sodium Dodecyl Sulphate (SDS) for 15 min at 65° C. Radioactivity was detected by autoradiography using intensifying screens on X-omat AR film (Eastman Kodak, Rochester, N.Y.).

Amplification and radiolabeling of DNA by the PCR.

The clyIICA sequences were amplified by the PCR using genomic DNA from the *A. pleuropneumoniae* reference strains as a template. The PCR was done in a volume of 50 ml containing approximately 100 ng template DNA, 1 $\mu$M of each of two specific oligonucleotides, 1 U Taq DNA polymerase (Perkin Elmer Cetus, Norwalk, Conn.), 0.2 mM of each of four deoxynucleotide triphosphates (dNTP), 25 mM Tris/HCl, pH 8.7, 2.5 mM $MgCl_2$ and 0.05% gelatin. The reaction mixture was covered with a drop of mineral oil to prevent evaporation and subjected to 30 PCR cycles of 1 min at 92° C., 1 min at 55° C. and 3 min at 74° C. in a Thermal Cycler (Perkin Elmer Cetus). Amplified DNA fragments were separated by agarose gel electrophoresis and extracted from the gel with GeneClean (Bio 101 LaJolla, Calif). Two to four nanogrammes of the purified DNA fragments were radiolabeled in a successive PCR with a dNTP concentration of 0.05 mM each, and 5 mCi $\alpha^{32}$P dCTP. Unincorporated dNTPs were removed by precipitating the radiolabeled DNA from the phenol/chloroform extracted reaction mixture with ethanol in the presence of 2.5 M ammonium acetate. The relatively high concentration of unlabeled dNTPs used in this PCR will decrease the specific activity of the synthesized DNA, but will favor the fidelity and complete extension of the PCR products, desirable for RFLP studies (Jansen, R. and F. D. Ledley (1989) *Gene Anal. Techn.* 6: 79–83).

Inverse PCR, cloning and sequence analysis.

Inverse PCR (Ochman, H. et al (1988) *Genetics* 120: 621–625) was done under the same conditions as the PCR described above, except that the extension reaction was 90 sec at 74° C. The template DNA for the inverse PCR was prepared as follows: HindIII digested genomic DNA was size fractionated by agarose gel electrophoresis and extracted from the gel with GeneClean. These fragments were circularized by self-ligation with T4 ligase in a volume of 50 $\mu$l containing approximately 100 ng of DNA fragments. One tenth of the ligation product was used as a template in the inverse PCR. The inverse PCR resulted in a high background of aspecific products. The desired amplification products were size fractionated by agarose gel electrophoreses and extracted from the gel with GeneClean. Reamplification of these fragments was done in a subsequent PCR using the same oligonucleotides and reaction conditions. The resulting fragments were cloned into pGEM7Zf(+), using the HindIII site resulting from the circularization reaction and an artificial HindIII site in oligonucleotide 322. Sequence analysis of the cloned fragments was done with the T7 sequencing kit (Pharmacia, Uppsala, Sweden) by using oligonucleotides specific for the SP6 and T7 promotors (Promega).

Restriction fragment analysis.

Radiolabeled DNA fragments were separately digested with the restriction enzymes AluI, Sau3AI, RsaI and HinfII. The resulting DNA fragments were separated on a vertical 5% polyacrylamide (acryl:bisacryl is 19:1) gel with dimensions of 400×500×1.5 mm, buffered with 0.18 M Tris/boric acid (pH 7.8), 0.5 mM EDTA (TBE). The digestion products were visualized by autoradiography of the dried gel.

RESULTS

Presence of clyIICA in the serotypes 1-12 and comparison of their sequences. The presence of clyIICA sequences in the genomic DNA of the twelve *A. pleuropneumoniae* serotypes was detected by using dot-blot hybridization with serotype 9 clyIICA sequences as a probe. This probe, comprising bases 315 to 3233, hybridized to the DNA of all serotypes, except serotype 10. Genomic DNA of the twelve serotypes was subjected to PCR using four oligonucleotides derived from the serotype 9 clyIICA genes. FIG. 5A shows the position of these oligomers in the two contiguous genes. Set 283/284 was used for amplification of the 5' region, 285/286 for the 3' region and 283/286 for amplification of full length clyIICA. The PCR on the DNA of the serotypes 1, 2, 3, 4, 5, 7, 8, 11 and 12 resulted for each primer set in amplification products of the same size as obtained with serotype 9 DNA (1750 bp for set 283/284, 2050 bp for set 285/286 and 3200 bp for the set 283/286). The 3.2 kb full length fragments of the serotypes 1,2,3,4,5,7,8,11 and 12, generated by using set 283/286, showed identical restriction maps for the enzymes HindIII, Xba I and Pst I as serotype 9 clyIICA. Serotype 6 gave an identically sized amplification product as serotype 9 for set 285/286, but amplification products which were approximately 1800 bp longer for the sets 283/284 and 283/286. Serotype 10 did not give visible amplification products using either set of oligonucleotides.

The degree of similarity between the clyIICA genes of the serotypes 1, 2, 3, 4, 5, 7, 8, 9, 11, and 12 was studied by RFLP analysis of the full length clyIICA sequences, generated in the PCR with the oligonucleotide set 283/286. The DNA fragments were labeled with $\alpha^{32}P$ dCTP and digested with the restriction enzymes AluI, HinfII, RsaI or Sau3AI. The obtained restriction fragments were analyzed by gel electrophoresis and autoradiography. For each of the four restriction enzymes, the number and sizes of the DNA fragments obtained from clyIICA of the serotypes 1, 2, 3, 4, 5, 7, 8, 9, 11, and 12 appeared to be very similar. The RFLP studies on the serotype 12 clyIICA sequences were done in separate experiments.

Cloning and analysis of the sequences adjacent to clyIIA.

Figure 6:
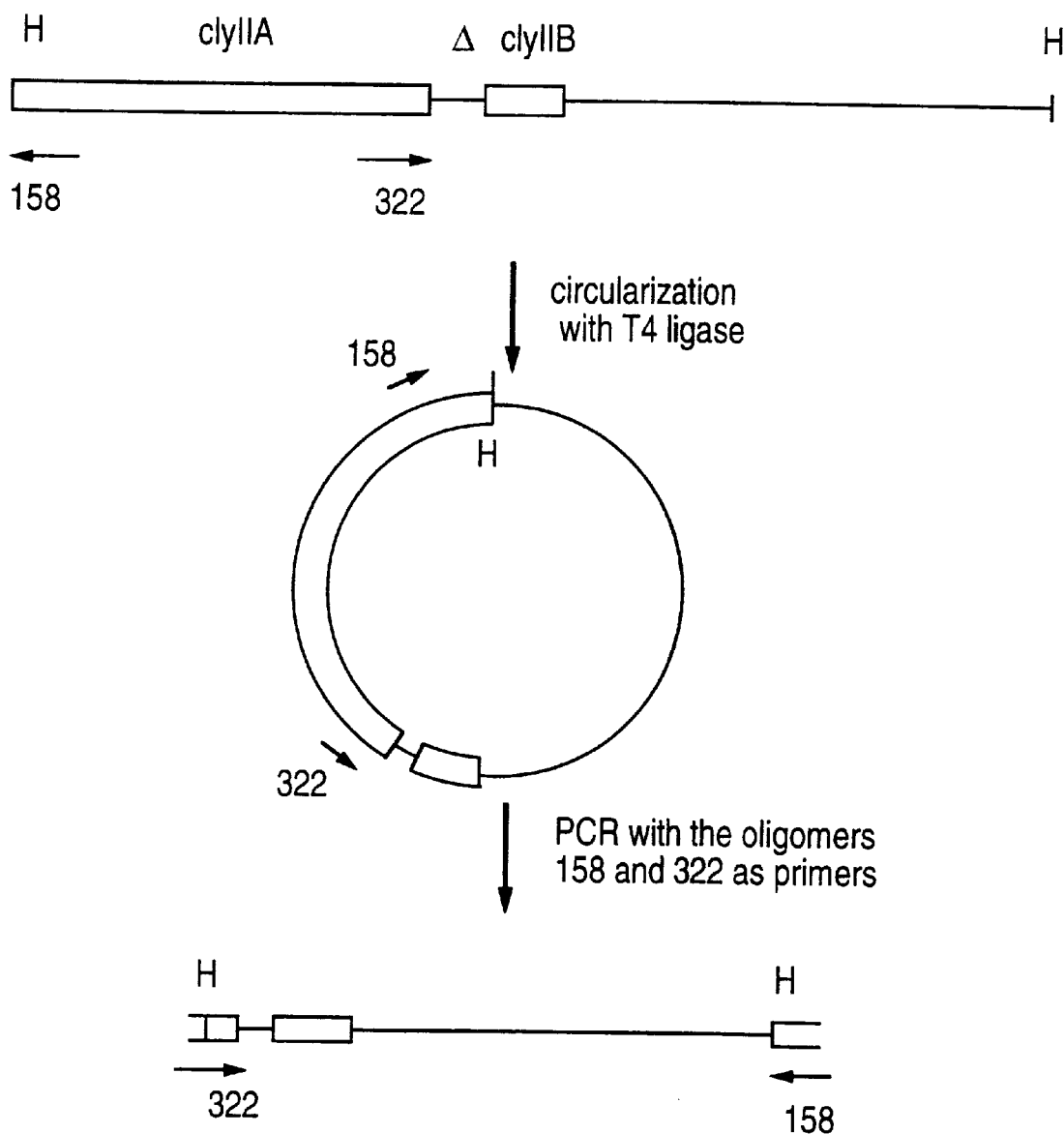
FIG. 6 schematically shows the amplification and cloning of the clyIICA 3' flanking sequence by inverse PCR.
Figure 7:
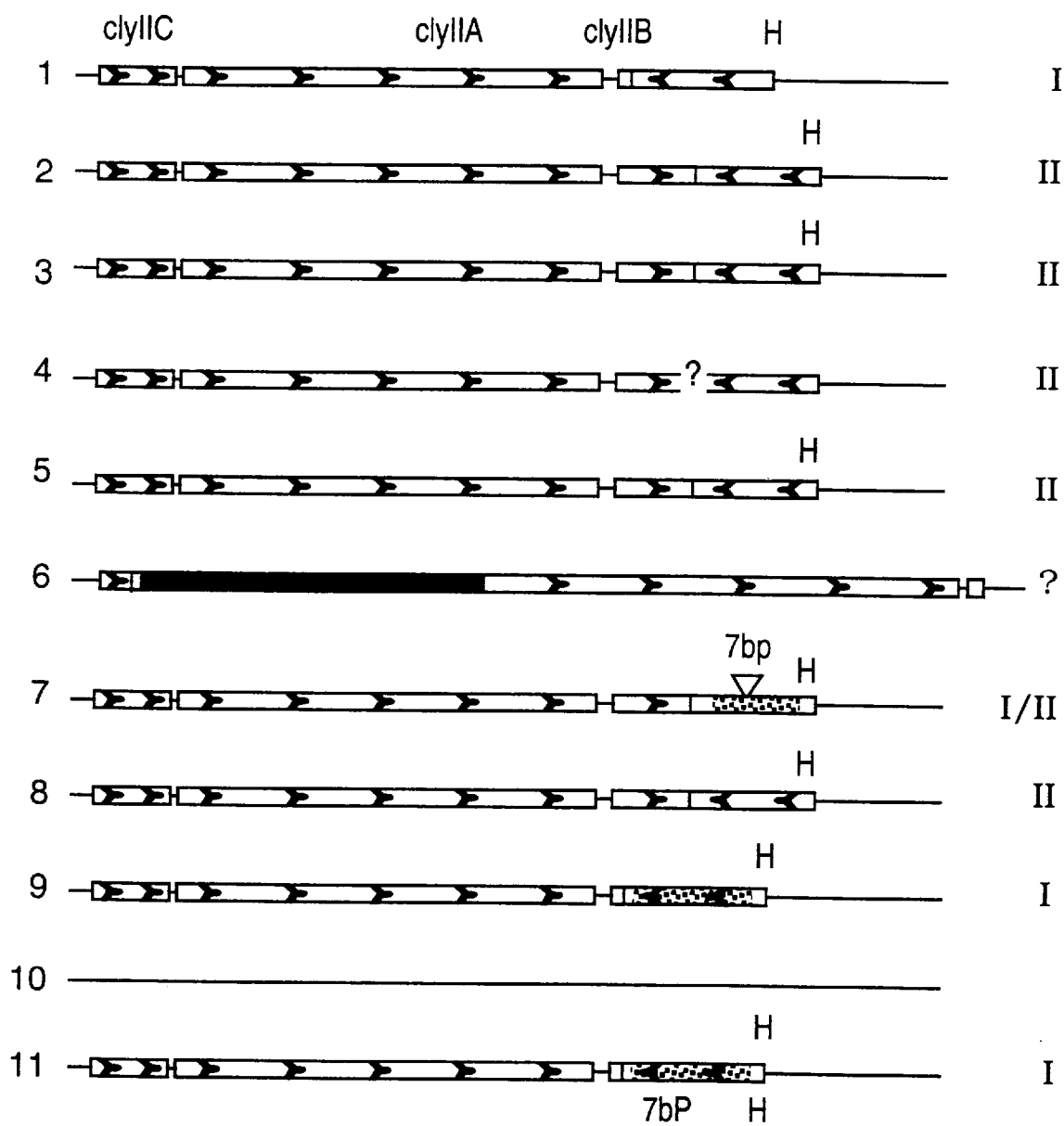
FIG. 7 shows the ClyII determinant organization of the *A. pleuropneumoniae* serotypes 1–12.

The proximal part of a putative clyIIB gene was found adjacent to clyIIA of serotype 5 and 9 (see example 1). In serotype 5 this sequence extended to at least 108 bases, but in serotype 9 it was truncated after 37 bases. To study the presence of this putative clyIIB gene in the other serotypes we cloned the sequences distal of clyIIA 3' by inverse PCR as outlined in FIG. 6. We chose HindIII digestion of the genomic DNA, since the genomic HindIII fragments of most serotypes containing these sequences have a workable size for inverse PCR amplification, and an unique HindIII site is present in clyIICA of all serotypes at base 2008. The probe used in this analysis comprised bases 2008 to 3493 of serotype 9 clyIICA. Among the twelve serotypes, four differently sized HindIII fragments hybridized to this probe. A 2.8 kb HindIII fragment in the serotypes 2, 3, 5, 7, and 8, a 2.3 kb fragment in the serotypes 1, 9, 11, and 12, a 10 kb fragment in serotype 4 and a 4.3 kb fragment in serotype 6. Inverse PCR using these HindIII fragments is expected to result in amplification products, approximately 1300 bases smaller (the number of bases between the oligonucleotides 158 and 322) than the hybridizing HindIII fragments. The inverse PCR resulted in the desired amplification products for all serotypes, except 4 and 6. The failure to get amplification products for serotypes 4 and 6 was probably due to the large sizes of the HindIII fragments, exceding the range of inverse PCR amplification in this system. We cloned the inverse PCR products of the serotypes 1, 2, 3, 5, 7, 8, 9, 11, and 12 into pGEM7Zf(+) and determined their nucleotide sequences. All these serotypes appeared to have a truncated clyIIB adjacent of clyIIA, and two different truncation points were identified, at base 37 and at base 501. We identified two major types of sequences downstream of clyIIB. Type I, present in the serotypes 1, 7, 9, 11, and 12, and type II present in the serotypes 2, 3, 5, and 8. A subtype of type I was identified in serotype 7 and 12, since both had seven additional bases, AACCACT, at position 3664. The sequence of type I was illustrated in example 1 as part (base 3490 to 4499) of the serotype 9 clyIICA sequence. The protein sequence derived from the 501 bases truncated clyIIB has a similarity of 71% to the serotype 9 clyIB (14), and 64% to the *P. haemolytica* lktB. The type I and II sequences did not show any similarity with each other or with RTX-CABD sequences. FIG. 7 shows a schematic presentation of the genomic structure of the clyIICA and the truncated clyIIB genes of the twelve serotypes. The type I sequences are represented by hatched boxes and type II sequences by dotted boxes. None of the twelve serotypes contained a clyII operon with intact genes for the B and D transporter proteins (see also example 1). Hybridization experiments demonstrated however the presence of clyIBD sequences in all serotypes except 3.

EXAMPLE 3

Identification of Hemolytic and Cytotoxic Proteins of *Actinobacillus pleuropneumoniae* by Monoclonal Antibodies Materials and Methods Bacterial strains.

The sources and designations of the reference strains for *A. pleuropneumoniae* serotypes 1 to 12 aere those mentioned in example 2. The field strain CVI 12946 was isolated in the Netherlands from the lung of a pig that died from pleuropneumonia. This strain was typed as serotype 2 by slide agglutination (Kamp, E. M. et al (1987) *Vet. Microbiol.* 13: 249–257).

Preparation of culture filtrates.

*Actinobacillus pleuropneumoniae* strains were cultured in Eagle minimal essential medium plus Earle salts (Flow Laboratories, Irving, UK) and 10% Serum Plus (Hazelton Research Products, Lexena, Kans.) as described earlier (Kamp E. M. and A. M. G. van Leengoed (1989) *J. Clin. Microbiol.* 27 1187–1191). Cultures were centrifuged for 30 min at 10,000× g, and the supernatants were sterilized by passing them through membrane filters of 0.2 μm pore size (Gelman Sciences Inc., Ann Arbor, Mich.). Culture filtrates were stored in aliquots at −20° C. until further use.

Swine sera.

Specific-pathogen-free 4-week-old pigs were endobronchially inoculated with 103 colony forming units of *A. pleuropneumoniae* 1536 (serotype 2) or 13261 (serotype 9). Blood samples were collected 2 months after inoculation. Blood was allowed to clot overnight at 4° C., serum was collected and heated for 60 min at 60° C. to inactivate complement. Sera were stored in aliquots at −20° C.

Monoclonal antibodies.

Culture filtrates of strains CVI 12946 (serotype 2) and CVI 13261 (serotype 9) were detoxified with 0.5% formalin and used to immunize Balb/c mice. The immunization schedule and the preparation of hybridoma cell lines were as described in detail by van Zijderveld et al. (*Infect. Immun.* 57: 1192–1199). Hybridomas were tested for antibody in enzyme-linked immunosorbent assays (ELISA) using microtiter plates coated with culture medium or culture filtrates of strains CVI 12946 or CVI 13261. Hybridomas that tested positive with a culture filtrate and negative with the culture medium were cloned twice by limiting dilution.

The resulting monoclonal cell lines were used to produce ascites fluid in pristane-primed Balb/c mice. Antibody was purified from the ascites fluid by precipitation with 40% ammonium sulfate and dialysis against phosphate-buffered saline, pH 7.2 (PBS). The MAbs were stored in aliquots containing 8 mg protein/ml at −20° C. The immunoglobulin isotype of the MAbs was determined in immuno- diffusion tests using mouse isotype-specific antisera (Nordic, Tilburg, The Netherlands).

ELISAs.

The procedures for ELISA were as described in detail by Van Zijderveld et al. (supra). We used polystyrene microdilution plates coated with culture filtrates of either strain CVI 12946 or CVI 13261. The optimal dilutions for coating were determined by checkerboard titrations using the swine sera as positive sera. Coated plates were stored at −20° C.

Titers of the MAb preparations were determined in an indirect ELISA. Bound antibodies were detected with peroxidase labeled anti-mouse immunoglobulins (Dakopatts, Copenhagen, Denmark) and hydrogen peroxide mixed with 5-aminosalicylic acid. Titers were expressed as the logarithm of the reciprocal of the highest dilution giving an $A_{450}$ of 50% of the maximum obtainable absorbance value.

A competition ELISA was used to determine whether the MAbs recognized different epitopes. MAbs were conjugated to horseradish peroxidase (Boehringer, Mannheim, Federal Republic of Germany). Serial two-fold dilutions of 50 ml samples of non-conjugated MAbs were incubated in coated microdilution plates for 30 min at 37° C. Plates were not washed, and 50 ml of the optimal dilution of each of the peroxidase-conjugated MAbs was added per well. Plates were further incubated for 1 h, washed, and then incubated with the substrate.

Hemolysin assay.

Serial five-fold dilutions of 1 ml of the culture filtrates were tested for hemolytic activity as described by Frey and Nicolet (1988, *FEMS Microbiol. Lett.* 55: 41–46); a suspension of 1% sheep erythrocytes in Tris-buffered saline, pH 7.2, with 10 mM CaCl2 was used. Just before the determination of the $A_{540}$, 20 µl 0.1 N HCl was added to each tube to change the color of the phenol red in the medium to yellow. Hemolytic activities were expressed in hemolytic units; one hemolytic unit was defined as the absorbance value of a solution of 1 part of the 1% erythrocytes suspension and 3 parts distilled water.

Hemolysin inhibition assays.

Inhibition of hemolytic activity was tested in two assays. The first assay was as described by Frey and Nicolet (supra); serial two-fold dilutions of 1 ml samples of all culture filtrates were incubated for 1 h at 37° C. with 10 µl samples of one of the MAbs, swine sera, or buffer. Then, 1 ml of a suspension of 1% sheep erythrocytes in Tris-buffered saline with $CaCl_2$ was added to each tube and from that point on the test was further performed as the hemolysin assay was. The hemolytic activity of the culture filtrates of serotypes 2, 3, 6, and 8 was too weak to determine inhibition. Therefore, we also tested inhibition of hemolytic activity by inoculating *A. pleuropneumoniae* serotypes 1 to 12 onto sheep blood agar plates that contained 0.05% nicotinamide adenine dinucleotide and a 1:100 dilution of one of the MAbs or a 1:200 dilution of the swine sera. Plates without antibodies were used as controls. The plates had a diameter of 5.5 cm and contained 5 ml medium each. Per serotype, one colony of an 18 hour old culture was suspended in 1 ml PBS. Very fine capillary tubes were used to inoculate the plates with these suspensions. After incubating the plates overnight at 37° C. in an atmosphere of 5% $CO_2$, hemolytic zones were measured and compared to those of the controls. Inhibition was expressed as when hemolytic zones were similar to those of the controls, as + when hemolytic zones were present but were more than 50% smaller than the controls, and as + when no hemolytic zones were detected.

Cytotoxin assay.

The isolation of porcine alveolar macrophages and the cytotoxin assay have been described earlier in detail (Kamp, E. M. and L. A. M. G. van Leengoed (1989) *J. Clin. Microbiol.* 27: 1187–1191).

Cytotoxin inhibition assay.

Serial two-fold dilutions of 50 µl samples of all culture filtrates (except serotype 6) were made in PBS in flat-bottomed microdilution plates (8 rows per serotype). Either PBS (control) or one of the MAbs or polyclonal swine sera were added to each row (50 µl per well). MAbs were used in a dilution of 1:100 and swine sera in a dilution of 1:200. Plates were sealed, shaken, and incubated for 1 h at 37° C. An amount of 50 µl alveolar macrophages was added to each well and from this point on, the test was performed as the cytotoxin assay was. Cytotoxin titers were determined and compared with the titer of the control. Inhibition was expressed as when cytotoxin titers were the same as the titer of the control, as + when titers were two to four-fold lower than the titer of the control, and as + when titers were more than four-fold lower than the titer of the control.

Sodium dodecyl polyacrylamide gel electrophoresis and Western blot analysis. Proteins in the culture filtrates were separated by sodium dodecyl sulfate polyacrylamide gel electrophoresis in a Mini Protean II slab cell according to the recommendations of the manufacturer (Bio-Rad, Richmond, Calif.). We used a 4% stacking gel with a 7.5% separating gel, an acrylamide/bisacrylamide ratio of 19/1, 0.75 mm spacers, and combs with 15 wells. Each well was loaded with 15 µl samples and electrophoresed at 25 V on ice. Proteins were transferred onto nitrocellulose filters electrophoretically according to the recommendations of the manufacturer of the Blot system (Novablot, LKB, Uppsala, Sweden). The blots were probed with a 1:200 dilution of the MAbs or a 1:400 dilution of the swine sera. Bound immunoglobulins were visualized by using peroxidase-labeled goat anti-mouse or goat antiswine immunoglobulins (Dakopatts) and HRP Color Development Reagent (Bio-Rad). Control blots were probed with buffer instead of MAb.

RESULTS

Hemolytic and cytotoxic activities.

Culture filtrates of all serotypes except of serotype 6 were cytotoxic and hemolytic (Table A). Hemolytic activity of culture filtrates of serotypes 2, 3, 4, 7, 8, and 12 were much weaker than those of serotypes 1, 5, 9, 10, and 11. All reference strains of *A. pleuropneumoniae* serotypes 1 to 12, including serotype 6, were hemolytic on blood agar. The hemolytic zones around colonies of serotypes 2, 3, 4, 7, 8, and 12 were much smaller than the zones around serotypes 1, 5, 9, 10, and 11. Hemolysis of serotype 6 could only be detected after removal of the colony.

Monoclonal antibodies and swine sera.

For this study we selected five MAbs and two swine sera. MAb CVI-Apcly 2.2 was raised against serotype 2 and tested in ELISA positive with serotype 2 and negative with serotype 9. MAbs CVI-Apcly 9.1 and 9.2 were raised against serotype 9 and tested positive with serotype 9 and negative with serotype 2. In contrast, the two swine sera and MAbs CVI-Apcly 9.3 and 9.4, which were also raised against serotype 9, tested positive with both serotype 2 and 9. The MAbs did not block each other in a competition ELISA, indicating that they recognized different epitopes.

Inhibition of hemolytic and cytotoxic activity.

MAbs and swine sera were tested for inhibition of hemolytic and cytotoxic activity of serotypes 1 to 12. MAb CVI-Apcly 9.1 and pig anti serotype 9 serum reduced the hemolytic activity of culture filtrates of serotypes 1, 5, 9, 10, and 11 with 80% or more. MAbs CVI-Apcly 9.3 and 9.4 and the swine sera against serotypes 2 and 9 totally reduced the hemolytic activity of the culture filtrates of serotypes 4, 7, and 12. Because the hemolytic activity of the culture filtrates of serotypes 2, 3, 6, and 8 was too weak to reliably determine inhibition of hemolysis in the liquid assay, we also tested the MAbs and swine sera for their ability to inhibit hemolysis on blood agar. The results of this test were similar to those of the liquid assay.

MAb CVI-Apcly 2.2 was raised against serotype 2 and inhibited cytotoxic activity of serotypes 2, 3, 4, and 8. MAb CVI-Apcly 9.1 was raised against serotype 9 and inhibited the hemolytic activity and the cytotoxic activity of serotypes 1, 5, 9, 10, and 11, suggesting that both activities are functions of the same protein. MAb CVI-Apcly 9.2 was also raised against serotype 9 and inhibited the cytotoxic but not the hemolytic activity of serotypes 1, 5, 9, 10, and 11. In contrast, MAbs CVI-Apcly 9.3 and 9.4, which were also raised against serotype 9, did not inhibit hemolytic or cytotoxic activity of these serotypes. Surprisingly, these two MAbs inhibited the hemolytic activity and cytotoxic activity of serotypes 7 and 12. This suggests that the hemolytic and cytotoxic activity of these serotypes are functions of the same protein. In addition, MAbs CVI-Apcly 9.3 and 9.4 inhibited the hemolytic but not the cytotoxic activity of serotypes 2, 3, 4, and 8.

Pig serum raised against serotype 2 inhibited the hemolytic and cytotoxic activity of serotypes 2, 3, 4, 6, 7, 8, and 12, whereas pig serum raised against serotype 9 inhibited the hemolytic and cytotoxic activity of serotypes 1, 5, 6, 7, 9, 10, 11, and 12 and the hemolytic but not the cytotoxic activity of serotypes 2, 3, 4, and 8.

Western blot analysis.

The selected MAbs and swine sera were used to probe Western blots of the culture filtrates of serotypes 1 to 12. MAb CVI-Apcly 2.2 reacted with a protein of approximately 120 kDa in filtrates of serotypes 2, 3, 4, and 8. MAbs CVI-Apcly 9.1 and 9.2 reacted with a protein of approximately 105 kDa in filtrates of serotypes 1, 5, 9, 10, and 11 and MAb CVI-Apcly 9.3 reacted with a protein also of approximately 105 kDa in filtrates of all serotypes except serotype 10. The reaction of MAb CVIApcly 9.3 with the proteins of serotypes 3, 6, and 8 was very weak and not always visible.

To test whether MAbs CVI-Apcly 2.2, 9.1, 9.2, and 9.3 recognized different proteins, we probed a blot with one MAb, washed the blot thoroughly, and then tested it with another MAb. This procedure was repeated until all four MAbs were tested. Three proteins became visible. One protein of approximately 120 kDa was detected by MAb CVI-Apcly 2.2 in serotypes 2, 3, 4, and 8; a second protein of approximately 105 kDa was detected by MAbs CVI-Apcly 9.1 and 9.2 in serotypes 1, 5, 9, 10, and 11; and a third protein of approximately 103 kDa was detected by MAb CVI-Apcly 9.3 in all serotypes except serotype 10 (Table A).

MAb CVI-Apcly 9.4 reacted with the 105 kDa protein and the 103 kDa protein, indicating that these two proteins have epitopes in common.

Western blot analysis using the swine sera confirmed the distribution of the three proteins among the 12 serotypes. Pig serum raised against serotype 2 recognized a protein of approximately 120 kDa in serotypes 2, 3, 4, and 8 and a protein of approximately 103 kDa in all serotypes except serotype 10. Pig serum raised serotype 9 recognized a protein of approximately 105 kDa in serotypes 1, 5, 9, 10, and 11, and a protein of approximately 103 kDa in all serotypes except serotype 10.

EXAMPLE 4

Production of Cytolysins and Preparation of a Recombinant Vaccine

Figure 9:
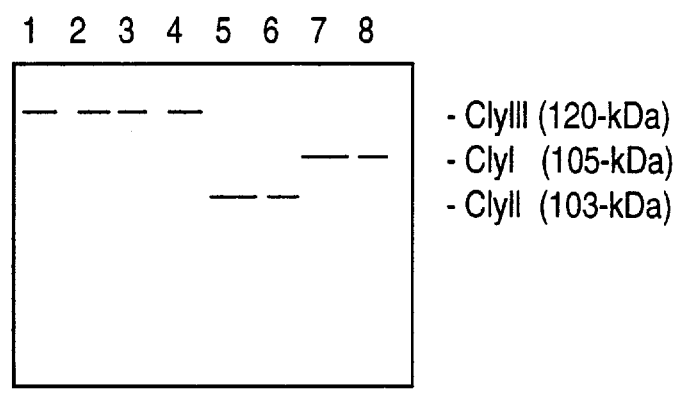
FIG. 9 illustrates the expression and secretion of cytolysins I, II, and III in recombinant *E. coli.*

Cells of *E. coli* strain LE 392 that contained plasmid pLG 575 (Gygi, D. et al. (1990) *Mol. Microbiol.* 4: 123–128) were transformed with plasmids that contained ClyI, ClyII, or ClyIII encoding genes. These cells were grown at 37° C. in Luria Broth medium, supplemented with the appropriate antibiotics and preferably with 10% Feutal Calf Serum, for about 6–8 h to an optical density at 620 nanometer of approximately 0.5. The culture was centrifuged, the supernatant was sterilized by treatment with a bacterio-staticum and stored. The proteins present in the culture supernatants and that reacted with a mixture of Mabs 9.1, 9.3 and 2.2 are shown in FIG. 9. The purified Cly proteins from those supernatants, or preferably the crude supernatants, are mixed in a predetermined ratio and subsequently mixed with an appropriate adjuvant and used for vaccination.

FIG. 9 is a diagrammatic representation of a Western blot showing expression and secretion of ClyIII (lanes 1–4), ClyII (lanes 5, 6) and ClyI lanes 7,8) by recombinant *E. coli* cells that contain the cytolysin gene in question together with transport genes of *E. coli* itself. The proteins were electrophoresed on SDS-PAGE, blotted on nitrocellulose and visualized with MAb 2.2, 9.1 and 9.3.

We claim:

1. A purified DNA nucleotide sequence comprising:
   (a) the nucleotide sequence set forth as SEQ ID NO's 1 or 3 which encodes a cytolytic protein of *Actinobacillus pleuropneumoniae;* or
   (b) a nucleotide sequence encoding a cytolytic protein of *Actinobacillus pleuropneumoniae,* the amino acid sequence of which is set forth as SEQ ID NO's 1 or 3.

2. The nucleotide sequence of claim 1, further comprising a nucleotide sequence encoding an activator protein, flanking at the 5' end the structural gene set forth as SEQ ID NO's 1 or 2.

3. The nucleotide sequence of claim 2, further comprising a nucleotide sequence encoding a transport protein, flanking at the 3' end the structural gene set forth as SEQ ID NO'S 1 or 2.

4. A vector comprising the nucleotide sequence of claim 1 linked to a promotor.

5. A vector according to claim 4, said nucleotide sequence being linked to an enhancer.

6. A recombinant host cell containing the nucleotide sequence of claim 1 and capable of expressing the polypeptide encoded by said nucleotide sequence.

* * * * *

UNITED STATES PATENT AND TRADEMARK OFFICE
CERTIFICATE OF CORRECTION

PATENT NO.  : 5,994,525
DATED       : November 30, 1999
INVENTOR(S) : Elbarte M. Kamp et al.

It is certified that error appears in the above-identified patent and that said Letters Patent is hereby corrected as shown below:

Title Page, [57] ABSTRACT, line 13 "proteins. another" should read --proteins.  Another--.

Column 5 Line 53 "TTATTT." should read --TTTATTT.--.

Column 6 Line 5 "clyICA" should read --clyIICA--.

Column 9 Line 15 "car be used" should read --can be used--.

Column 57 Line 25, Claim 2, "NO's 1 or 2." should read --NO's. 1 or 3.--.

Signed and Sealed this

Fifth Day of September, 2000

Attest:

Attesting Officer

Q. TODD DICKINSON

Director of Patents and Trademarks

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 8370
      (B) TYPE: nucleic acid
      (C) STRANDEDNESS: single
      (D) TOPOLOGY: linear (xi) SEQUENCE DESCRIPTION: SEQ ID NO: 1:

```
AGATTAATGA GCGATATTGT TATAAAATCA TAATGTAAAC CTCATTTGTA ATGAATTGGT        60

AAATTATATA ATAATCAAA AAACTTACTT TTTTTTATTT TTATCGGTAA GTATTTACA        120

TCAAGTCAGA CAAACGGCAA TATTGTTATA AATCTGGGGG GATGA                      165
```

| | | | | | | | | | | | | | | | | |
|---|---|---|---|---|---|---|---|---|---|---|---|---|---|---|---|---|
| ATG | AGT | AAA | AAA | ATT | AAT | GGA | TTT | GAG | GTT | TTA | GGA | GAG | GTG | GCA | | 210 |
| Met | Ser | Lys | Lys | Ile | Asn | Gly | Phe | Glu | Val | Leu | Gly | Glu | Val | Ala | | |
| 1 | | | | 5 | | | | | 10 | | | | | 15 | | |
| TGG | TTA | TGG | GCA | AGT | TCT | CCT | TTA | CAT | CGA | AAG | TGG | CCG | CTT | TCT | | 255 |
| Trp | Leu | Trp | Ala | Ser | Ser | Pro | Leu | His | Arg | Lys | Trp | Pro | Leu | Ser | | |
| | | | | 20 | | | | | 25 | | | | | 30 | | |
| TTG | TTA | GCA | ATT | AAT | GTG | CTA | CCT | GCG | ATT | GAG | AGT | AAT | CAA | TAT | | 300 |
| Leu | Leu | Ala | Ile | Asn | Val | Leu | Pro | Ala | Ile | Glu | Ser | Asn | Gln | Tyr | | |
| | | | | 35 | | | | | 40 | | | | | 45 | | |
| GTT | TTG | TTA | AAG | CGT | GAC | GGT | TTT | CCT | ATT | GCA | TTT | TGT | AGC | TGG | | 345 |
| Val | Leu | Leu | Lys | Arg | Asp | Gly | Phe | Pro | Ile | Ala | Phe | Cys | Ser | Trp | | |
| | | | | 50 | | | | | 55 | | | | | 60 | | |
| GCA | AAT | TTG | AAT | TTG | GAA | AAT | GAA | ATT | AAA | TAC | CTT | GAT | GAT | GTT | | 390 |
| Ala | Asn | Leu | Asn | Leu | Glu | Asn | Glu | Ile | Lys | Tyr | Leu | Asp | Asp | Val | | |
| | | | | 65 | | | | | 70 | | | | | 75 | | |
| GCC | TCG | CTA | GTT | GCG | GAT | GAT | TGG | ACT | TCC | GGC | GAT | CGT | CGA | TGG | | 435 |
| Ala | Ser | Leu | Val | Ala | Asp | Asp | Trp | Thr | Ser | Gly | Asp | Arg | Arg | Trp | | |
| | | | | 80 | | | | | 85 | | | | | 90 | | |
| TTT | ATA | GAT | TGG | ATA | GCA | CCG | TTC | GGA | GAC | AGT | GCC | GCA | TTA | TAC | | 480 |
| Phe | Ile | Asp | Trp | Ile | Ala | Pro | Phe | Gly | Asp | Ser | Ala | Ala | Leu | Tyr | | |
| | | | | 95 | | | | | 100 | | | | | 105 | | |
| AAA | CAT | ATG | CGA | GAT | AAC | TTC | CCG | AAT | GAG | CTG | TTT | AGG | GCT | ATT | | 525 |
| Lys | His | Met | Arg | Asp | Asn | Phe | Pro | Asn | Glu | Leu | Phe | Arg | Ala | Ile | | |
| | | | | 110 | | | | | 115 | | | | | 120 | | |
| CGA | GTT | GAT | CCG | GAC | TCT | CGA | GTA | GGG | AAA | ATT | TCA | GAA | TTT | CAT | | 570 |
| Arg | Val | Asp | Pro | Asp | Ser | Arg | Val | Gly | Lys | Ile | Ser | Glu | Phe | His | | |
| | | | | 125 | | | | | 130 | | | | | 135 | | |
| GGA | GGA | AAA | ATT | GAT | AAG | AAA | CTG | GCA | AGT | AAA | ATT | TTT | CAA | CAA | | 615 |
| Gly | Gly | Lys | Ile | Asp | Lys | Lys | Leu | Ala | Ser | Lys | Ile | Phe | Gln | Gln | | |
| | | | | 140 | | | | | 145 | | | | | 150 | | |
| TAT | CAC | TTT | GAA | TTA | ATG | AGT | GAG | CTA | AAA | AAT | AAA | CAA | AAT | TTT | | 660 |
| Tyr | His | Phe | Glu | Leu | Met | Ser | Glu | Leu | Lys | Asn | Lys | Gln | Asn | Phe | | |
| | | | | 155 | | | | | 160 | | | | | 165 | | |
| AAA | TTT | TCA | TTA | GTA | AAT | AGC | TAA | GGA | GAC | AAC | ATG | GCT | AAC | TCT | | 705 |
| Lys | Phe | Ser | Leu | Val | Asn | Ser | | | | | Met | Ala | Asn | Ser | | |
| | | | | 165 | | | | | | | 1 | | | | | |
| CAG | CTC | GAT | AGA | GTC | AAA | GGA | TTG | ATT | GAT | TCA | CTT | AAT | CAA | CAT | | 750 |
| Gln | Leu | Asp | Arg | Val | Lys | Gly | Leu | Ile | Asp | Ser | Leu | Asn | Gln | His | | |
| 5 | | | | 10 | | | | | 15 | | | | | | | |
| ACA | AAA | AGT | GCA | GCT | AAA | TCA | GGT | GCC | GGC | GCA | TTA | AAA | AAT | GGT | | 795 |
| Thr | Lys | Ser | Ala | Ala | Lys | Ser | Gly | Ala | Gly | Ala | Leu | Lys | Asn | Gly | | |
| 20 | | | | 25 | | | | | 30 | | | | | | | |
| TTG | GGA | CAG | GTG | AAG | CAA | GCA | GGG | CAG | AAA | TTA | ATT | TTA | TAT | ATT | | 840 |
| Leu | Gly | Gln | Val | Lys | Gln | Ala | Gly | Gln | Lys | Leu | Ile | Leu | Tyr | Ile | | |
| 35 | | | | 40 | | | | | 45 | | | | | | | |
| CCG | AAA | GAT | TAT | CAA | GCT | AGT | ACC | GGC | TCA | AGT | CTT | AAT | GAT | TTA | | 885 |
| Pro | Lys | Asp | Tyr | Gln | Ala | Ser | Thr | Gly | Ser | Ser | Leu | Asn | Asp | Leu | | |
| 50 | | | | 55 | | | | | 60 | | | | | | | |
| GTG | AAA | GCG | GCG | GAG | GCT | TTA | GGG | ATC | GAA | GTA | CAT | CGC | TCG | GAA | | 930 |
| Val | Lys | Ala | Ala | Glu | Ala | Leu | Gly | Ile | Glu | Val | His | Arg | Ser | Glu | | |
| 65 | | | | 70 | | | | | 75 | | | | | | | |
| AAA | AAC | GGT | ACC | GCA | CTA | GCG | AAA | GAA | TTA | TTC | GGT | ACA | ACG | GAA | | 975 |
| Lys | Asn | Gly | Thr | Ala | Leu | Ala | Lys | Glu | Leu | Phe | Gly | Thr | Thr | Glu | | |
| 80 | | | | 85 | | | | | 90 | | | | | | | |

-continued

```
AAA CTA TTA GGT TTC TCG GAA CGA GGC ATC GCA TTA TTT GCA CCT    1020
Lys Leu Leu Gly Phe Ser Glu Arg Gly Ile Ala Leu Phe Ala Pro
 95                 100                 105

CAG TTT GAT AAG TTA CTG AAT AAG AAC CAA AAA TTA AGT AAA TCG    1065
Gln Phe Asp Lys Leu Leu Asn Lys Asn Gln Lys Leu Ser Lys Ser
110                 115                 120

CTC GGC GGT TCA TCG GAA GCA TTA GGA CAA CGT TTA AAT AAA ACG    1110
Leu Gly Gly Ser Ser Glu Ala Leu Gly Gln Arg Leu Asn Lys Thr
125                 130                 135

CAA ACG GCA CTT TCA GCC TTA CAA AGT TTC TTA GGT ACG GCT ATT    1155
Gln Thr Ala Leu Ser Ala Leu Gln Ser Phe Leu Gly Thr Ala Ile
140                 145                 150

GCG GGT ATG GAT CTT GAT AGC CTG CTT CGT CGC CGT AGA AAC GGT    1200
Ala Gly Met Asp Leu Asp Ser Leu Leu Arg Arg Arg Arg Asn Gly
155                 160                 165

GAG GAC GTC AGT GGT TCG GAA TTA GCT AAA GCA GGT GTG GAT CTA    1245
Glu Asp Val Ser Gly Ser Glu Leu Ala Lys Ala Gly Val Asp Leu
170                 175                 180

GCC GCT CAG TTA GTG GAT AAC ATT GCA AGT GCA ACG GGT ACG GTG    1290
Ala Ala Gln Leu Val Asp Asn Ile Ala Ser Ala Thr Gly Thr Val
185                 190                 195

GAT GCG TTT GCC GAA CAA TTA GGT AAA TTG GGC AAT GCC TTA TCT    1335
Asp Ala Phe Ala Glu Gln Leu Gly Lys Leu Gly Asn Ala Leu Ser
200                 205                 210

AAC ACT CGC TTA AGC GGT TTA GCA AGT AAG TTA AAT AAC CTT CCA    1380
Asn Thr Arg Leu Ser Gly Leu Ala Ser Lys Leu Asn Asn Leu Pro
215                 220                 225

GAT TTA AGC CTT GCA GGA CCT GGG TTT GAT GCC GTA TCA GGT ATC    1425
Asp Leu Ser Leu Ala Gly Pro Gly Phe Asp Ala Val Ser Gly Ile
230                 235                 240

TTA TCT GTT GTT TCG GCT TCA TTC ATT TTA AGT AAT AAA GAT GCC    1470
Leu Ser Val Val Ser Ala Ser Phe Ile Leu Ser Asn Lys Asp Ala
245                 250                 255

GAT GCA GGT ACA AAA GCG GCG GCA GGT ATT GAA ATC TCA ACT AAA    1515
Asp Ala Gly Thr Lys Ala Ala Ala Gly Ile Glu Ile Ser Thr Lys
260                 265                 270

ATC TTA GGC AAT ATC GGT AAA GCG GTT TCT CAA TAT ATT ATT GCG    1560
Ile Leu Gly Asn Ile Gly Lys Ala Val Ser Gln Tyr Ile Ile Ala
275                 280                 285

CAA CGT GTG GCG GCA GGC TTA TCC ACA ACT GCG GCA ACC GGT GGT    1605
Gln Arg Val Ala Ala Gly Leu Ser Thr Thr Ala Ala Thr Gly Gly
290                 295                 300

TTA ATC GGT TCG GTC GTA GCA TTA GCG ATT AGC CCG CTT TCG TTC    1650
Leu Ile Gly Ser Val Val Ala Leu Ala Ile Ser Pro Leu Ser Phe
305                 310                 315

TTA AAT GTT GCG GAT AAG TTT GAA CGT GCG AAA CAG CTT GAA CAA    1695
Leu Asn Val Ala Asp Lys Phe Glu Arg Ala Lys Gln Leu Glu Gln
320                 325                 330

TAT TCG GAG CGC TTT AAA AAG TTC GGT TAT AAA GGT GAT AGT TTA    1740
Tyr Ser Glu Arg Phe Lys Lys Phe Gly Tyr Lys Gly Asp Ser Leu
335                 340                 345

TTA GCT TCA TTC TAC CGT GAA ACC GGT GCG ATT GAA GCG GCA TTA    1785
Leu Ala Ser Phe Tyr Arg Glu Thr Gly Ala Ile Glu Ala Ala Leu
350                 355                 360

ACC ACG ATT AAC AGT GTG TTA AGT GCG GCT TCC GCA GGT GTT GGG    1830
Thr Thr Ile Asn Ser Val Leu Ser Ala Ala Ser Ala Gly Val Gly
365                 370                 375

GCT GCT GCA ACC GGC TCA TTA GTC GGT GCG CCG GTA GCA GCT TTA    1875
Ala Ala Ala Thr Gly Ser Leu Val Gly Ala Pro Val Ala Ala Leu
380                 385                 390
```

```
GTT AGT GCA ATC ACC GGT ATT ATT TCA GGT ATT TTA GAT GCT TCT          1920
Val Ser Ala Ile Thr Gly Ile Ile Ser Gly Ile Leu Asp Ala Ser
395                 400                 405

AAA CAG GCA ATC TTC GAA CGA GTT GCA ACG AAA TTA GCG AAT AAG          1965
Lys Gln Ala Ile Phe Glu Arg Val Ala Thr Lys Leu Ala Asn Lys
410                 415                 420

ATT GAC GAA TGG GAG AAA AAA CAC GGT AAA AAC TAT TTT GAA AAC          2010
Ile Asp Glu Trp Glu Lys Lys His Gly Lys Asn Tyr Phe Glu Asn
425                 430                 435

GGT TAT GAC GCC CGC CAT TCC GCA TTC TTA GAA GAT ACC TTT GAA          2055
Gly Tyr Asp Ala Arg His Ser Ala Phe Leu Glu Asp Thr Phe Glu
440                 445                 450

TTG TTA TCA CAA TAC AAT AAA GAG TAT TCG GTA GAG CGT GTC GTT          2100
Leu Leu Ser Gln Tyr Asn Lys Glu Tyr Ser Val Glu Arg Val Val
455                 460                 465

GCT ATT ACG CAA CAG CGT TGG GAT GTC AAT ATC GGT GAA CTT GCC          2145
Ala Ile Thr Gln Gln Arg Trp Asp Val Asn Ile Gly Glu Leu Ala
470                 475                 480

GGC ATT ACT CGC AAA GGT TCT GAT ACG AAA AGC GGT AAA GCT TAC          2190
Gly Ile Thr Arg Lys Gly Ser Asp Thr Lys Ser Gly Lys Ala Tyr
485                 490                 495

GTT GAT TTC TTT GAA GAA GGA AAA CTT TTA GAG AAA GAA CCG GAT          2235
Val Asp Phe Phe Glu Glu Gly Lys Leu Leu Glu Lys Glu Pro Asp
500                 505                 510

CGT TTT GAT AAA AAA GTG TTT GAT CCG CTT GAA GGT AAA ATC GAC          2280
Arg Phe Asp Lys Lys Val Phe Asp Pro Leu Glu Gly Lys Ile Asp
515                 520                 525

CTT TCT TCA ATT AAC AAA ACC ACT TTA TTG AAA TTT GTT ACC CCG          2325
Leu Ser Ser Ile Asn Lys Thr Thr Leu Leu Lys Phe Val Thr Pro
530                 535                 540

GTC TTT ACC GCA GGT GAA GAG ATT CGT GAG CGT AAG CAA ACC GGT          2370
Val Phe Thr Ala Gly Glu Glu Ile Arg Glu Arg Lys Gln Thr Gly
545                 550                 555

AAA TAC GAA TAT ATG ACC GAA TTA TTC GTT AAA GGT AAA GAA AAA          2415
Lys Tyr Glu Tyr Met Thr Glu Leu Phe Val Lys Gly Lys Glu Lys
560                 565                 570

TGG GTG GTA ACC GGT GTG CAG TCA CAT AAT GCG ATT TAT GAC TAT          2460
Trp Val Val Thr Gly Val Gln Ser His Asn Ala Ile Tyr Asp Tyr
575                 580                 585

ACG AAT CTT ATC CAA TTA GCG ATA GAT AAA AAA GGT GAA AAA CGT          2505
Thr Asn Leu Ile Gln Leu Ala Ile Asp Lys Lys Gly Glu Lys Arg
590                 595                 600

CAA GTG ACC ATT GAA TCT CAT TTG GGT GAG AAA AAT GAT CGT ATA          2550
Gln Val Thr Ile Glu Ser His Leu Gly Glu Lys Asn Asp Arg Ile
605                 610                 615

TAT CTT TCA TCC GGT TCA TCT ATC GTA TAT GCG GGT AAC GGA CAT          2595
Tyr Leu Ser Ser Gly Ser Ser Ile Val Tyr Ala Gly Asn Gly His
620                 625                 630

GAT GTA GCA TAT TAC GAT AAA ACC GAT ACA GGT TAC TTA ACA TTT          2640
Asp Val Ala Tyr Tyr Asp Lys Thr Asp Thr Gly Tyr Leu Thr Phe
635                 640                 645

GAC GGA CAA AGT GCA CAG AAA GCC GGT GAA TAT ATT GTC ACT AAA          2685
Asp Gly Gln Ser Ala Gln Lys Ala Gly Glu Tyr Ile Val Thr Lys
650                 655                 660

GAA CTT AAA GCT GAT GTA AAA GTT TTA AAA GAA GTG GTT AAA ACT          2730
Glu Leu Lys Ala Asp Val Lys Val Leu Lys Glu Val Val Lys Thr
665                 670                 675

CAG GAT ATT TCA GTT GGA AAA CGC AGT GAA AAA TTA GAA TAT CGT          2775
Gln Asp Ile Ser Val Gly Lys Arg Ser Glu Lys Leu Glu Tyr Arg
680                 685                 690
```

```
GAT TAT GAG TTA AGC CCA TTC GAA CTT GGG AAC GGT ATC AGA GCT           2820
Asp Tyr Glu Leu Ser Pro Phe Glu Leu Gly Asn Gly Ile Arg Ala
695                 700                 705

AAA GAT GAA TTA CAT TCT GTT GAA GAA ATT ATC GGT AGT AAT CGT           2865
Lys Asp Glu Leu His Ser Val Glu Glu Ile Ile Gly Ser Asn Arg
710                 715                 720

AAA GAC AAA TTC TTT GGT AGT CGC TTT ACC GAT ATT TTC CAT GGT           2910
Lys Asp Lys Phe Phe Gly Ser Arg Phe Thr Asp Ile Phe His Gly
725                 730                 735

GCG AAA GGC GAT GAT GAA ATC TAC GGT AAT GAC GGC CAC GAT ATC           2955
Ala Lys Gly Asp Asp Glu Ile Tyr Gly Asn Asp Gly His Asp Ile
740                 745                 750

TTA TAC GGA GAC GAC GGT AAT GAT GTA ATC CAT GGC GGT GAC GGT           3000
Leu Tyr Gly Asp Asp Gly Asn Asp Val Ile His Gly Gly Asp Gly
755                 760                 765

AAC GAC CAT CTT GTT GGT GGT AAC GGA AAC GAC CGA TTA ATC GGC           3045
Asn Asp His Leu Val Gly Gly Asn Gly Asn Asp Arg Leu Ile Gly
770                 775                 780

GGA AAA GGT AAT AAT TTC CTT AAT GGC GGT GAT GGT GAC GAT GAG           3090
Gly Lys Gly Asn Asn Phe Leu Asn Gly Gly Asp Gly Asp Asp Glu
785                 790                 795

TTG CAG GTC TTT GAG GGT CAA TAC AAC GTA TTA TTA GGT GGT GCG           3135
Leu Gln Val Phe Glu Gly Gln Tyr Asn Val Leu Leu Gly Gly Ala
800                 805                 810

GGT AAT GAC ATT CTG TAT GGC AGC GAT GGT ACT AAC TTA TTT GAC           3180
Gly Asn Asp Ile Leu Tyr Gly Ser Asp Gly Thr Asn Leu Phe Asp
815                 820                 825

GGT GGT GTA GGC AAT GAC AAA ATC TAC GGT GGT TTA GGT AAG GAT           3225
Gly Gly Val Gly Asn Asp Lys Ile Tyr Gly Gly Leu Gly Lys Asp
830                 835                 840

ATT TAT CGC TAC AGT AAG GAG TAC GGT CGT CAT ATC ATT ATT GAG           3270
Ile Tyr Arg Tyr Ser Lys Glu Tyr Gly Arg His Ile Ile Ile Glu
845                 850                 855

AAA GGC GGT GAT GAT GAT ACG TTA TTG TTA TCG GAT CTT AGT TTT           3315
Lys Gly Gly Asp Asp Asp Thr Leu Leu Leu Ser Asp Leu Ser Phe
860                 865                 870

AAA GAT GTA GGA TTT ATC AGA ATC GGT GAT GAT CTT CTT GTG AAT           3360
Lys Asp Val Gly Phe Ile Arg Ile Gly Asp Asp Leu Leu Val Asn
875                 880                 885

AAA AGA ATC GGA GGA ACA CTG TAT TAC CAT GAA GAT TAC AAT GGG           3405
Lys Arg Ile Gly Gly Thr Leu Tyr Tyr His Glu Asp Tyr Asn Gly
890                 895                 900

AAT GCG CTC ACG ATT AAA GAT TGG TTC AAG GAA GGT AAA GAA GGA           3450
Asn Ala Leu Thr Ile Lys Asp Trp Phe Lys Glu Gly Lys Glu Gly
905                 910                 915

CAA AAT AAT AAA ATT GAA AAA ATC GTT GAT AAA GAT GGA GCT TAT           3495
Gln Asn Asn Lys Ile Glu Lys Ile Val Asp Lys Asp Gly Ala Tyr
920                 925                 930

GTT TTA AGC CAA TAT CTG ACT GAA CTG ACA GCT CCT GGA AGA GGT           3540
Val Leu Ser Gln Tyr Leu Thr Glu Leu Thr Ala Pro Gly Arg Gly
935                 940                 945

ATC AAT TAC TTT AAT GGG TTA GAA GAA AAA TTG TAT TAT GGA GAA           3585
Ile Asn Tyr Phe Asn Gly Leu Glu Glu Lys Leu Tyr Tyr Gly Glu
950                 955                 960

GGA TAT AAT GCA CTT CCT CAA CTC AGA AAA GAT ATT GAA CAA ATC           3630
Gly Tyr Asn Ala Leu Pro Gln Leu Arg Lys Asp Ile Glu Gln Ile
965                 970                 975

ATT TCA TCT ACG GGT GCA TTT ACC GGT GAT CAC GGA AAA GTA TCT           3675
Ile Ser Ser Thr Gly Ala Phe Thr Gly Asp His Gly Lys Val Ser
980                 985                 990
```

-continued

```
GTA GGC TCA GGC GGA CCG TTA GTC TAT AAT AAC TCA GCT AAC AAT           3720
Val Gly Ser Gly Gly Pro Leu Val Tyr Asn Asn Ser Ala Asn Asn
995              1000                1005

GTA GCA ATT CTT TGA GTTATTCTTT AGCACAAGCA GCTTAAGATA                  3765
Val Ala Ile Leu
1010

GTTATTTTTA GATGATAAAT AGCAATCCTA TATATATTAG GTGTGTAGGA                3815

TTGCTATTTT ATTTATGGAG GAGCAA              ATG GAT TTT TAT            3853
                                          Met Asp Phe Tyr
                                           1

CGG GAA GAA GAC TAC GGA TTA TAC GCA CTG ACG ATT TTA GCC CAG           3898
Arg Glu Glu Asp Tyr Gly Leu Tyr Ala Leu Thr Ile Leu Ala Gln
  5              10               15

TAC CAT AAT ATT GCT GTA AAT CCG GAA GAA CTA AAA CAT AAA TTC           3943
Tyr His Asn Ile Ala Val Asn Pro Glu Glu Leu Lys His Lys Phe
 20               25               30

GAC CTT GAA GGA AAA GGC TTA GAT CTA ACC GCT TGG CTA TTA GCC           3988
Asp Leu Glu Gly Lys Gly Leu Asp Leu Thr Ala Trp Leu Leu Ala
 35               40               45

GCA AAA TCA TTA GAA CTT AAA GCA AAA CAA GTA AAA AAA GCG ATT           4033
Ala Lys Ser Leu Glu Leu Lys Ala Lys Gln Val Lys Lys Ala Ile
 50               55               60

GAT CGT TTG GCG TTT ATC GCA CTA CCG GCA CTT GTA TGG CGA GAA           4078
Asp Arg Leu Ala Phe Ile Ala Leu Pro Ala Leu Val Trp Arg Glu
 65               70               75

GAC GGT AAA CAT TTT ATT TTG ACT AAA ATT GAT AAT GAA GCA AAA           4123
Asp Gly Lys His Phe Ile Leu Thr Lys Ile Asp Asn Glu Ala Lys
 80               85               90

AAA TAT TTA ATT TTT GAT TTG GAA ACG CAT AAT CCT CGC ATT TTG           4168
Lys Tyr Leu Ile Phe Asp Leu Glu Thr His Asn Pro Arg Ile Leu
 95              100              105

GAA CAA GCG GAA TTC GAG AGC TTA TAC CAA GGA AAA CTG ATT TTA           4213
Glu Gln Ala Glu Phe Glu Ser Leu Tyr Gln Gly Lys Leu Ile Leu
110              115              120

GTT GCA TCA AGA GCT TCC ATC GTA GGT AAG CTG GCA AAG TTT GAC           4258
Val Ala Ser Arg Ala Ser Ile Val Gly Lys Leu Ala Lys Phe Asp
125              130              135

TTC ACT TGG TTT ATA CCG GCG GTA ATT AAG TAT CGT AAG ATT TTT           4303
Phe Thr Trp Phe Ile Pro Ala Val Ile Lys Tyr Arg Lys Ile Phe
140              145              150

ATT GAA ACG TTA ATT GTT TCA ATT TTT TTG CAA ATT TTC GCA CTA           4348
Ile Glu Thr Leu Ile Val Ser Ile Phe Leu Gln Ile Phe Ala Leu
155              160              165

ATT ACA CCG CTT TTT TTC CAA GTC GTG ATG GAT AAA GTC TTG GTA           4393
Ile Thr Pro Leu Phe Phe Gln Val Val Met Asp Lys Val Leu Val
170              175              180

CAC CGA GGT TTT TCA ACC TTA AAT GTG ATT ACG GTG GCA TTA GCG           4438
His Arg Gly Phe Ser Thr Leu Asn Val Ile Thr Val Ala Leu Ala
185              190              195

ATC GTC GTG CTG TTT GAA ATT GTG CTA AAC GGT TTA CGT ACC TAT           4483
Ile Val Val Leu Phe Glu Ile Val Leu Asn Gly Leu Arg Thr Tyr
200              205              210

ATT TTT GCG CAT AGT ACC AGC CGT ATT GAT GTG GAG TTG GGA GCA           4528
Ile Phe Ala His Ser Thr Ser Arg Ile Asp Val Glu Leu Gly Ala
215              220              225

AGA TTA TTC AGA CAT TTA TTA GCA CTC CCA ATC TCT TAT TTT GAA           4573
Arg Leu Phe Arg His Leu Leu Ala Leu Pro Ile Ser Tyr Phe Glu
230              235              240

AAT CGT CGA GTC GGC GAT ACG GTG GCT CGT GTA CGA GAA CTC GAT           4618
```

-continued

| | | |
|---|---|---|
| Asn Arg Arg Val Gly Asp Thr Val Ala Arg Val Arg Glu Leu Asp<br>245 250 255 | | |
| CAA ATT CGT AAC TTC TTA ACC GGG CAG GCA CTT ACT TCC GTG TTG<br>Gln Ile Arg Asn Phe Leu Thr Gly Gln Ala Leu Thr Ser Val Leu<br>260 265 270 | 4663 | |
| GAT TTA ATG TTT TCC TTT ATC TTC TTT GCA GTG ATG TGG TAT TAC<br>Asp Leu Met Phe Ser Phe Ile Phe Phe Ala Val Met Trp Tyr Tyr<br>275 280 285 | 4708 | |
| AGC CCT AAA CTT ACT CTT GTG ATT TTA GGC TCG TTA CCG TTT TAT<br>Ser Pro Lys Leu Thr Leu Val Ile Leu Gly Ser Leu Pro Phe Tyr<br>290 295 300 | 4753 | |
| ATG GGG TGG TCG ATT TTT ATC AGC CCT ATT TTA CGT CGC CGT TTA<br>Met Gly Trp Ser Ile Phe Ile Ser Pro Ile Leu Arg Arg Arg Leu<br>305 310 315 | 4798 | |
| GAT GAA AAA TTC GCA CGT GGT GCG GAC AAT CAG TCA TTC TTA GTG<br>Asp Glu Lys Phe Ala Arg Gly Ala Asp Asn Gln Ser Phe Leu Val<br>320 325 330 | 4843 | |
| GAA TCG GTG ACT GCA ATC AAT ACG ATT AAA GCG TTG GCG GTT ACC<br>Glu Ser Val Thr Ala Ile Asn Thr Ile Lys Ala Leu Ala Val Thr<br>335 340 345 | 4888 | |
| CCT CAA ATG ACT AAT ACC TGG GAT AAG CAA TTA GCC AGC TAT GTA<br>Pro Gln Met Thr Asn Thr Trp Asp Lys Gln Leu Ala Ser Tyr Val<br>350 355 360 | 4933 | |
| TCG GCG GGA TTC CGT GTA ACC ACA TTA GCT ACT ATC GGA CAG CAA<br>Ser Ala Gly Phe Arg Val Thr Thr Leu Ala Thr Ile Gly Gln Gln<br>365 370 375 | 4978 | |
| GGT GTA CAA TTT ATT CAA AAA GTC GTG ATG GTT ATT ACC TTA TGG<br>Gly Val Gln Phe Ile Gln Lys Val Val Met Val Ile Thr Leu Trp<br>380 385 390 | 5023 | |
| CTA GGC GCA CAT TTA GTG ATT TCA GGC GAT TTA AGT ATC GGA CAA<br>Leu Gly Ala His Leu Val Ile Ser Gly Asp Leu Ser Ile Gly Gln<br>395 400 405 | 5068 | |
| TTA ATC GCA TTT AAT ATG TTA TCC GGT CAA GTG ATT GCA CCG GTG<br>Leu Ile Ala Phe Asn Met Leu Ser Gly Gln Val Ile Ala Pro Val<br>410 415 420 | 5113 | |
| ATT CGT TTA GCG CAA CTT TGG CAA GAT TTC CAA CAA GTG GGA ATT<br>Ile Arg Leu Ala Gln Leu Trp Gln Asp Phe Gln Gln Val Gly Ile<br>425 430 435 | 5158 | |
| TCG GTA ACG CGT TTA GGT GAT GTT TTA AAC TCT CCG ACC GAG AGC<br>Ser Val Thr Arg Leu Gly Asp Val Leu Asn Ser Pro Thr Glu Ser<br>440 445 450 | 5203 | |
| TAT CAA GGA AAA TTG GCG TTA CCG GAA ATT AAA GGC GAT ATT ACC<br>Tyr Gln Gly Lys Leu Ala Leu Pro Glu Ile Lys Gly Asp Ile Thr<br>455 460 365 | 5248 | |
| TTC CGT AAT ATA CGC TTC CGC TAC AAA CCG GAT GCG CCG GTG ATT<br>Phe Arg Asn Ile Arg Phe Arg Tyr Lys Pro Asp Ala Pro Val Ile<br>470 475 480 | 5293 | |
| TTA AAT GAT GTG AAT TTA TCG ATT CAG CAA GGT GAA GTG ATC GGT<br>Leu Asn Asp Val Asn Leu Ser Ile Gln Gln Gly Glu Val Ile Gly<br>485 490 495 | 5338 | |
| ATC GTA GGA CGT TCA GGC TCA GGG AAG AGC ACC TTA ACG AAA TTA<br>Ile Val Gly Arg Ser Gly Ser Gly Lys Ser Thr Leu Thr Lys Leu<br>500 505 510 | 5383 | |
| ATT CAA CGT TTT TAT ATT CCG GAA AAC GGT CAG GTA TTA ATA GAT<br>Ile Gln Arg Phe Tyr Ile Pro Glu Asn Gly Gln Val Leu Ile Asp<br>515 520 525 | 5428 | |
| GGG CAT GAT TTA GCA TTG GCG GAT CCG AAC TGG CTA CGT CGT CAA<br>Gly His Asp Leu Ala Leu Ala Asp Pro Asn Trp Leu Arg Arg Gln<br>530 535 540 | 5473 | |
| GTC GGG GTG GTA TTA CAA GAT AAC GTA CTA TTA AAT CGT AGT ATT | 5518 | |

-continued

| | | |
|---|---|---|
| Val Gly Val Val Leu Gln Asp Asn Val Leu Leu Asn Arg Ser Ile<br>545                550                     555 | | |
| CGA GAT AAT ATT GCC TTA GCG GAT CCG GGT ATG CCA ATG GAA AAA<br>Arg Asp Asn Ile Ala Leu Ala Asp Pro Gly Met Pro Met Glu Lys<br>560                565                     570 | 5563 |
| ATT GTC CAT GCG GCA AAA TTA GCC GGC GCA CAT GAA TTT ATT TCT<br>Ile Val His Ala Ala Lys Leu Ala Gly Ala His Glu Phe Ile Ser<br>575                580                     585 | 5608 |
| GAA TTG CGT GAG GGA TAT AAC ACG ATT GTT GGT GAG CAA GGT GCG<br>Glu Leu Arg Glu Gly Tyr Asn Thr Ile Val Gly Glu Gln Gly Ala<br>590                595                     600 | 5653 |
| GGG CTA TCT GGC GGG CAA CGC CAA CGT ATT GCG ATT GCA CGC GCT<br>Gly Leu Ser Gly Gly Gln Arg Gln Arg Ile Ala Ile Ala Arg Ala<br>605                610                     615 | 5698 |
| TTG GTG AAT AAC CCG AAA ATC TTA ATT TTT GAT GAA GCG ACC AGC<br>Leu Val Asn Asn Pro Lys Ile Leu Ile Phe Asp Glu Ala Thr Ser<br>620                625                     630 | 5743 |
| GCA TTA GAT TAT GAA TCC GAG CAT ATC ATC ATG CGC AAT ATG CAC<br>Ala Leu Asp Tyr Glu Ser Glu His Ile Ile Met Arg Asn Met His<br>635                640                     645 | 5788 |
| CAG ATT TGT AAA GGG AGA ACG GTA ATT ATC ATT GCA CAC CGT TTA<br>Gln Ile Cys Lys Gly Arg Thr Val Ile Ile Ile Ala His Arg Leu<br>650                655                     660 | 5833 |
| TCT ACG GTA AAA AAT GCC GAC CGT ATT ATT GTG ATG GAA AAA GGT<br>Ser Thr Val Lys Asn Ala Asp Arg Ile Ile Val Met Glu Lys Gly<br>665                670                     675 | 5878 |
| CAG ATT GTG GAA CAA GGT AAG CAT AAA GAG CTG CTT GCT GAT CCA<br>Gln Ile Val Glu Gln Gly Lys His Lys Glu Leu Leu Ala Asp Pro<br>680                685                     690 | 5923 |
| AAC GGC TTA TAT CAC TAC TTA CAC CAA TTA CAA TCG GAA TAG GAGGA<br>Asn Gly Leu Tyr His Tyr Leu His Gln Leu Gln Ser Glu<br>695                700                     705 | 5970 |
| CTT ATG AAA ACT TGG CTA ATG GGT TTA TAT GAG TTT TTC CAA CGC<br>    Met Lys Thr Trp Leu Met Gly Leu Tyr Glu Phe Phe Gln Arg<br>      1                     5                       10 | 6015 |
| TAT AAA ACG GTT TGG ACG GAG ATC TGG AAA ATT CGT CAT CAA TTG<br>Tyr Lys Thr Val Trp Thr Glu Ile Trp Lys Ile Arg His Gln Leu<br>15                20                     25 | 6060 |
| GAT ACG CCG GAT CGA GAA AAG GAT GAA AAT GAA TTT TTA CCT GCA<br>Asp Thr Pro Asp Arg Glu Lys Asp Glu Asn Glu Phe Leu Pro Ala<br>30                35                     40 | 6105 |
| CAC TTA GAG CTG ATT GAA ACA CCG GTG TCA AAA AAA CCG AGA TTG<br>His Leu Glu Leu Ile Glu Thr Pro Val Ser Lys Lys Pro Arg Leu<br>45                50                     55 | 6150 |
| ATC GCT TAT TTA ATT ATG CTG TTC CTA TTT TTG GCA TTA GTT ATT<br>Ile Ala Tyr Leu Ile Met Leu Phe Leu Phe Leu Ala Leu Val Ile<br>60                65                     70 | 6195 |
| TCA ATT GTC AGT CAC GTA GAA ATT GTG GCG ACC GCA ACG GGT AAA<br>Ser Ile Val Ser His Val Glu Ile Val Ala Thr Ala Thr Gly Lys<br>75                80                     85 | 6240 |
| TTA GCG TTT AGC GAC CGT AGC AAA GAA ATT AAG CCG ATT GAA AAC<br>Leu Ala Phe Ser Asp Arg Ser Lys Glu Ile Lys Pro Ile Glu Asn<br>90                95                     100 | 6285 |
| GCC TTG GTT AAA GAA ATC TTT GTG CAA GAC GGA CAA TTT GTT GAG<br>Ala Leu Val Lys Glu Ile Phe Val Gln Asp Gly Gln Phe Val Glu<br>105                110                     115 | 6330 |
| AAA GAT CAG TTG CTG TTA CAC TTG ACC GCA TTG GGA GCC GAT GCG<br>Lys Asp Gln Leu Leu Leu His Leu Thr Ala Leu Gly Ala Asp Ala<br>120                125                     130 | 6375 |
| GAT CAA CAA AAA ACC AAA AGT TCG TTA TCG CTG ACT AAA TTG GAA | 6420 |

```
Asp Gln Gln Lys Thr Lys Ser Ser Leu Ser Leu Thr Lys Leu Glu
135                 140                 145

CGT TAT CGT TAT GAA ATT TTA TTA GAG GCG GTT GCG GCG GAT AGG         6465
Arg Tyr Arg Tyr Glu Ile Leu Leu Glu Ala Val Ala Ala Asp Arg
150                 155                 160

TTG CCG CTC ATT GAA CTG ACA AAG GAT GAA TTT AAA CAT GCT ACG         6510
Leu Pro Leu Ile Glu Leu Thr Lys Asp Glu Phe Lys His Ala Thr
165                 170                 175

GAA GAA GAT AAA ACC AGA ATT CGC TAT TTG ATC ACC GAG CAA TTT         6555
Glu Glu Asp Lys Thr Arg Ile Arg Tyr Leu Ile Thr Glu Gln Phe
180                 185                 190

GAA GCT TGG CAA AAG CAA AAG TAT CAA AAA GAA TTA GCT TTG CAA         6600
Glu Ala Trp Gln Lys Gln Lys Tyr Gln Lys Glu Leu Ala Leu Gln
195                 200                 205

CGT AGA GAA GCA GAA AAA CAA ACG GTT CTA GCT AAT ATT CGT AAA         6645
Arg Arg Glu Ala Glu Lys Gln Thr Val Leu Ala Asn Ile Arg Lys
210                 215                 220

TAT GAG GGA ATC AGT CGA GTT GAA AAT GAA AGA TTA AAA GAT CTT         6690
Tyr Glu Gly Ile Ser Arg Val Glu Asn Glu Arg Leu Lys Asp Leu
225                 230                 235

AAA AAA TTA TTT AAT TCG AAA TCG ACT TCT AAA CAT GAT GTC TTG         6735
Lys Lys Leu Phe Asn Ser Lys Ser Thr Ser Lys His Asp Val Leu
240                 245                 250

ACT CAA GAA AAT CGT CAT ATC GAA GCG GTA AAT GAG TTG GCG GTG         6780
Thr Gln Glu Asn Arg His Ile Glu Ala Val Asn Glu Leu Ala Val
255                 260                 265

TAT AAA TCT CGG TTG AAT GAA GTG GAA AGT GAC TTA CGT CAA GCC         6825
Tyr Lys Ser Arg Leu Asn Glu Val Glu Ser Asp Leu Arg Gln Ala
270                 275                 280

AAA GAG GAA ATA CAT TTA ATA ACT CAG TTG TTT AGA GCC GAT ATT         6870
Lys Glu Glu Ile His Leu Ile Thr Gln Leu Phe Arg Ala Asp Ile
285                 290                 295

CTG GAG AAG TTG AAA CAA AAT GTT GAA GCG GAG AAA CAG CTT TCG         6915
Leu Glu Lys Leu Lys Gln Asn Val Glu Ala Glu Lys Gln Leu Ser
300                 305                 310

CTC GAA TTA GAA AAA AAT GAG CAG CGT CAA ATT GCT TCG GTG ATT         6960
Leu Glu Leu Glu Lys Asn Glu Gln Arg Gln Ile Ala Ser Val Ile
315                 320                 325

CGT GCG CCG GTT TCC GGT ACG GTT CAG CAA CTT AAA ACC CAT ACG         7005
Arg Ala Pro Val Ser Gly Thr Val Gln Gln Leu Lys Thr His Thr
330                 335                 340

GTA GGC GGC GTC GTG ACG ACT GCC GAA ACC TTG ATG GTA ATT GCT         7050
Val Gly Gly Val Val Thr Thr Ala Glu Thr Leu Met Val Ile Ala
345                 350                 355

CCG GAA GAT GAT GTT TTA GAG GTA ACG GCG TTA ATT CAA AAT AAG         7095
Pro Glu Asp Asp Val Leu Glu Val Thr Ala Leu Ile Gln Asn Lys
360                 365                 370

GAT ATC GGT TTT ATC GAG GTC GGT CAG GAT GCG GTG ATT AAA GTA         7140
Asp Ile Gly Phe Ile Glu Val Gly Gln Asp Ala Val Ile Lys Val
375                 380                 385

GAA ACT TTT CCT TAT ACT CGT TAC GGC TAT TTA ATG GGT AAA GTA         7185
Glu Thr Phe Pro Tyr Thr Arg Tyr Gly Tyr Leu Met Gly Lys Val
390                 395                 400

AAA AAT ATC ACG CTG GAA GCC ATC GAA CAT CCG CAA CTC GGT CTA         7230
Lys Asn Ile Thr Leu Glu Ala Ile Glu His Pro Gln Leu Gly Leu
405                 410                 415

GTT TTT AAC TCG ATT ATT TCT ATT GAT AGA AAA ACT TTA TCC GGC         7275
Val Phe Asn Ser Ile Ile Ser Ile Asp Arg Lys Thr Leu Ser Gly
420                 425                 430

AAA GAC GGC AAA GAA ATT GAA CTT GGA TCA GGT ATG AGT GTG ACG         7320
```

```
Lys Asp Gly Lys Glu Ile Glu Leu Gly Ser Gly Met Ser Val Thr
435                 440                 445

GCG GAA ATT AAA ACT GGA GAA CGT AGC GTT ATT AGT TAT TTA CTC      7365
Ala Glu Ile Lys Thr Gly Glu Arg Ser Val Ile Ser Tyr Leu Leu
450                 455                 460

AGT CCG TTG GAA GAA TCC GTT TCG GAG AGT TTA AGA GAA CGC TAA      7410
Ser Pro Leu Glu Glu Ser Val Ser Glu Ser Leu Arg Glu Arg
465                 470                 475

AGCAGATAAA ACAAGCGGCC ATATTTTCTT ACTTTTTTGC AAAAAACGTA TGAAATAT    7470

CCGCTTGTCG TTTGTAAAAG ACTATTTATT TACAATAATT TTAGCACCGT TAGAAAAT    7530

GATCTGACGA GCTTCAAATT GAGCGGAGAG CTGTGCTTGC GGGTTTAGAA ATACGGCT    7590

TGCTTCTTGC GGTAAGTCTG AAACCGGTAC GCAAAGGCAA GTTCCGCCGT GGTTTGGC    7650

TTTAAGTTAT CTTTAAAGGT AACGGGCGCA TCTTGCGTGA GGATAACTTT ATCATTGT    7710

ACATAGTTTA CCGCCCATTG AACGATACGA ATATTGCGTT TGGTTTTATT TTCAATAC    7770

TATTTAAAGC TAACCATCGG CTGCCCTTCT TTATTTTTAG CCAATTCATA ACCGAAAA    7830

CGTAACCCGA TACTGTCATT AAATTGTTTA AGGCGTTTTT CTTTAGCCGA AAGAGGTG    7890

TTTTTCGTTA CTGATTTATG TTCAACCGTC GGTTGAATTT TATTGCCTTC AGCTTGAG    7950

TTAAACGCTA AAAAGAATGA TGCTACCGCC GTGCTAAGTA ATTTAATGTG TTTCATAA    8010

CACCTCGTAA TGAGAGCTAA AAGCCGACTT GATATATTAC GCTATATATT GTCAGATT    8070

CGGCACAGTT GCAATGACCG CATAACCGTC CGATTCGGCA ATAATCTCGA CTTGGCTT    8130

CGCCGCAATG AAAATCGCTT CGCCTTGTTG GAGATAAATG GACTCTTCAC CGAGGTCG    8190

ATAGATACTG CCTTTCATCA CCAATAAGAT ACTTGCACAG TCGGCCGTAA AGTTTTCT    8250

GTCAAATGCG TTGAATTGCA TATGTTGCAA TGCAAAATCT TTCGCTTCAG GCGTCGGA    8310

AAGATGAATG AAACCGTCGT TTTCTTGATA AGGCGGAATA ACTTCGGGGT AATCGGGC    8370

(2) INFORMATION FOR SEQ ID NO: 2:

(i) SEQUENCE CHARACTERISTICS:
        (A) LENGTH: 4731
        (B) TYPE: nucleic acid
        (C) STRANDEDNESS: single
        (D) TOPOLOGY: linear (xi) SEQUENCE DESCRIPTION: SEQ ID NO: 2:

CTTAACCATT ACAGAACGTT GGTACAAAAA ATTTTACAGG AAAATGATGG ATAGTCCTTA     60

ACAAAAATTA ATGTTTTATT TCCTATAAAA CATCCGACCA GTATTATTTT TGATTAAAA    120

AAGAACAAAC AGATCATGAC AAACGTTTGC CTTGTTTTCC TTCACAAAAA TATTATGGT    180

TTTTATTTAG AATAAATTAT CTATATTCAT TTTTTAGGGA ATGGGAGGGA TG          232

ATG CTA AAA AAT GAT TTT AAC GTA TTG GGA CAA ATT GCT TGG TTA        277
Met Leu Lys Asn Asp Phe Asn Val Leu Gly Gln Ile Ala Trp Leu
1               5                   10                  15

TGG GCA AAT TCT CCA ATG CAC CGA AAT TGG TCA GTT TCA CTG TTA        322
Trp Ala Asn Ser Pro Met His Arg Asn Trp Ser Val Ser Leu Leu
                20                  25                  30

ATG AAG AAT GTT ATT CCT GCA ATT GAA AAT GAC CAA TAT TTG TTA        367
Met Lys Asn Val Ile Pro Ala Ile Glu Asn Asp Gln Tyr Leu Leu
                35                  40                  45

CTA GTT GAT GAT GGT TTT CCT ATT GCA TAT TGC AGT TGG GCC AAA        412
Leu Val Asp Asp Gly Phe Pro Ile Ala Tyr Cys Ser Trp Ala Lys
                50                  55                  60

TTA ACT CTA GAG AGT GAG GCT CGC TAT GTA AAG GAC ACC AAT TCA        457
Leu Thr Leu Glu Ser Glu Ala Arg Tyr Val Lys Asp Thr Asn Ser
```

-continued

```
                     65                   70                   75
TTA AAA ATA GAT GAT TGG AAT GCA GGA GAT CGT ATA TGG ATC ATT         502
Leu Lys Ile Asp Asp Trp Asn Ala Gly Asp Arg Ile Trp Ile Ile
                         80                   85                   90

GAT TGG ATT GCC CCA TTC GGG GAT TCA TCT CTA TTG TAT AAA CAT         547
Asp Trp Ile Ala Pro Phe Gly Asp Ser Ser Leu Leu Tyr Lys His
                 95                  100                  105

ATG AGA CAA CGT TTT CCA TAC GAT ATT GGA AGG GCA ATT AGA ATC         592
Met Arg Gln Arg Phe Pro Tyr Asp Ile Gly Arg Ala Ile Arg Ile
             110                  115                  120

TAT CCT AGC AAA AAA GAT ACT GGA AAA ATC ATA TAT TTA AAA GGA         637
Tyr Pro Ser Lys Lys Asp Thr Gly Lys Ile Ile Tyr Leu Lys Gly
                     125                  130                  135

GGA AAA ATA ACA AAA AAA GTA GCT GAA AAG ACA TTT CTT CAG TAT         682
Gly Lys Ile Thr Lys Lys Val Ala Glu Lys Thr Phe Leu Gln Tyr
                 140                  145                  150

GAG CAA GAG TTA ATA ACA GCT CTA CAA TAATATCTTT AAATGATCAA           729
Glu Gln Glu Leu Ile Thr Ala Leu Gln
             155

TTATATAAAG GAGACTCTTTT          ATG TCA AAA ATC ACT TTG TCA TCA     774
                                Met Ser Lys Ile Thr Leu Ser Ser
                                 1                   5

TTA AAA TCG TCC TTA CAA CAA GGA TTG AAA AAT GGG AAA AAC AAG         819
Leu Lys Ser Ser Leu Gln Gln Gly Leu Lys Asn Gly Lys Asn Lys
         10                   15                   20

TTA AAT CAA GCA GGT ACA ACA CTG AAG AAT GGT TTA ACT CAA ACT         864
Leu Asn Gln Ala Gly Thr Thr Leu Lys Asn Gly Leu Thr Gln Thr
     25                   30                   35

GGT CAT TCT CTA CAG AAT GGG GCT AAA AAA TTA ATC TTA TAT ATT         909
Gly His Ser Leu Gln Asn Gly Ala Lys Lys Leu Ile Leu Tyr Ile
 40                   45                   50

CCT CAA GGC TAT GAT TCG GGT CAA GGA AAT GGA GTT CAA GAT TTA         954
Pro Gln Gly Tyr Asp Ser Gly Gln Gly Asn Gly Val Gln Asp Leu
                 55                   60                   65

GTT AAA GCT GCT AAT GAT TTA GGT ATT GAA GTA TGG CGA GAA GAA         999
Val Lys Ala Ala Asn Asp Leu Gly Ile Glu Val Trp Arg Glu Glu
             70                   75                   80

CGC AGC AAT TTG GAC ATT GCA AAA ACT AGC TTT GAT ACA ACT CAG         1044
Arg Ser Asn Leu Asp Ile Ala Lys Thr Ser Phe Asp Thr Thr Gln
         85                   90                   95

AAA ATT CTA GGT TTT ACT GAT AGA GGA ATT GTA TTA TTT GCA CCT         1089
Lys Ile Leu Gly Phe Thr Asp Arg Gly Ile Val Leu Phe Ala Pro
     100                  105                  110

CAG CTA GAT AAT TTA TTA AAG AAG AAT CCT AAA ATT GGC AAT ACA         1134
Gln Leu Asp Asn Leu Leu Lys Lys Asn Pro Lys Ile Gly Asn Thr
 115                  120                  125

TTA GGA AGT GCT TCT AGC ATC TCA CAA AAT ATA GGT AAA GCC AAT         1179
Leu Gly Ser Ala Ser Ser Ile Ser Gln Asn Ile Gly Lys Ala Asn
                 130                  135                  140

ACT GTA TTA GGT GGT ATT CAA TCT ATT TTA GGA TCT GTT TTA TCT         1224
Thr Val Leu Gly Gly Ile Gln Ser Ile Leu Gly Ser Val Leu Ser
             145                  150                  155

GGA GTA AAT CTG AAT GAA TTA CTT CAA AAT AAA GAT CCT AAT CAA         1269
Gly Val Asn Leu Asn Glu Leu Leu Gln Asn Lys Asp Pro Asn Gln
         160                  165                  170

TTA GAA CTT GCA AAA GCA GGG CTA GAA CTG ACT AAT GAA TTA GTT         1314
Leu Glu Leu Ala Lys Ala Gly Leu Glu Leu Thr Asn Glu Leu Val
     175                  180                  185

GGT AAT ATT GCT AGC TCG GTG CAA ACT GTA GAT GCA TTT GCA GAA         1359
Gly Asn Ile Ala Ser Ser Val Gln Thr Val Asp Ala Phe Ala Glu
```

-continued

|  |  |  |  |  |
|---|---|---|---|---|
| | 190 | 195 | 200 | |
| CAA ATA TCT AAA CTA GGT TCA CAT TTA CAG AAT GTG AAA GGA TTA | | | | 1404 |
| Gln Ile Ser Lys Leu Gly Ser His Leu Gln Asn Val Lys Gly Leu | | | | |
| 205 | 210 | | 215 | |
| GGA GGA TTG AGT AAT AAA TTA CAA AAT CTA CCA GAT CTA GGA AAA | | | | 1449 |
| Gly Gly Leu Ser Asn Lys Leu Gln Asn Leu Pro Asp Leu Gly Lys | | | | |
| 220 | | 225 | 230 | |
| GCA AGT TTA GGT TTG GAC ATT ATC TCT GGT TTA CTT TCT GGA GCA | | | | 1494 |
| Ala Ser Leu Gly Leu Asp Ile Ile Ser Gly Leu Leu Ser Gly Ala | | | | |
| 235 | | 240 | 245 | |
| TCT GCA GGT CTC ATT TTA GCA GAT AAA GAG GCT TCA ACA GAA AAG | | | | 1539 |
| Ser Ala Gly Leu Ile Leu Ala Asp Lys Glu Ala Ser Thr Glu Lys | | | | |
| 250 | | 255 | 260 | |
| AAA GCT GCC GCA GGT GTA GAA TTT GCT AAC CAA ATT ATA GGT AAT | | | | 1584 |
| Lys Ala Ala Ala Gly Val Glu Phe Ala Asn Gln Ile Ile Gly Asn | | | | |
| 265 | | 270 | 275 | |
| GTA ACA AAA GCG TCA TCT TAC ATT CTT GCC CAA CGA GTC GCT | | | | 1629 |
| Val Thr Lys Ala Val Ser Ser Tyr Ile Leu Ala Gln Arg Val Ala | | | | |
| 280 | | 285 | 290 | |
| TCA GGT TTG TCT TCA ACT GGT CCT GTC GCT GCA TTA ATC GCA TCT | | | | 1674 |
| Ser Gly Leu Ser Ser Thr Gly Pro Val Ala Ala Leu Ile Ala Ser | | | | |
| 295 | | 300 | 305 | |
| ACA GTT GCA CTA GCT GTT AGC CCT CTT TCA TTC TTA AAT GTA GCT | | | | 1719 |
| Thr Val Ala Leu Ala Val Ser Pro Leu Ser Phe Leu Asn Val Ala | | | | |
| 310 | | 315 | 320 | |
| GAT AAG TTT AAA CAA GCT GAT TTA ATC AAA TCA TAT TCT GAA CGC | | | | 1764 |
| Asp Lys Phe Lys Gln Ala Asp Leu Ile Lys Ser Tyr Ser Glu Arg | | | | |
| 325 | | 330 | 335 | |
| TTC CAA AAA TTA GGA TAT GAT GGA GAT CGT TTA TTA GCT GAT TTT | | | | 1809 |
| Phe Gln Lys Leu Gly Tyr Asp Gly Asp Arg Leu Leu Ala Asp Phe | | | | |
| 340 | | 345 | 350 | |
| CAC CGT GAG ACA GGA ACT ATT GAT GCT TCT GTA ACA ACA ATT AAC | | | | 1854 |
| His Arg Glu Thr Gly Thr Ile Asp Ala Ser Val Thr Thr Ile Asn | | | | |
| 355 | | 360 | 365 | |
| ACT GCT TTA GCA GCT ATC TCC GGT GGA GTT GGA GCT GCA AGC GCG | | | | 1899 |
| Thr Ala Leu Ala Ala Ile Ser Gly Gly Val Gly Ala Ala Ser Ala | | | | |
| 370 | | 375 | 380 | |
| GGT TCT CTA GTC GGA GCT CCA GTT GCG TTA CTC GTT GCT GGT GTT | | | | 1944 |
| Gly Ser Leu Val Gly Ala Pro Val Ala Leu Leu Val Ala Gly Val | | | | |
| 385 | | 390 | 395 | |
| ACG GGA CTT ATT ACA ACT ATT CTA GAA TAT TCT AAA CAA GCC ATG | | | | 1989 |
| Thr Gly Leu Ile Thr Thr Ile Leu Glu Tyr Ser Lys Gln Ala Met | | | | |
| 400 | | 405 | 410 | |
| TTT GAA CAT GTT GCA AAT AAG GTT CAT GAC AGA ATA GTT GAA TGG | | | | 2034 |
| Phe Glu His Val Ala Asn Lys Val His Asp Arg Ile Val Glu Trp | | | | |
| 415 | | 420 | 425 | |
| GAG AAA AAA CAT AAT AAA AAC TAT TTT GAG CAA GGT TAT GAT TCT | | | | 2079 |
| Glu Lys Lys His Asn Lys Asn Tyr Phe Glu Gln Gly Tyr Asp Ser | | | | |
| 430 | | 435 | 440 | |
| CGT CAT TTA GCT GAT TTA CAA GAC AAT ATG AAG TTT CTT ATC AAT | | | | 2124 |
| Arg His Leu Ala Asp Leu Gln Asp Asn Met Lys Phe Leu Ile Asn | | | | |
| 445 | | 450 | 455 | |
| TTA AAT AAA GAA CTT CAG GCT GAA CGC GTA GTA GCT ATT ACC CAA | | | | 2169 |
| Leu Asn Lys Glu Leu Gln Ala Glu Arg Val Val Ala Ile Thr Gln | | | | |
| 460 | | 465 | 470 | |
| CAA AGA TGG GAT AAC CAA ATT GGA GAC CTA GCG GCA ATT AGC CGT | | | | 2214 |
| Gln Arg Trp Asp Asn Gln Ile Gly Asp Leu Ala Ala Ile Ser Arg | | | | |
| 475 | | 480 | 485 | |
| AGA ACG GAT AAA ATT TCC AGT GGA AAA GCT TAT GTG GAT GCT TTT | | | | 2259 |
| Arg Thr Asp Lys Ile Ser Ser Gly Lys Ala Tyr Val Asp Ala Phe | | | | |

```
                      490                 495                 500
GAG GAG GGG CAA CAC CAG TCC TAC GAT TCA TCC GTA CAG CTA GAT           2304
Glu Glu Gly Gln His Gln Ser Tyr Asp Ser Ser Val Gln Leu Asp
    505                 510                 515

AAC AAA AAC GGT ATT ATT AAT ATT AGT AAT ACA AAT AGA AAG ACA           2349
Asn Lys Asn Gly Ile Ile Asn Ile Ser Asn Thr Asn Arg Lys Thr
    520                 525                 530

CAA AGT GTT TTA TTC AGA ACT CCA TTA CTA ACT CCA GGT GAA GAG           2394
Gln Ser Val Leu Phe Arg Thr Pro Leu Leu Thr Pro Gly Glu Glu
    535                 540                 545

AAT CGG GAA CGT ATT CAG GAA GGT AAA AAT TCT TAT ATT ACA AAA           2439
Asn Arg Glu Arg Ile Gln Glu Gly Lys Asn Ser Tyr Ile Thr Lys
    550                 555                 560

TTA CAT ATA CAA AGA GTT GAC AGT TGG ACT GTA ACA GAT GGT GAT           2484
Leu His Ile Gln Arg Val Asp Ser Trp Thr Val Thr Asp Gly Asp
    565                 570                 575

GCT AGC TCA AGC GTA GAT TTC ACT AAT GTA GTA CAA CGA ATC GCT           2529
Ala Ser Ser Ser Val Asp Phe Thr Asn Val Val Gln Arg Ile Ala
    580                 585                 590

GTG AAA TTT GAT GAT GCA GGT AAC ATT ATA GAA TCT AAA GAT ACT           2574
Val Lys Phe Asp Asp Ala Gly Asn Ile Ile Glu Ser Lys Asp Thr
    595                 600                 605

AAA ATT ATC GCA AAT TTA GGT GCT GGT AAC GAT AAT GTA TTT GTT           2619
Lys Ile Ile Ala Asn Leu Gly Ala Gly Asn Asp Asn Val Phe Val
    610                 615                 620

GGG TCA AGT ACT ACC GTT ATT GAT GGC GGG GAC GGA CAT GAT CGA           2664
Gly Ser Ser Thr Thr Val Ile Asp Gly Gly Asp Gly His Asp Arg
    625                 630                 635

GTT CAC TAC AGT AGA GGA GAA TAT GGC GCA TTA GTT ATT GAT GCT           2709
Val His Tyr Ser Arg Gly Glu Tyr Gly Ala Leu Val Ile Asp Ala
    640                 645                 650

ACA GCC GAG ACA GAA AAA GGC TCA TAT TCA GTA AAA CGC TAT GTC           2754
Thr Ala Glu Thr Glu Lys Gly Ser Tyr Ser Val Lys Arg Tyr Val
    655                 660                 665

GGA GAC AGT AAA GCA TTA CAT GAA ACA ATT GCC ACC CAC CAA ACA           2799
Gly Asp Ser Lys Ala Leu His Glu Thr Ile Ala Thr His Gln Thr
    670                 675                 680

AAT GTT GGT AAT CGT GAA GAA AAA ATT GAA TAT CGT CGT GAA GAT           2844
Asn Val Gly Asn Arg Glu Glu Lys Ile Glu Tyr Arg Arg Glu Asp
    685                 690                 695

GAT CGT TTT CAT ACT GGT TAT ACT GTG ACG GAC TCA CTC AAA TCA           2889
Asp Arg Phe His Thr Gly Tyr Thr Val Thr Asp Ser Leu Lys Ser
    700                 705                 710

GTT GAA GAG ATC ATT GGT TCA CAA TTT AAT GAT ATT TTC AAA GGA           2934
Val Glu Glu Ile Ile Gly Ser Gln Phe Asn Asp Ile Phe Lys Gly
    715                 720                 725

AGC CAA TTT GAT GAT GTG TTC CAT GGT GGT AAT GGT GTA GAC ACT           2979
Ser Gln Phe Asp Asp Val Phe His Gly Gly Asn Gly Val Asp Thr
    730                 735                 740

ATT GAT GGT AAC GAT GGT GAC GAT CAT TTA TTT GGT GGC GCA GGC           3024
Ile Asp Gly Asn Asp Gly Asp Asp His Leu Phe Gly Gly Ala Gly
    745                 750                 755

GAT GAT GTT ATC GAT GGA GGA AAC GGT AAC AAT TTC CTT GTT GGA           3069
Asp Asp Val Ile Asp Gly Gly Asn Gly Asn Asn Phe Leu Val Gly
    760                 765                 770

GGA ACC GGT AAT GAT ATT ATC TCG GGA GGT AAA GAT AAT GAT ATT           3114
Gly Thr Gly Asn Asp Ile Ile Ser Gly Gly Lys Asp Asn Asp Ile
    775                 780                 785

TAT GTC CAT AAA ACA GGC GAT GGA AAT GAT TCT ATT ACA GAC TCT           3159
Tyr Val His Lys Thr Gly Asp Gly Asn Asp Ser Ile Thr Asp Ser
```

-continued

|  |  |  |
|---|---|---|
| 790 795 800 | | |
| GGC GGA CAA GAT AAA CTG GCA TTT TCG GAT GTA AAT CTT AAA GAC<br>Gly Gly Gln Asp Lys Leu Ala Phe Ser Asp Val Asn Leu Lys Asp<br>805 810 815 | | 3204 |
| CTC ACC TTT AAG AAA GTA GAT TCT TCT CTC GAA ATC ATT AAT CAA<br>Leu Thr Phe Lys Lys Val Asp Ser Ser Leu Glu Ile Ile Asn Gln<br>820 825 830 | | 3249 |
| AAA GGA GAA AAA GTT CGT ATT GGG AAT TGG TTC TTA GAA GAT GAT<br>Lys Gly Glu Lys Val Arg Ile Gly Asn Trp Phe Leu Glu Asp Asp<br>835 840 845 | | 3294 |
| TTG GCT AGC ACA GTT GCT AAC TAT AAA GCT ACG AAT GAC CGA AAA<br>Leu Ala Ser Thr Val Ala Asn Tyr Lys Ala Thr Asn Asp Arg Lys<br>850 855 860 | | 3339 |
| ATT GAG GAA ATT ATT GGT AAA GGA GGA GAA CGT ATT ACA TCA GAA<br>Ile Glu Glu Ile Ile Gly Lys Gly Gly Glu Arg Ile Thr Ser Glu<br>865 870 875 | | 3384 |
| CAA GTT GAT AAA CTG ATT AAG GAG GGT AAC AAT CAA ATC TCT GCA<br>Gln Val Asp Lys Leu Ile Lys Glu Gly Asn Asn Gln Ile Ser Ala<br>880 885 890 | | 3429 |
| GAA GCA TTA TCC AAA GTT GTG AAT GAT TAC AAT ACG AGT AAA GAT<br>Glu Ala Leu Ser Lys Val Val Asn Asp Tyr Asn Thr Ser Lys Asp<br>895 900 905 | | 3474 |
| AGA CAG AAC GTA TCT AAT AGC TTA GCA AAA TTG ATT TCT TCA GTC<br>Arg Gln Asn Val Ser Asn Ser Leu Ala Lys Leu Ile Ser Ser Val<br>910 915 920 | | 3519 |
| GGG AGC TTT ACG TCT TCC TCA GAC TTT AGG AAT AAT TTA GGA ACA<br>Gly Ser Phe Thr Ser Ser Ser Asp Phe Arg Asn Asn Leu Gly Thr<br>925 930 935 | | 3564 |
| TAT GTT CCT TCA TCA ATA GAT GTC TCG AAT AAT ATT CAA TTA GCT<br>Tyr Val Pro Ser Ser Ile Asp Val Ser Asn Asn Ile Gln Leu Ala<br>940 945 950 | | 3609 |
| AGA GCC GCT TAA<br>Arg Ala Ala<br>955 | | 3621 |
| TATTCAAATC ATAGCAATCC TATGGTGTAA ATTATAGGAT TGTTATTTTT TTAAAGGA | | 3681 |
| AGTTATGGAA CCCAATAAAA ATAAGGATCT TGGTTTAGCT GTAGAAAATC AAACCTAA | | 3741 |
| TGACAGTTCC CGTTTAAAAT TACCGTGTCT GTCAGATTAA TTTGAGCTTA AATTCTTT | | 3801 |
| TGCCCAAATC CGTTTTCCAT CAAGTAATGT TGCCATCGGT GTTCTGCCAC AGCACACT | | 3861 |
| TCCTTGATGT GTTCGATGGT GATTATAATA CATTCATCTA AATCAGCTTG TAATGTCG | | 3921 |
| AAATCCGTAT ATATTTTCTT CCTAAATGCG ACTTGGTAAA ATTCTTGTAA GATAGTCT | | 3981 |
| TGAAAACGTT CACAGATACC ATTCGTCTGT GGATGCTTCA CTTTCGTTTT AGTATGCT | | 4041 |
| ATGTCATTTA TCGCTAAATA AAGCTCATAA TCGTGATTTT CCACTTTGCC ACAATATT | | 4101 |
| CTGCCACGGT CGGTGAGAAT ACGCAACATC GGTAATCCTT GGGCTTCAAA GAACGGCA | | 4161 |
| ACTTTATGAT TGAGCATATC TGCAGCGGCA ATTGCGGTTT TCATTGTGTA GAGCTTTG | | 4221 |
| AAAGCAACCT TACTATAAGT ATCAACAAAT GTTTGCTGAT AAATGCGTCC AACACCTT | | 4281 |
| AAATTACCTA CATAAAAGGT ATCTTGTGAA CCTAAATAGC CCGGATGAGC GGTTTCAA | | 4341 |
| TCTCCACTCG ATATATCATC CTCTTTCTTA CGTTCTAGGG CTTGGACTTG ACTTTCAT | | 4401 |
| AGAATAATGC CTTTCTCAGC CACTTCTTTC TCTAGTGCAT TTAAACGCTG TTTAAAGT | | 4461 |
| GTAAGATTAT GACGTAGCCA AATGGAACGA ACACCACCGG CTGAAACAAA CACACCTT | | 4521 |
| TTGCGAAGTT CGTTACTCAC TCGAACTTGT CCGTAAGCTG GAAAATCTAG AGCAAATT | | 4581 |
| ACAACAGCTT GCTCAATGTG CTCGTCTACT CGATTTTTGA TATTCGGTAC CCGACGAG | | 4641 |

```
TGCTTAAGTA ATGCTTCAAC ACCGCCTTGC GCTACGGCTT GTTGATAGCG ATAGAATG          4701

TCTCGGCTCA TTCCCATCGC TTTACAAGCT                                         4731

(2) INFORMATION FOR SEQ ID NO: 3:

(i) SEQUENCE CHARACTERISTICS:
            (A) LENGTH: 4190
            (B) TYPE: nucleic acid
            (C) STRANDEDNESS: single
            (D) TOPOLOGY: linear (xi) SEQUENCE DESCRIPTION: SEQ ID NO: 3:

GTAGATATTC TTTTAATATC AAACAACTAT TGTTATTTGT CTGAGTGTAG ATATGTAGCA          60

TTGTGTATTT CTTTATTTAC AACTCTAATC TTAATCTAAA AAGATTTCTA TATTTTCTT         120

GTAAGAAATT TTGTTAAAAT CCGACTAACT ATATAATTAA CGGTTCTTAA AGTGGATAA         180

TAATAAAATT ATGAGTTATA AAAATGTTAA AAATTTAACA GATGATTTTA CAACTTTAG         240

GCATATCGCT TGGTTGTGGG CTAATTCTCC GTTACATAAG GAGTGGTCTA TCTCTTTGT         300

TACTAAGAAT ATTTTGCCAG CCATTCAACA TGATCAATAT ATTTTACTTA TGCGAGATG         360

GTTCCCTGTA GCGTTTTGTA GTTGGGCAAA TTTAACGTTA ACTAATGAAG TGAAGTATG         420

ACGTGATGTG ACGTCATTGA CTTTTGAAGA TTGGAATTCA GGAGAACGAA AATGGTTGA         480

CGACTGGATT GCGCCATTTG GGGATAACAA TACGCTTTAT AGATATATGC GTAAAAAAT         540

TCCTAATGAA GTATTCCGGG CCATTCGAGT ATATCCTGGT TCTACAGAAG CGAAAATCA         600

TCATGTTCAA GGAGGACAAA TTAATAAATT TACAGCTAAA AAATTAATAC AACAATATC         660

GGAAGAACTT ATTCAAGTTC TTAACAATCA CAAAAAAATT GTAAGAGGAT AAAAT            715

ATG AGT ACT TGG TCA AGC ATG TTA GCC GAC TTA AAA AAA CGG GCT              760
Met Ser Thr Trp Ser Ser Met Leu Ala Asp Leu Lys Lys Arg Ala
 1               5                  10                  15

GAA GAA GCC AAA AGA CAA GCC AAA AAA GGC TAC GAT GTA ACT AAA              805
Glu Glu Ala Lys Arg Gln Ala Lys Lys Gly Tyr Asp Val Thr Lys
                20                  25                  30

AAT GGT TTG CAA TAT GGG GTG AGT CAA GCA AAA TTA CAA GCA TTA              850
Asn Gly Leu Gln Tyr Gly Val Ser Gln Ala Lys Leu Gln Ala Leu
                35                  40                  45

GCA GCT GGT AAA GCC GTT CAA AAG TAC GGT AAT AAA TTA GTT TTA              895
Ala Ala Gly Lys Ala Val Gln Lys Tyr Gly Asn Lys Leu Val Leu
                50                  55                  60

GTT ATT CCA AAA GAG TAT GAC GGA AGT GTT GGT AAC GGT TTC TTT              940
Val Ile Pro Lys Glu Tyr Asp Gly Ser Val Gly Asn Gly Phe Phe
                65                  70                  75

GAT TTA GTA AAA GCA GCT GAG GAA TTA GGC ATT CAA GTT AAA TAT              985
Asp Leu Val Lys Ala Ala Glu Glu Leu Gly Ile Gln Val Lys Tyr
                80                  85                  90

GTT AAC CGT AAT GAA TTG GAA GTT GCC CAT AAA AGT TTA GGT ACC             1030
Val Asn Arg Asn Glu Leu Glu Val Ala His Lys Ser Leu Gly Thr
                95                 100                 105

GCA GAC CAA TTC TTG GGT TTA ACA GAA CGT GGA CTT ACT TTA TTT             1075
Ala Asp Gln Phe Leu Gly Leu Thr Glu Arg Gly Leu Thr Leu Phe
               110                 115                 120

GCA CCG CAA CTA GAT CAG TTC TTA CAA AAA CAT TCA AAA ATT TCT             1120
Ala Pro Gln Leu Asp Gln Phe Leu Gln Lys His Ser Lys Ile Ser
               125                 130                 135

AAC GTA GTG GGC AGT TCT ACT GGT GAT GCA GTA AGT AAA CTT GCT             1165
Asn Val Val Gly Ser Ser Thr Gly Asp Ala Val Ser Lys Leu Ala
               140                 145                 150

AAG AGT CAA ACT ATT ATT TCA GGA ATT CAA TCT GTA TTA GGT ACT             1210
```

```
                                                    -continued

Lys Ser Gln Thr Ile Ile Ser Gly Ile Gln Ser Val Leu Gly Thr
            155                 160                 165

GTA TTA GCA GGT ATT AAT CTT AAT GAA GCT ATT ATT AGT GGC GGT         1255
Val Leu Ala Gly Ile Asn Leu Asn Glu Ala Ile Ile Ser Gly Gly
            170                 175                 180

TCA GAG CTC GAA TTA GCT GAA GCT GGT GTT TCT TTA GCC TCT GAG         1300
Ser Glu Leu Glu Leu Ala Glu Ala Gly Val Ser Leu Ala Ser Glu
            185                 190                 195

CTG CTT AGT AAT ATT GCT AAA GGT ACA ACA ATA GAT GCT TTC             1345
Leu Leu Ser Asn Ile Ala Lys Gly Thr Thr Ile Asp Ala Phe
            200                 205                 210

ACT ACA CAA ATC CAG AAC TTT GGG AAA TTA GTG GAA AAT GCT AAA         1390
Thr Thr Gln Ile Gln Asn Phe Gly Lys Leu Val Glu Asn Ala Lys
            215                 220                 225

GGG TTA GGT GGT GTT GGC CGC CAA TTA CAG AAT ATT TCA GGT TCT         1435
Gly Leu Gly Gly Val Gly Arg Gln Leu Gln Asn Ile Ser Gly Ser
            230                 235                 240

GCA TTA AGC AAA ACT GGA TTA GGT TTG GAT ATT ATC TCA AGC TTA         1480
Ala Leu Ser Lys Thr Gly Leu Gly Leu Asp Ile Ile Ser Ser Leu
            245                 250                 255

CTT TCA GGA GTA ACT GCA AGT TTT GCT TTA GCG AAT AAG AAT GCT         1525
Leu Ser Gly Val Thr Ala Ser Phe Ala Leu Ala Asn Lys Asn Ala
            260                 265                 270

TCA ACA AGC ACT AAA GTT GCT GCT GGC TTT GAA CTC TCA AAT CAA         1570
Ser Thr Ser Thr Lys Val Ala Ala Gly Phe Glu Leu Ser Asn Gln
            275                 280                 285

GTA ATT GGT GGT ATT ACG AAA GCA GTA TCA AGC TAT ATT CTT GCA         1615
Val Ile Gly Gly Ile Thr Lys Ala Val Ser Ser Tyr Ile Leu Ala
            290                 295                 300

CAG CGT TTA GCT GCT GGT TTA TCT TCG ACA GGT CCT GCT GCA GCA         1660
Gln Arg Leu Ala Ala Gly Leu Ser Ser Thr Gly Pro Ala Ala Ala
            305                 310                 315

CTA ATT GCG TCT AGT ATT TCT TTA GCA ATC AGT CCA TTG GCG TTT         1705
Leu Ile Ala Ser Ser Ile Ser Leu Ala Ile Ser Pro Leu Ala Phe
            320                 325                 330

TTA CGT GTA GCT GAT AAT TTT AAT CGT TCT AAA GAA ATT GGC GAA         1750
Leu Arg Val Ala Asp Asn Phe Asn Arg Ser Lys Glu Ile Gly Glu
            335                 340                 345

TTT GCT GAA CGT TTC AAA AAA TTG GGC TAT GAC GGC GAT AAA CTA         1795
Phe Ala Glu Arg Phe Lys Lys Leu Gly Tyr Asp Gly Asp Lys Leu
            350                 355                 360

CTT TCA GAG TTT TAT CAC GAA GCT GGT ACT ATT GAT GCC TCA ATT         1840
Leu Ser Glu Phe Tyr His Glu Ala Gly Thr Ile Asp Ala Ser Ile
            365                 370                 375

ACT ACA ATT AGT ACA GCA CTT TCT GCT ATC GCA GCT GGA ACG GCC         1885
Thr Thr Ile Ser Thr Ala Leu Ser Ala Ile Ala Ala Gly Thr Ala
            380                 385                 390

GCC GCG AGT GCA GGT GCA TTA GTT GGC GCA CCA ATT ACT TTG TTG         1930
Ala Ala Ser Ala Gly Ala Leu Val Gly Ala Pro Ile Thr Leu Leu
            395                 400                 405

GTT ACT GGT ATC ACA GGA TTA ATT TCT GGT ATT TTA GAG TTC TCT         1975
Val Thr Gly Ile Thr Gly Leu Ile Ser Gly Ile Leu Glu Phe Ser
            410                 415                 420

AAA CAA CCA ATG TTA GAT CAT GTT GCA TCG AAA ATT GGT AAC AAA         2020
Lys Gln Pro Met Leu Asp His Val Ala Ser Lys Ile Gly Asn Lys
            425                 430                 435

ATT GAC GAA TGG GAG AAA AAA TAC GGT AAA AAT TAC TTC GAG AAT         2065
Ile Asp Glu Trp Glu Lys Lys Tyr Gly Lys Asn Tyr Phe Glu Asn
            440                 445                 450

GGC TAT GAT GCT CGT CAT AAA GCT TTC TTA GAA GAT TCA TTC TCA         2110
```

-continued

| | | |
|---|---|---|
| Gly Tyr Asp Ala Arg His Lys Ala Phe Leu Glu Asp Ser Phe Ser<br>455 460 465 | | |
| TTA TTG TCT AGT TTT AAT AAA CAA TAT GAA ACT GAA AGA GCT GTT<br>Leu Leu Ser Ser Phe Asn Lys Gln Tyr Glu Thr Glu Arg Ala Val<br>470 475 480 | 2155 | |
| TTA ATT ACA CAA CAA CGT TGG GAT GAA TAT ATT GGC GAA CTT GCG<br>Leu Ile Thr Gln Gln Arg Trp Asp Glu Tyr Ile Gly Glu Leu Ala<br>485 490 495 | 2200 | |
| GGT ATT ACT GGC AAA GGT GAC AAA CTC TCT AGT GGT AAG GCG TAT<br>Gly Ile Thr Gly Lys Gly Asp Lys Leu Ser Ser Gly Lys Ala Tyr<br>500 505 510 | 2245 | |
| GTA GAT TAC TTT CAA GAA GGT AAA TTA TTA GAG AAA AAA CCT GAT<br>Val Asp Tyr Phe Gln Glu Gly Lys Leu Leu Glu Lys Lys Pro Asp<br>515 520 525 | 2290 | |
| GAC TTT AGC AAA GTA GTT TTC GAT CCA ACT AAG GGC GAA ATT GAT<br>Asp Phe Ser Lys Val Val Phe Asp Pro Thr Lys Gly Glu Ile Asp<br>530 535 540 | 2335 | |
| ATT TCA AAT AGC CAA ACG TCA ACG TTG TTA AAA TTT GTT ACG CCA<br>Ile Ser Asn Ser Gln Thr Ser Thr Leu Leu Lys Phe Val Thr Pro<br>545 550 555 | 2380 | |
| TTA TTA ACA CCA GGT ACA GAG TCA CGT GAA AGA ACT CAA ACA GGT<br>Leu Leu Thr Pro Gly Thr Glu Ser Arg Glu Arg Thr Gln Thr Gly<br>560 565 570 | 2425 | |
| AAA TAT GAA TAT ATC ACG AAG TTA GTT GTA AAA GGT AAA GAT AAA<br>Lys Tyr Glu Tyr Ile Thr Lys Leu Val Val Lys Gly Lys Asp Lys<br>575 580 585 | 2470 | |
| TGG GTT GTT AAT GGC GTT AAA GAT AAA GGT GCC GTT TAT GAT TAT<br>Trp Val Val Asn Gly Val Lys Asp Lys Gly Ala Val Tyr Asp Tyr<br>590 595 600 | 2515 | |
| ACT AAT TTA ATT CAA CAT GCT CAT ATT AGT TCA TCA GTA GCA CGT<br>Thr Asn Leu Ile Gln His Ala His Ile Ser Ser Ser Val Ala Arg<br>605 610 615 | 2560 | |
| GGT GAA GAA TAC CGT GAA GTT CGT TTG GTA TCT CAT CTA GGC AAT<br>Gly Glu Glu Tyr Arg Glu Val Arg Leu Val Ser His Leu Gly Asn<br>620 625 630 | 2605 | |
| GGT AAT GAC AAA GTG TTC TTA GTC GCG GGT TCC GCA GAA ATT CAC<br>Gly Asn Asp Lys Val Phe Leu Val Ala Gly Ser Ala Glu Ile His<br>635 640 645 | 2650 | |
| GCT GGT GAA GGT CAT GAT GTG GTT TAT TAT GAT AAA ACC GAT ACA<br>Ala Gly Glu Gly His Asp Val Val Tyr Tyr Asp Lys Thr Asp Thr<br>650 655 660 | 2695 | |
| GGT CTT TTA GTA ATT GAT GGA ACC AAA GCG ACT GAA CAA GGG CGT<br>Gly Leu Leu Val Ile Asp Gly Thr Lys Ala Thr Glu Gln Gly Arg<br>665 670 675 | 2740 | |
| TAT TCT GTT ACG CGC GAA TTG AGT GGT GCT ACA AAA ATC CTG AGA<br>Tyr Ser Val Thr Arg Glu Leu Ser Gly Ala Thr Lys Ile Leu Arg<br>680 685 690 | 2785 | |
| GAA GTA ATA AAA AAT CAA AAA TCT GCT GTT GGT AAA CGT GAA GAA<br>Glu Val Ile Lys Asn Gln Lys Ser Ala Val Gly Lys Arg Glu Glu<br>695 700 705 | 2830 | |
| ACC TTG GAA TAT CGT GAT TAT GAA TTA ACG CAA TCA GGT AAT AGT<br>Thr Leu Glu Tyr Arg Asp Tyr Glu Leu Thr Gln Ser Gly Asn Ser<br>710 715 720 | 2875 | |
| AAC CTA AAA GCA CAT GAT GAA TTA CAT TCA GTA GAA GAA ATT ATT<br>Asn Leu Lys Ala His Asp Glu Leu His Ser Val Glu Glu Ile Ile<br>725 730 735 | 2920 | |
| GGA AGT AAT CAG AGA GAC GAA TTT AAA GGT AGT AAA TTC AGA GAT<br>Gly Ser Asn Gln Arg Asp Glu Phe Lys Gly Ser Lys Phe Arg Asp<br>740 745 750 | 2965 | |
| ATT TTC CAT GGT GCC GAT GGT GAT GAT CTA TTA AAT GGT AAT GAT | 3010 | |

```
Ile Phe His Gly Ala Asp Gly Asp Leu Leu Asn Gly Asn Asp
            755                 760                 765

GGG GAT GAT ATT CTA TAC GGT GAT AAA GGT AAC GAT GAG TTA AGA      3055
Gly Asp Asp Ile Leu Tyr Gly Asp Lys Gly Asn Asp Glu Leu Arg
            770                 775                 780

GGT GAT AAT GGT AAC GAC CAA CTT TAT GGT GGT GAA GGT AAT GAC      3100
Gly Asp Asn Gly Asn Asp Gln Leu Tyr Gly Gly Glu Gly Asn Asp
            785                 790                 795

AAA CTA TTA GGA GGT AAT GGC AAT AAT TAC CTC AGT GGT GGT GAT      3145
Lys Leu Leu Gly Gly Asn Gly Asn Asn Tyr Leu Ser Gly Gly Asp
            800                 805                 810

GGC AAT GAT GAG CTT CAA GTC TTA GGC AAA TGG TTT TTA ATG TGC      3190
Gly Asn Asp Glu Leu Gln Val Leu Gly Lys Trp Phe Leu Met Cys
            815                 820                 825

TTC GTG GCG GTA AAG GCG ATG ATA AAC TTT ATG GTA GCT CAG GTT      3235
Phe Val Ala Val Lys Ala Met Ile Asn Phe Met Val Ala Gln Val
            830                 835                 840

CTG ATT TAC CTT GAT GGT GGA GAA GGT AAT GAT TAT CTA GAA GGA      3280
Leu Ile Tyr Leu Asp Gly Gly Glu Gly Asn Asp Tyr Leu Glu Gly
            845                 850                 855

GGC GAT GGT AGC GAT TTT TAT GTT TAC TGT TCC ACT TCA GGT AAT      3325
Gly Asp Gly Ser Asp Phe Tyr Val Tyr Cys Ser Thr Ser Gly Asn
            860                 865                 870

CAT ACT ATT TAT GAT CAA GGT AAA TCT AGT GAT TTA GAT AAA CTA      3370
His Thr Ile Tyr Asp Gln Gly Lys Ser Ser Asp Leu Asp Lys Leu
            875                 880                 885

TAT TTG TCT GAT TTT TCC TTC GAT CGT CTT CTT GTT GAG AAA GTT      3415
Tyr Leu Ser Asp Phe Ser Phe Asp Arg Leu Leu Val Glu Lys Val
            890                 895                 900

GAT GAT AAC CTT GTA CTT AGA AGT AAT GAA AGT AGT CAT AAT AAT      3460
Asp Asp Asn Leu Val Leu Arg Ser Asn Glu Ser Ser His Asn Asn
            905                 910                 915

GGA GTA CTC ACA ATC AAA GAC TGG TTT AAA GAA GGG AAT AAA TAT      3505
Gly Val Leu Thr Ile Lys Asp Trp Phe Lys Glu Gly Asn Lys Tyr
            920                 925                 930

AAC CAT AAA ATT GAA CAA ATT GTT GAT AAA AAT GGT AGA AAA TTG      3550
Asn His Lys Ile Glu Gln Ile Val Asp Lys Asn Gly Arg Lys Leu
            935                 940                 945

ACA GCA GAG AAT TTA GGA ACT TAT TTC AAA AAT GCT CCA AAA GCT      3595
Thr Ala Glu Asn Leu Gly Thr Tyr Phe Lys Asn Ala Pro Lys Ala
            950                 955                 960

GAC AAT TTG CTT AAT TAT GCA ACT AAA GAA GAT CAG AAT GAA AGC      3640
Asp Asn Leu Leu Asn Tyr Ala Thr Lys Glu Asp Gln Asn Glu Ser
            965                 870                 975

AAT TTA TCT TCA CTT AAA ACT GAA TTA AGT AAA ATT ATT ACT AAT      3685
Asn Leu Ser Ser Leu Lys Thr Glu Leu Ser Lys Ile Ile Thr Asn
            980                 985                 990

GCA GGT AAT TTT GGT GTG GCA AAA CAA GGT AAT ACT GGA ATC AAT      3730
Ala Gly Asn Phe Gly Val Ala Lys Gln Gly Asn Thr Gly Ile Asn
            995                1000                1005

ACA GCT GCC TTG AAC AAT GAA GTG AAT AAA ATC ATT TCT TCT GCT      3775
Thr Ala Ala Leu Asn Asn Glu Val Asn Lys Ile Ile Ser Ser Ala
           1010                1015                1020

AAT ACC TTT GCT ACT TCA CAA TTG GGT GGC TCA GGG ATG GGA ACA      3820
Asn Thr Phe Ala Thr Ser Gln Leu Gly Gly Ser Gly Met Gly Thr
           1025                1030                1035

TTA CCA TCA ACG AAT GTA AAT TCA ATG ATG CTA GGT AAC CTA GCT      3865
Leu Pro Ser Thr Asn Val Asn Ser Met Met Leu Gly Asn Leu Ala
           1040                1045                1050

AGA GCA GCT TAA TCA TCTGCATAAT CAATAGCAAT                        3900
Arg Ala Ala
```

```
Arg Ala Ala

CCTATGGCTA TTCTAGGATT GCTATTTTAT TTATGGAGTC ACAAATGCCT TTTAACGA      3960

AAATAGATTA CGGATTACAT GCATTGGTAA TTCTCGCGCA ATATCACAAT GTTGCCGT      4020

ACCCTGAAGA GGTAAAACAT AAATTTGATC TTGATGGCAA AGGATTGGAT CTTGTTGC      4080

GGTTATTAGC AGCAAAATCA TTAGAATTAA AAGCCAAACG AGTAAAAAAG AGTATTGA      4140

GTTTACCATT TATTCATCTT CCTGCTTTAA TCTGGCGAGA TGATGGTCAA               4190
```